(12) United States Patent
Miller et al.

(10) Patent No.: US 10,995,317 B2
(45) Date of Patent: May 4, 2021

(54) NK CELLS EXHIBITING AN ADAPTIVE PHENOTYPE AND METHODS FOR PREPARING AND FOR USING

(71) Applicant: REGENTS OF THE UNIVERSITY OF MINNESOTA, Minneapolis, MN (US)

(72) Inventors: Jeffrey Miller, Minneapolis, MN (US); Frank Cichocki, Minneapolis, MN (US); Yenan Bryceson, Stockholm (SE); Heinrich Schlums, Stockholm (SE)

(73) Assignee: Regents of the University of Minnesota, Minneapolis, MN (US)

( * ) Notice: Subject to any disclaimer, the term of this patent is extended or adjusted under 35 U.S.C. 154(b) by 0 days.

(21) Appl. No.: 15/759,723

(22) PCT Filed: Sep. 14, 2016

(86) PCT No.: PCT/US2016/051685
§ 371 (c)(1),
(2) Date: Mar. 13, 2018

(87) PCT Pub. No.: WO2017/048809
PCT Pub. Date: Mar. 23, 2017

(65) Prior Publication Data
US 2018/0258396 A1 Sep. 13, 2018

Related U.S. Application Data

(60) Provisional application No. 62/295,708, filed on Feb. 16, 2016, provisional application No. 62/218,366, filed on Sep. 14, 2015.

(51) Int. Cl.
| | | |
|---|---|---|
| *C12N 5/0783* | (2010.01) | |
| *A61K 35/17* | (2015.01) | |
| *A61P 35/00* | (2006.01) | |
| *A61K 39/245* | (2006.01) | |
| *A61K 45/06* | (2006.01) | |
| *C12N 7/00* | (2006.01) | |
| *A61K 39/00* | (2006.01) | |

(52) U.S. Cl.
CPC ............ *C12N 5/0646* (2013.01); *A61K 35/17* (2013.01); *A61K 39/245* (2013.01); *A61K 45/06* (2013.01); *A61P 35/00* (2018.01); *C12N 7/00* (2013.01); *A61K 2039/572* (2013.01); *A61K 2039/585* (2013.01); *C12N 2501/04* (2013.01); *C12N 2501/2315* (2013.01); *C12N 2501/2321* (2013.01); *C12N 2501/42* (2013.01); *C12N 2501/599* (2013.01); *C12N 2502/1121* (2013.01); *C12N 2502/1157* (2013.01); *C12N 2502/1352* (2013.01); *C12N 2710/16134* (2013.01)

(58) Field of Classification Search
None
See application file for complete search history.

(56) References Cited

U.S. PATENT DOCUMENTS

| 8,518,397 B2 | 8/2013 | Beck |
|---|---|---|
| 2014/0186380 A1 | 7/2014 | Gurney et al. |

FOREIGN PATENT DOCUMENTS

| WO | WO 2006/039545 | 4/2006 |
|---|---|---|
| WO | WO 2014/037422 | 3/2014 |

OTHER PUBLICATIONS

Strengell et al., J Immunol. Jun. 1, 2003;170(11):5464-5469 (Year: 2003).*
De Smedt et al., Blood. Oct. 1, 2007;110(7):2696-703 (Year: 2007).*
Meehan et al., PLoS One. 2013;8(3):e60144. (Year: 2013).*
Wu et al., J Virol. Jul. 2013; 87(13): 7717-7725 (Year: 2013).*
Backer et al., A Central Role for Notch in Effector CD8 T Cell Differentiation, Nat Immunol dated Dec. 2014, 26 pages.
Beziat et al., "CMV Drives Clonal Expansion of NKG2C NK Cells Expressing Slef-Specific KIRs in Chronic Hepatitis Patients," European Journal of Immunology, vol .42. No. 2, dated Feb. 1, 2012, 11 pages.
Bjorkstrom et al., "Expression patterns of NKG2A, KIR, and CD57 define a process of CD56dim NK-cell differentiation uncoupled from NK-cell education," Blood, dated Nov. 11, 2010, 13 pages.
Chang et al, "Corrected group prognostic curves and summary statistics," Journal of Clinical Epidemiology, 35(8) pp. 669-674, 1982.
Cichocki et al., "CD56(dim)CD57(+)NKG2C(+) NK cell expansion is associated with reduced leukemia re lapse after reduced intensity HCT," Leukemia (Basingstoke), vol. 30, No. 2, dated Feb. 2016, 31 pages.
Cichocki et al., "The Past, Present, and Future of NK Cells in Hematopoietic Cell Transplantation and Adoptive Transfer," Natural Killer Cells, dated Jun. 3, 2015, 19 pages.
Corzo et al., "Mechanism regulating reactive oxygen species in tumor induced myeloid-derived suppressor cells," J Immunol, dated May 1, 2009, 19 pages.
Davis et al., Adaptive NK cell and KIR-expressing T cell responses are induced by CMV and are associated with protection against CMV reactivation after allogeneic donor hematopoietic cell transplantation, Biol Blood Marrow Transplant, dated Sep. 2015, 18 pages.
Denman et al., "Membrane-Bound IL-21 Promotes Sustained Ex Vivo Proliferation of Human Natural Killer Cells," PLOS One, dated Jan. 18, 2012, 13 pages.
(Continued)

*Primary Examiner* — Daniel C Gamett
(74) *Attorney, Agent, or Firm* — Fish & Richardson P.C.

(57) ABSTRACT

This disclosure describes an adaptive NK cell, an isolated population of adaptive Natural Killer (NK) cells, a composition including an adaptive NK cell, and methods for producing, preparing, and using an adaptive NK cell or an isolated population or composition including an adaptive NK cell. The adaptive NK cells may be used to treat a viral infection or a tumor.

11 Claims, 36 Drawing Sheets

(56) References Cited

OTHER PUBLICATIONS

Fine et al., "A Proportional Hazards Model for the Subdistribution of a Competing Risk," American Statistical Association, dated Jun. 1999, 15 pages.
Foley et al., "Cytomegalovirus Reactivation after Allogeneic Transplantation Promotes a Lasting Increase in Educated NKG2C Natural Killer Cells with Potent Function," Blood Journal, dated Dec. 16, 2011, 33 pages.
Foley et al., "Human Cytomegalovirus (CMV)-Induced Memory-like NKG2C NK Cells are Transplantable and Expand in Vivo in Response to Recipient CMV Antigen," The Journal of Immunology, dated Oct. 17, 2012, 8 pages.
Garu et al., "Genetic Immunization With In Vivo Dendritic Cell-targeting Liposomal DNA Vaccine Carrier Induces Long-lasting Antitumor Immune Response," The American Society of Gene and Cell Therapy, dated Apr. 10, 2015, 13 pages.
International Preliminary Report on Patentability in International Application No. PCT/US2016/051685, dated Apr. 29, 2018, 8 pages.
International Search Report and Written Opinion in International Application No. PCT/US2016/051685, dated Dec. 16, 2016, 14 pages.
Kaplan et al., "Nonparametric Estimation from Incomplete Observations," Journal of the American Statistical Association, vol. 53, No. 282, dated Jun. 1958, 26 pages.
Lopez-Verges et al., "CD57 defines a functionally distinct population of mature NK cells in the human CD56dimCD16+ NK-cell subset," Blood, Nov. 11, 2010, 11 pages.
Lopez-Verges et al., "Expansion of a unique CD57+NKG2C natural killer cell subset during acute human cytomegalovirus infection," dated Jul. 6, 2011, 8 pages.
Marvel et al., "Myeloid-Derived Suppressor Cells in the Tumor Microenvironment: Expect the Unexpected," The Journal of Clinical Investigation, dated Sep. 2015, 10 pages.
Ostrand-Rosenberg et al., "Inflammation and Cancer Myeloid-Derived Suppressor Cells: Linking," The Journal of Immunology, dated Jan. 21, 2009, 9 pages.
Pass et al., "Vaccine Prevention of Maternal Cytomegalovirus Infection," The New England Journal of Medicine, dated Mar. 19, 2009.
Rolle et al., "IL-12-Producing Monocytes and HLA-E Control HCMV-Driven NKG2C+ NK Cell Expansion," The Journal of Clinical Investigation, Dec. 2014, 13 pages.
Sarhan et al., "Adaptive NK Cells with Low TIGIT Expression are Inherently Resistant to Myeloid-Derived Suppressor Cells.," Cancer Research, vol. 76, No. 19., dated Aug. 8, 2016.
Schlums et al., "Diversification and Functional Specialization of Human NK Cell Sunsets," Natural Killer Cells, dated Oct. 16, 2015.
Schlums et al., "Cytomegalovirus Infection Drives Adaptive Epigenetic Diversification of NK Cells with Altered Signaling and Effector Function," Immunity, vol. 43, No. 3, dated Mar. 1, 2015, 15 pages.
Schmitt et al., "Induction of T Cell Development from Hematopoietic Progenitor Cells by Delta-like-1 In Vitro," Immunity: Science Direct, dated Dec. 2002, 8 pages.
Stanietsky et al., "Mouse TIGIT inhibits NK-cell cytotoxicity upon interaction with PVR," European Journal of Immunology, vol. 43, No. 8, dated Aug. 2013, 13 pages.
Warren et al., "Biphasic response of NK cells expressing both activating and inhibitory killer Ig-like receptors," International Immunology, dated Aug. 1, 2001, 10 pages.
Beziat et al., "CMV drives clonal expansion of NKG2C+ NK cells expressing self-specific KIRs in chronic hepatitis patients," Eur. J. Immunology. Feb. 2012, 42(2):447-457.
Cichocki et al., "The Past, Present, and Future of NK Cells in Hematopoietic Cell Transplantation and Adoptive Transfer," Curr. Top. Microbiol. Immunology, Jun. 3, 2015, 395:225-243.
JP Office Action in Japanese Appln. No. 2018-513478, dated Oct. 6, 2020 16 pages (with machine translation).
Schlums et al., "Cytomegalovirus Infection Drives Adaptive Epigenetic Diversification of NK Cells with Altered Signaling and Effector Function," Immunity, Mar. 17, 2015, 42:443-456.

* cited by examiner

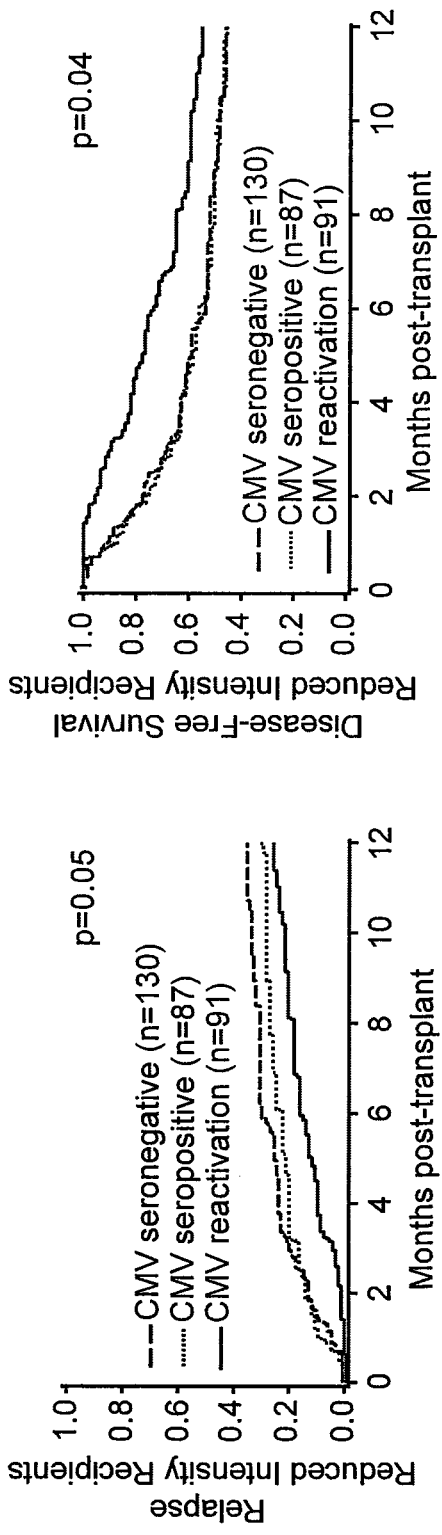
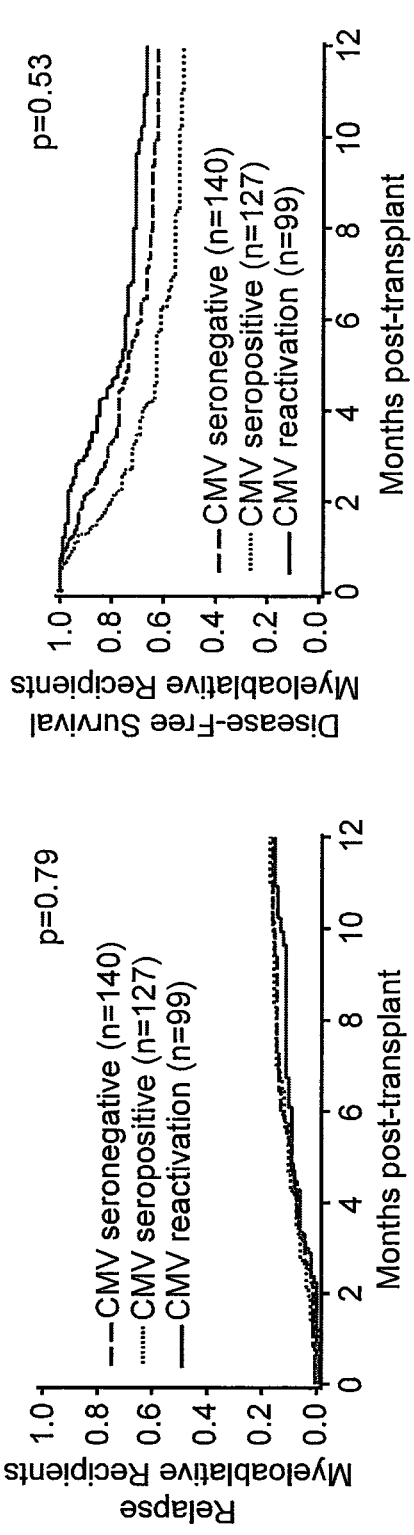

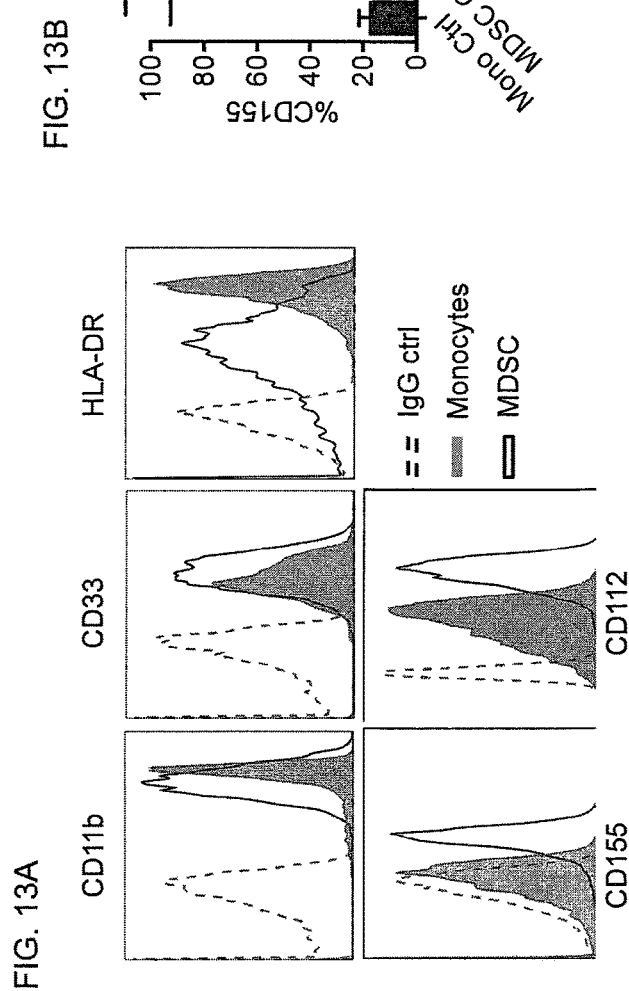
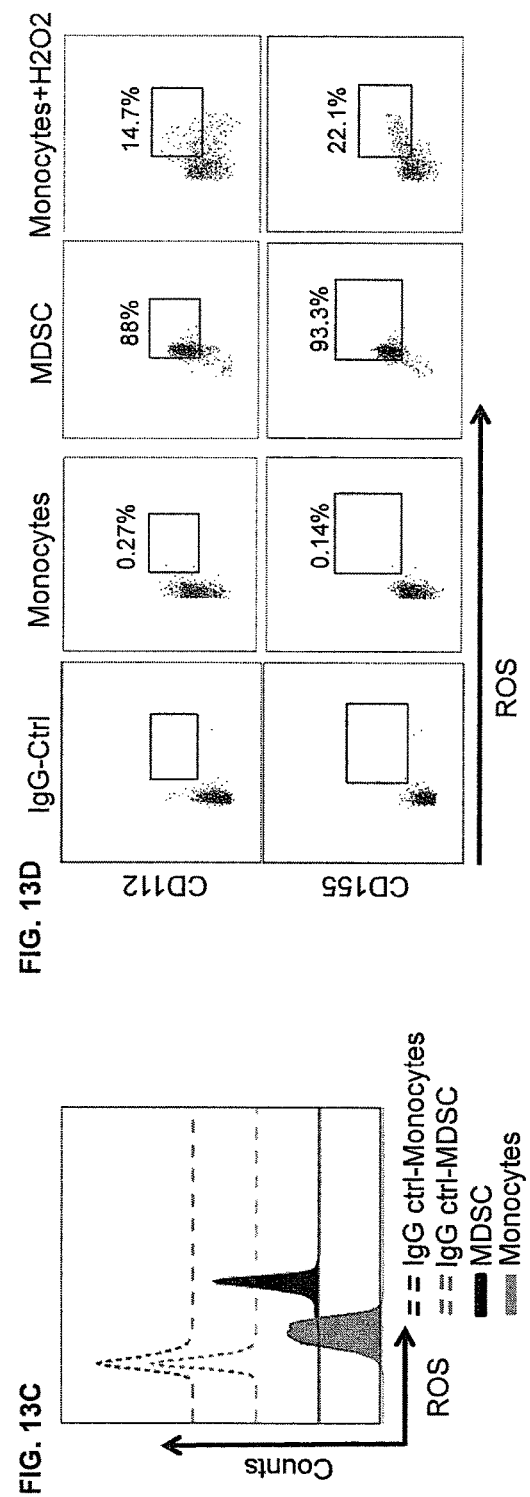

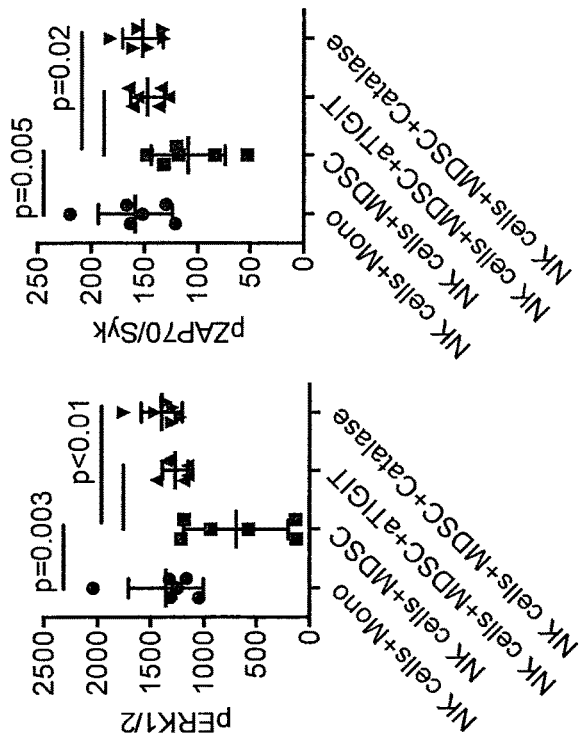
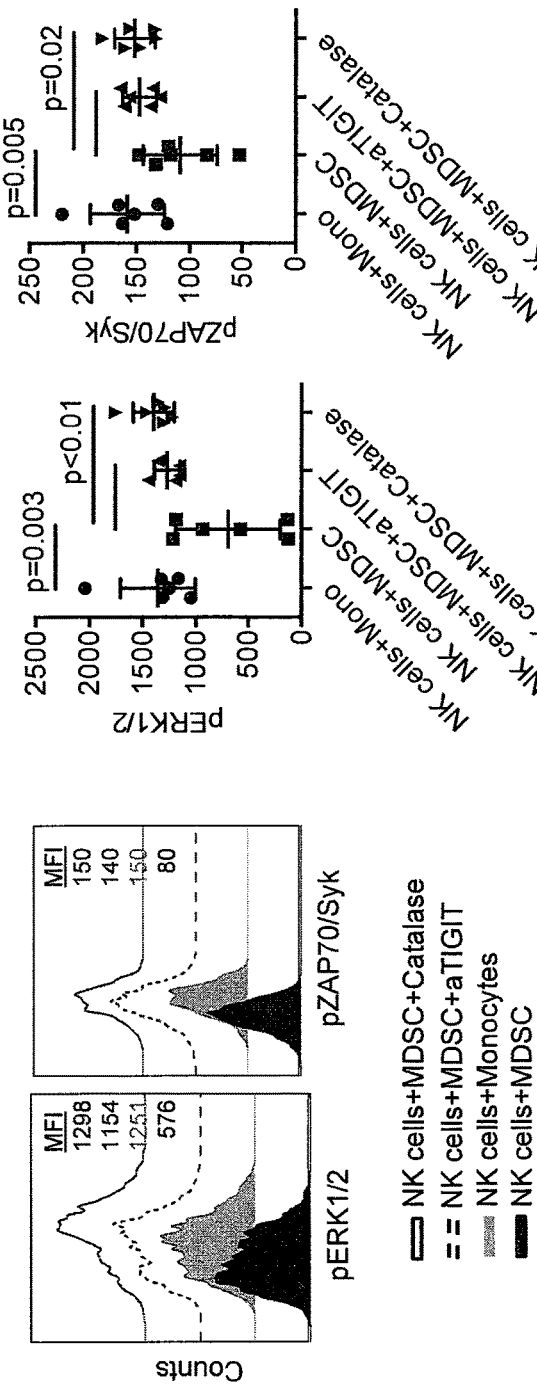
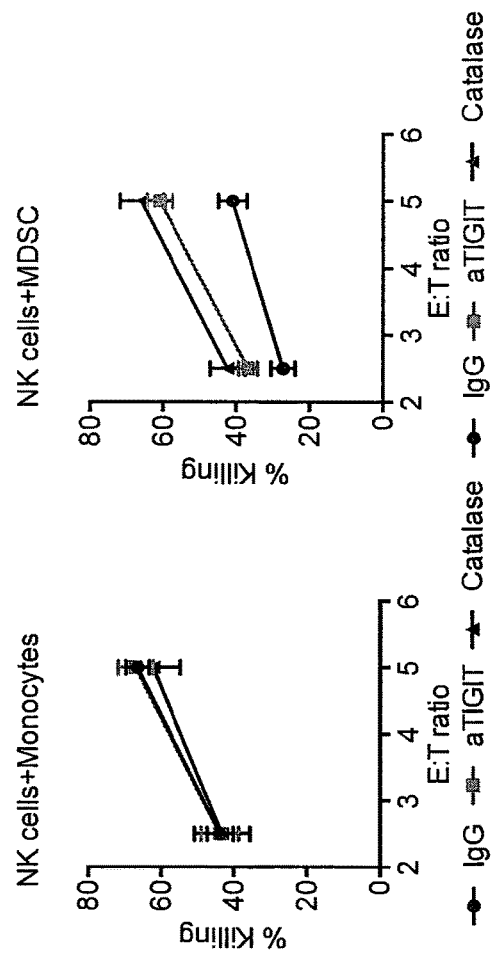

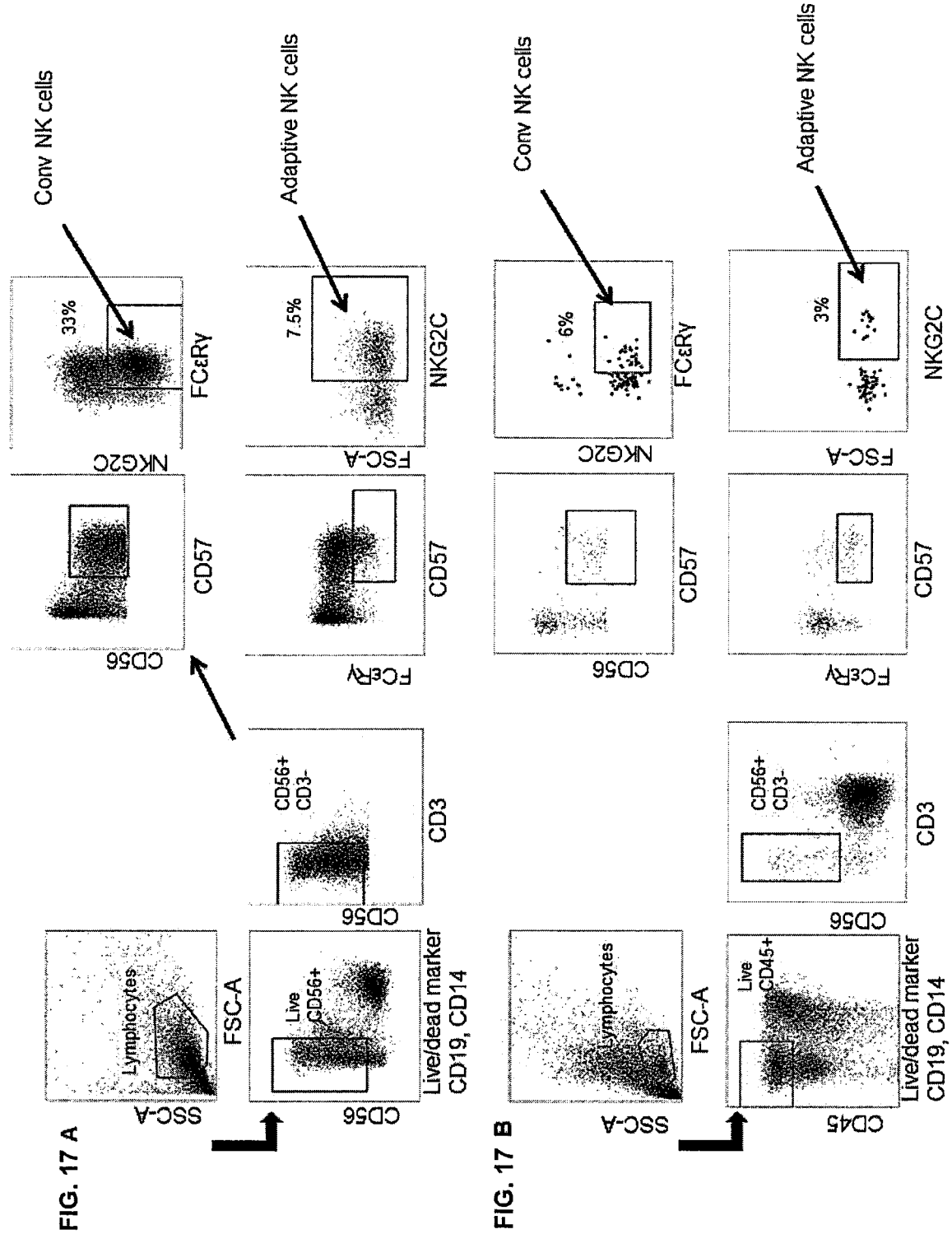

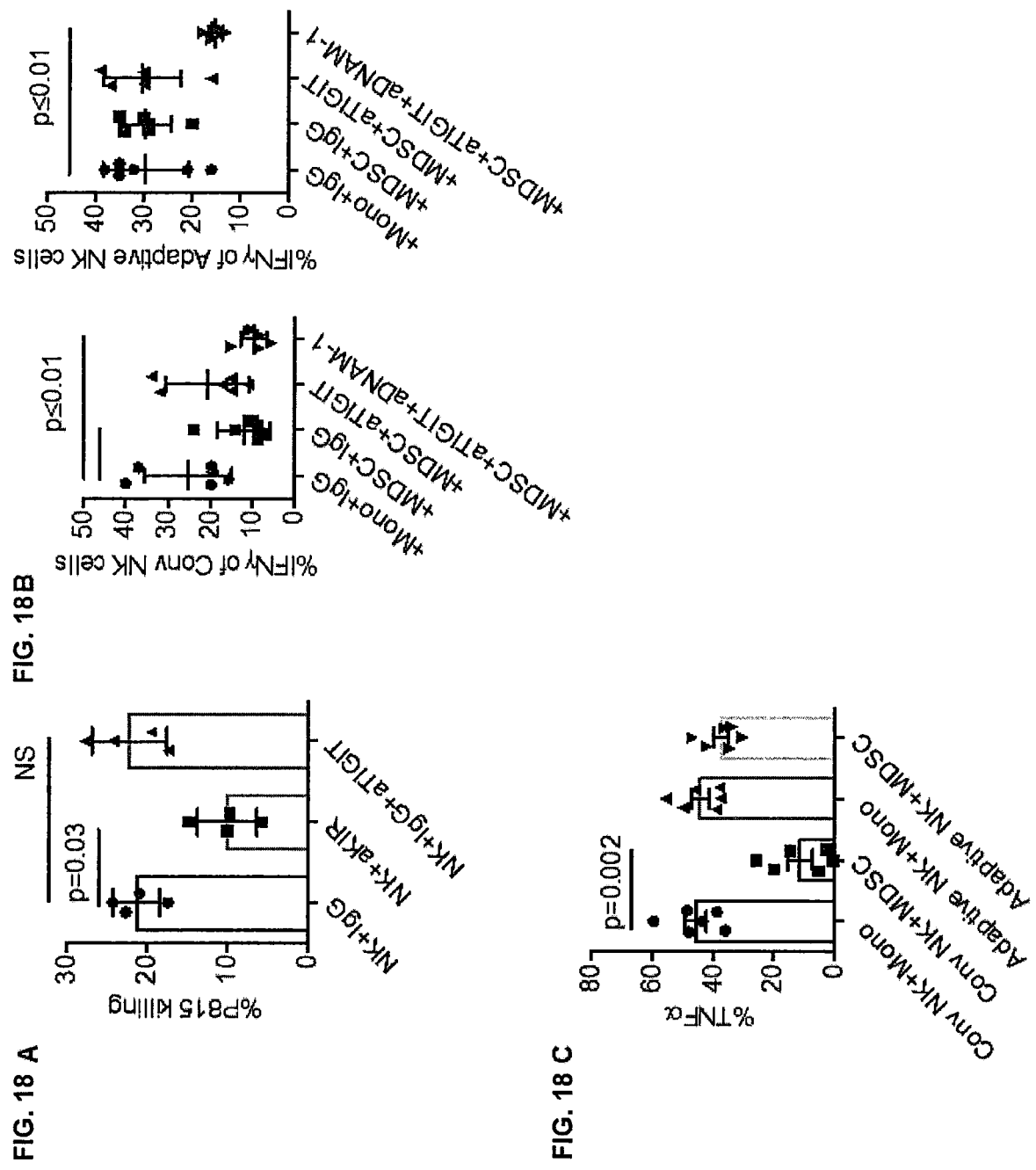

FIG. 21A
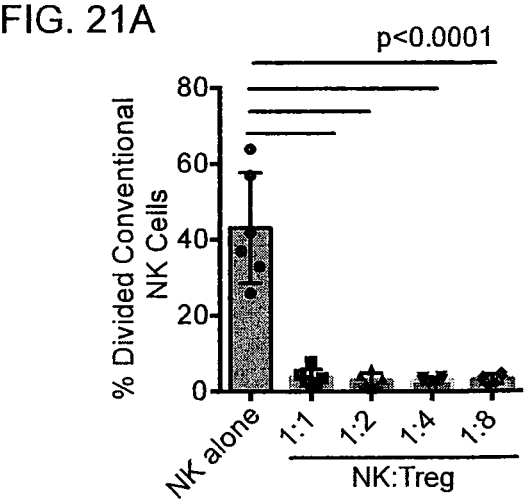
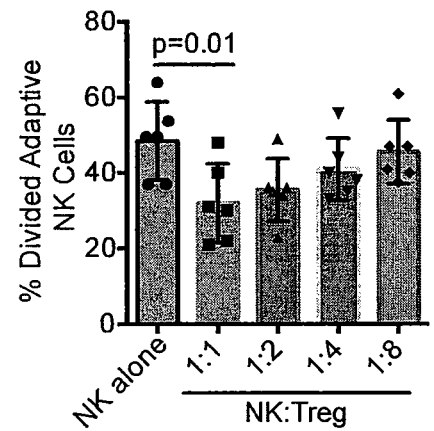
FIG. 21B
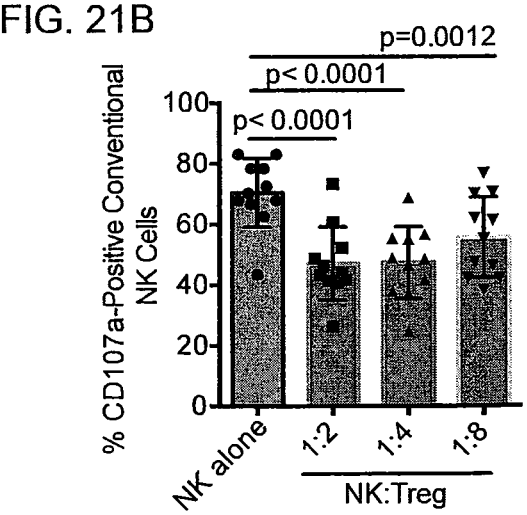
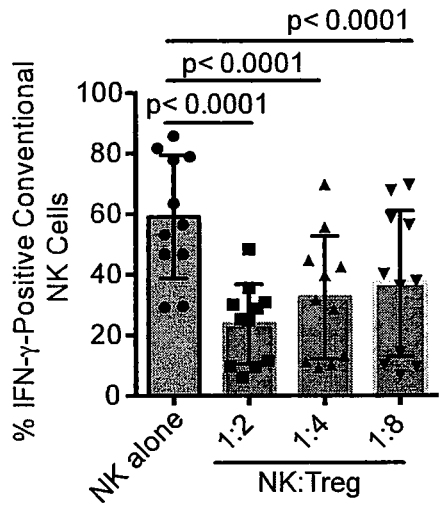
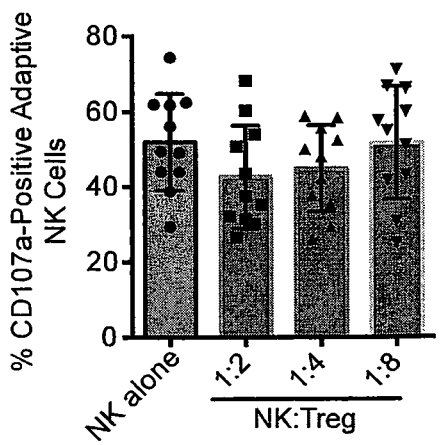
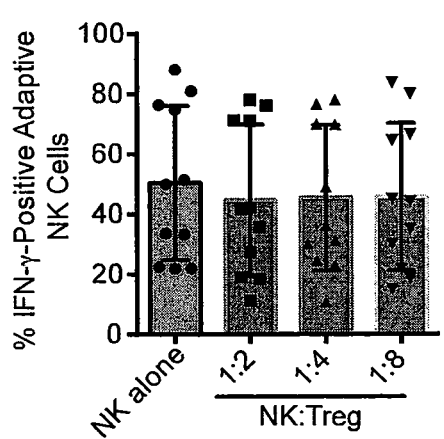

NK CELLS EXHIBITING AN ADAPTIVE PHENOTYPE AND METHODS FOR PREPARING AND FOR USING

CROSS-REFERENCE TO RELATED PATENT APPLICATIONS

This application is a U.S. National Phase Application under 35 U.S.C. § 371 of International Patent Application No. PCT/US2016/051685, filed Sep. 14, 2016, and claims the benefit of priority under 35 U.S.C. Section 119(e) of U.S. Application Ser. No. 62/218,366, filed Sep. 14, 2015; U.S. Application Ser. No. 62/295,708, filed Feb. 16, 2016, all of which are incorporated by reference in their entireties. The International Application was published on Mar. 23, 2017 as International Publication No. WO 2017/048809 A1.

GOVERNMENT FUNDING

This invention was made with government support under CA065493, CA111412, CA197292, and HL122216 awarded by the National Institutes of Health. The government has certain rights in the invention.

SUMMARY OF THE INVENTION

This disclosure describes an NK cell exhibiting an adaptive phenotype, a composition including an adaptive NK cell, an isolated population of adaptive NK cells, and methods of making and using the composition and isolated population. Because an adaptive NK cell has a functionally distinct capability compared to a conventional NK cell that permits the adaptive NK cell to provide additional anti-tumor or anti-virus capabilities when compared to a conventional NK cell, the described compositions, populations, and methods of making and using those compositions and populations may be used for the treatment or prevention of a cancer, a precancerous condition, or a viral infection.

In one aspect, this disclosure describes a composition including an adaptive NK cell. An adaptive NK cell has a functionally distinct capability compared to a conventional NK cell and can provide additional anti-tumor or anti-virus capabilities when compared to a conventional NK cell.

In some embodiments, the adaptive NK cell is $CD3^-$, $CD56^+$, and at least one of $CD57^+$, $NKG2C^+$, $SYK^-$, $Fc\varepsilon R\gamma^-$, $EAT-2^-$, $CD56^{dim}$, $TIGIT^{low}$, $CD45RO^+$, and $CD45RA^-$. In some embodiments, the adaptive NK cell is long-lived. In some embodiments, the adaptive NK cell is at least two of $CD57^+$, $NKG2C^+$, $SYK^-$, $Fc\varepsilon R\gamma^-$, $EAT-2^-$, $CD56^{dim}$, $TIGIT^{low}$, $CD45RO^+$, and $CD45RA^-$. For example, the adaptive NK cell can be $CD57^+$ and $NKG2C^+$. In some embodiments, the adaptive NK cell is at least three of $CD57^+$, $NKG2C^+$, $SYK^-$, $Fc\varepsilon R\gamma^-$, $EAT-2^-$, $CD56^{dim}$, $TIGIT^{low}$, $CD45RO^+$, and $CD45RA^-$. For example, the adaptive NK cell can be $SYK^-$, $Fc\varepsilon R\gamma^-$, and EAT-2.

In some embodiments, expression of the promyelocytic leukemia zinc finger (PLZF) transcription factor is decreased in an adaptive NK cell compared to a conventional NK cell. For example, the PLZF expression can be decreased by at least 90%. In some embodiments, the adaptive NK cell does not express the transcription factor promyelocytic leukemia zinc finger (PLZF).

In some embodiments, the adaptive NK cell demonstrates anti-tumor activity. The tumor can include a tumor of a hematopoietic and/or lymphoid tissue. The tumor can be a solid tumor.

In some embodiments, the adaptive NK cell is derived from a cell cultured in a culture medium comprising at least one of IL-15, IL-21, IL-18, IL-12, IL-2, IFN-α, or IFN-β; from a cell cultured in a culture medium comprising rapamycin; from a cell cultured in a culture medium comprising a Notch ligand; and/or from a cell cultured in a culture medium comprising an NKG2C receptor agonist.

In some embodiments, the adaptive NK cell is prepared in vivo. In some embodiments, the preparation includes administering a cytomegalovirus (CMV) vaccine to a subject, administering inactivated cytomegalovirus (CMV) to a subject, administering a cytokine to a subject, and/or administering a Notch ligand to a subject. The cytokine can include, for example, at least one of IL-15, IL-21, IL-12, IL-18, and GM-CSF. In some embodiments, the cytokine or combination or cytokines may be administered in high doses. In some embodiments, the preparation comprises inducing expression of a Notch ligand in a subject. In some embodiments, the subject is CMV seropositive.

This disclosure also describes a method for treating or preventing cancer, a precancerous condition, or a virus in a subject where the method includes administering to the subject a composition comprising an adaptive NK cell. In some embodiments, the cancer includes bone cancer, brain cancer, breast cancer, cervical cancer, ovarian cancer, cancer of the larynx, lung cancer, pancreatic cancer, prostate cancer, skin cancer, cancer of the spine, stomach cancer, uterine cancer, hematopoietic cancer, or lymphoid cancer. In some embodiments, the cancer is a metastatic cancer.

Also described by this disclosure is a method of inhibiting the growth of a tumor in a subject. The method includes administering to the subject a composition comprising an adaptive NK. In some embodiments, the tumor comprises a solid tumor. In some embodiments, the virus comprises a lentivirus or a herpes virus. In some embodiments, the composition further includes a pharmaceutically acceptable carrier.

This disclosure also describes a method for treating or preventing cancer or a precancerous condition in a subject where the method includes the in vivo preparation of an adaptive NK cell. In some embodiments, the cancer includes bone cancer, brain cancer, breast cancer, cervical cancer, ovarian cancer, cancer of the larynx, lung cancer, pancreatic cancer, prostate cancer, skin cancer, cancer of the spine, stomach cancer, uterine cancer, hematopoietic cancer, or lymphoid cancer. In some embodiments, the cancer is a metastatic cancer.

This disclosure also describes a method of inhibiting the growth of a tumor in a subject, the method including the in vivo preparation of an adaptive NK cell. In some embodiments, the tumor includes a solid tumor. In some embodiments the method further includes administering a composition comprising a therapeutic agent. In some embodiments, the therapeutic agent can be non-naturally occurring and/or can be administered in amount that is not naturally occurring. The therapeutic agent can include, for example, at least one of a cytokine, a chemokine, a therapeutic antibody, an adjuvant, an antioxidant, or a chemotherapeutic agent.

This disclosure further describes a method of preparing an adaptive NK cell. In some embodiments, the adaptive NK cell is prepared in vitro. In some embodiments, the adaptive NK cell is derived from a cell from a cytomegalovirus (CMV) naïve source, from a cell isolated from blood, from a pluripotent stem cell, from an embryonic stem cell, from a cell isolated from umbilical cord blood, and/or from an induced pluripotent stem cell (iPSC).

In a further aspect this disclosure describes methods to obtain an adaptive NK cell. The method includes obtaining a blood sample from a subject and culturing a population of NK cells of the blood sample. In some embodiments, the population of NK cells is cultured in a culture medium that includes one or more of IL-15, IL-21, and a Notch ligand. In some embodiments, the population of NK cells is cultured with a CMV peptide-supplemented mature dendritic cell. In some embodiments, the population of NK cells is cultured with autologous monocytes and IL-15. In some embodiments, the adaptive NK cell is $CD56^{dim}$ and is one or more of $NKG2C^+$ and $TIGIT^{low}$.

In another aspect this disclosure describes a composition that includes an adaptive NK cell obtained by the methods described herein. In a further aspect, this disclosure describes the composition includes a population of NK cells is enriched for an adaptive NK cell obtained by the methods described herein.

In another aspect, this disclosure describes an isolated population of NK cells wherein the cells are $CD56^{dim}$, and one or more of $NKG2C^+$, $CD57^+$, and $TIGIT^{low}$. In a further aspect, this disclosure describes an isolated population of NK cells, wherein the isolated population is enriched for an NK cell that is $CD56^{dim}$ and $NKG2C^+$. This disclosure also describes compositions including the isolated populations described herein.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

The terms "comprises" and variations thereof do not have a limiting meaning where these terms appear in the description and claims.

Unless otherwise specified, "a," "an," "the," and "at least one" are used interchangeably and mean one or more than one.

Also herein, the recitations of numerical ranges by endpoints include all numbers subsumed within that range (e.g., 1 to 5 includes 1, 1.5, 2, 2.75, 3, 3.80, 4, 5, etc.).

For any method disclosed herein that includes discrete steps, the steps may be conducted in any feasible order. And, as appropriate, any combination of two or more steps may be conducted simultaneously.

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

BRIEF DESCRIPTION OF THE FIGURES

FIG. 1(A-D) shows cytomegalovirus (CMV) reactivation is associated with reduced relapse risk and superior disease-free survival in reduced-intensity conditioning (RIC) but not myeloablative (MA) hematopoietic stem cell (HCT) recipients. Kaplan-Meier curves of relapse rates (FIG. 1A) and disease-free survival (DFS) (FIG. 1B) stratified by CMV status in RIC recipients. Relapse rates (FIG. 1C) and DFS (FIG. 1D) stratified by CMV status in MA recipients. Dashed lines represent trends calculated for CMV seronegative recipients. Dotted lines represent trends calculated for CMV seropositive recipients that did not experience viral reactivation. Solid lines represent trends calculated for CMV seropositive recipients that experienced viral reactivation. p values shown in each plot were calculated for trends.

FIG. 4(A-B) shows $CD56^{dim}CD57^+$ $NKG2C^+$ NK cells produce TNF and IFN-γ at high frequencies compared to other NK cell subsets. PBMCs from CMV seropositive donors were cultured with or without K562 target cells at a 2:1 ratio, and functional responses were analyzed in subsets of $CD56^{dim}$ NK cells.

FIG. 6(A-B) shows the transcription factor promyelocytic leukemia zinc finger (PLZF) is downregulated in $CD56^{dim}SYK^-$ NK cells cultured with IL-21.

FIG. 7(A-D) shows rapamycin promotes adaptive NK cell differentiation and enhances NK cell function. CD3/CD19-depleted PBMCs from healthy CMV seropositive donors were cultured for 4 days with DMSO or 10 micromolar (µM) rapamycin.

FIG. 9(A-B) shows myeloid-derived suppressor cells (MDSCs) suppress T and NK cell proliferation and NK cell functions.

FIG. 13(A-D) shows reactive oxygen species (ROS) induce CD155 expression on MDSCs. MDSCs were induced from healthy blood donor PBMC with IL-6 (10 ng/mL) and GM-CSF (10 ng/mL) for 7 days, bead-depleted for HLA-DR, and enriched for CD33. FIG. 13A. MDSCs and freshly isolated monocytes were stained for the antigens shown. One representative example from 10 independent experiments is shown. FIG. 13B. Induced MDSCs were stained for CD155 and analyzed by flow cytometry following overnight treatment with superoxide dismutase (SOD, 200 IU/mL), arginase inhibitor (a-ARG, arginase inhibitor N(ω)-hydroxy-nor-L-arginine, 500 µM), ROS scavenger (Catalase, 200 international units per milliliter (IU/mL)), blocking antibodies against TGF-β (10 µm/mL), iNOS inhibitor (aiNOS, NG-monomethyl-1-arginine, 500 micromolar (µM)), or left untreated. Pooled (n=4) data is shown as mean±SEM, and statistical analysis were done using the Student's t-test. FIG. 13C. Unstimulated monocytes and MDSCs were stained for total ROS and analyzed by flow cytometry. FIG. 13D. Unstimulated or $H_2O_2$ (250 µM) monocytes and unstimulated MDSCs were stained for total ROS, CD112, and CD155 and analyzed by flow cytometry. Cells double positive for ROS and CD112 or CD155 are shown. One representative donor of six is shown. One representative isotype control is shown for all groups for simplicity as individual controls were similar between conditions.

FIG. 14(A-C) shows TIGIT engagement inhibits pZAP70/Syk and pERK1/2 and results in inhibition of NK cell cytotoxicity. Purified NK cells from healthy blood donors were co-cultured with autologous MDSCs or freshly isolated monocytes at a 2:1 ratio in the presence of IL-15 (10 ng/mL) and in the presence or absence of blocking antibodies against TIGIT (10 µg/mL), or catalase (200 IU/mL) for 5 days. Cells were then washed, rested for 4 hours, stimulated for 10 and 30 min with anti-CD16, and stained for pZAP/Syk or pERK1/2 respectively. Representative (FIG. 14A) or cumulative (FIG. 14B) data are shown from 3 independent experiments as mean±SEM. Statistical analysis was done using the Student's t-test. FIG. 14C. NK cells from monocyte and MDSC co-cultures in the presence or absence of anti-TIGIT or catalase were washed and incubated with $^{51}$Cr-labeled K562 for 4 hours to assess NK cell cytotoxicity. Representative data from 3 independent experiments is shown as mean±SEM.

FIG. 15(A-F) shows TIGIT-dependent suppression of conventional NK cells by myelodysplastic syndrome (MDS) MDSCs.

FIG. 17(A-B) shows the gating strategies used in Example 7. FIG. 17A. Gating strategy for adaptive and conventional NK cells in healthy blood donors. FIG. 17B. Gating strategy for adaptive and conventional NK cells in MDS patients. Cell percentages presented in the plots represents frequency of conventional and adaptive NK cells of total NK cells.

FIG. 18(A-C) shows NK cell function was not affected in the presence of anti-TIGIT. FIG. 18A. Healthy donor polyclonal-NK (n=4) cell cytotoxicity was analyzed by $^{51}$Cr release assays (4 hours) against p815 in the presence of anti-TIGIT (10 ug/ml) or an agonistic anti-CD158b (10 ug/ml). Accumulated data are shown as mean±SD and statistical analysis were done on pooled data using the Mann-Whitney test. FIG. 18B. NK cells were cultured with monocytes or MDSCs in the presence of IL-15 and IgG (10 ug/ml) or blocking antibodies against TIGIT (10 ug/ml) for 5 days, alternatively, cells were co-blocked by anti-TIGIT and anti-DNAM-1 (10 ug/ml) (n=6). Pooled data are shown as mean±SEM, and the One-way ANOVA was used for statistical analysis. FIG. 18C. Purified NK cells (n=6) from healthy blood donors were co-cultured with autologous monocytes or allogeneic MDSCs enriched from the blood of MDS-patients at a 2:1 ratio in the presence of IL-15 (10 ng/ml) for 5 days. Following 6 hours stimulation by anti-CD16, TNFα-production was evaluated in conventional and adaptive NK cells by flow cytometry. Representative data are shown as mean±SD and statistical analyses were done on pooled data using the Mann-Whitney test.

FIG. 21(A-C) shows adaptive NK cells are resistant to Treg-mediated suppression. CellTrace-labeled CD56$^+$ NK cells from 12 CMV seropositive donors were cultured alone or co-cultured with Tregs at the indicated ratios for 6 days. FIG. 21A. FACS was used to analyze proliferation of conventional (CD56$^+$CD57$^+$FcεRγ$^+$ NKG2C$^-$) and adaptive (CD56$^+$CD57$^+$FcεRγ$^-$ NKG2C$^+$) NK cell subsets. Shown are the percentages of NK cells that exhibited CellTrace dye dilution in each culture condition. FIG. 21B. Degranulation (as measured by CD107a expression) and IFN-γ production was measured by FACS on cultured NK cells following stimulation with anti-CD16 agonist antibody, IL-12 and IL-18.

DETAILED DESCRIPTION OF ILLUSTRATIVE EMBODIMENTS

Figure 2A:
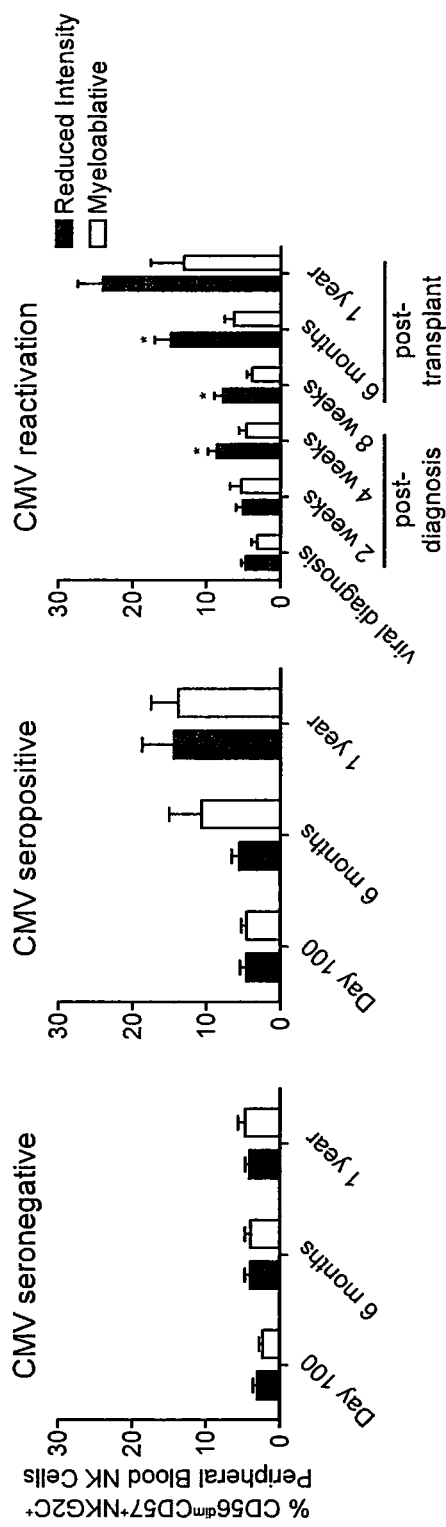
FIG. 2(A-B) shows preferential expansion of $CD56^{dim}CD57^+$ $NKG2C^+$ adaptive NK cells in RIC HCT recipients that experience CMV reactivation. Average percentage (FIG. 2A) and absolute number (cells/µl of blood) (FIG. 2B) of $CD56^+$ NK cells with an adaptive $CD56^{dim}CD57^+$ $NKG2C^+$ phenotype are shown. Values for CMV seronegative recipients at day 100 (RIC n=44, MA n=32), 6 months (RIC n=35, MA n=23), and 1 year (RIC=31, MA=21) post-transplant are shown in the left panels. Values for CMV seropositive recipients without CMV reactivation at day 100 (RIC n=22, MA n=12), 6 months (RIC=13, MA=14) and 1 year (RIC=11, MA=8) post-transplant are shown in the middle panels. Values for CMV seropositive recipients that reactivated CMV at the time of viral diagnosis (RIC n=28, MA n=18), 2 weeks post-diagnosis (RIC n=26, MA n=14), 4 weeks post-diagnosis (RIC n=29, MA=23), 8 weeks post-diagnosis (RIC n=24, MA n=15), 6 months post-transplant (RIC n=29, MA n=17) and 1 year post transplant (RIC n=26, MA n=10) are shown in the right panels. *=p≤0.05 comparing RIC to MA. Error bars represent standard error of the mean (SEM).

This disclosure provides an NK cell exhibiting an adaptive phenotype, an isolated population of adaptive Natural Killer (NK) cells; a composition including an adaptive NK cell; methods for preparing or producing of an adaptive NK cell, a population of adaptive NK cells, or a composition including an adaptive NK cell in vitro and/or in vivo; and methods for the use of an adaptive NK cell, a population of adaptive NK cells, or a composition including an adaptive NK cell. In some embodiments, the adaptive NK cells may be used to treat a viral infection, a cancer, and/or a tumor.

In some embodiments, the preparation of an adaptive NK cell includes isolation of a cell or a population of cells. In some embodiments, the preparation includes differentiation and/or expansion of a cell.

As used herein, the term "NK cell" refers to a cell that is both CD56$^+$ and CD3$^-$. Natural killer (NK) cells are cytokine-producing, cytotoxic lymphocytes that have essential roles in immunity against viral infections and tumors. As used herein, a "canonical NK cell," also termed a "conventional NK cell," refers to an NK cell that is SYK$^+$, EAT-2$^+$, FcεRγ$^+$, PLZF$^+$. In some embodiments, a conventional NK cell is NKG2C$^-$. In some embodiments, a conventional NK cell is CD57$^-$. In some embodiments, an adaptive NK can be an NK cell that exhibits decreased expression or loss of expression of one or more of SYK, EAT-2, FcεRγ, and PLZF.

An adaptive NK cell has a functionally distinct capability compared to a conventional NK cell. These differences in function permit an adaptive NK cell to provide additional anti-tumor or anti-virus capabilities when compared to a conventional NK cell. An adaptive NK cell may belong to one of several unique subsets that are distinguished from a conventional NK cell. As described further below, an adaptive NK cell can, for example, express CD57, a marker of terminal differentiation on human CD8$^+$ T cells; exhibit transcriptional silencing of the gene encoding the transcription factor promyelocytic leukemia zinc finger (PLZF) relative to the level of PLZF expressed by a conventional NK cell; exhibit enhanced function when triggered by the low affinity Fc receptor CD16; exhibit transcriptional silencing of one or more of the genes encoding SYK, EAT-2, and FcεRγ; express NKG2C$^+$; express CD45RO; exhibit low or no expression of CD45RA; be long-lived; exhibit a memory cell phenotype; exhibit enhanced anti-tumor activity compared to a conventional NK cell; and/or exhibit enhanced anti-virus activity compared to a conventional NK cell.

In some embodiments, the NK cell and/or adaptive NK cell may be a CD56$^{bright}$ NK cell. CD56$^{bright}$ NK cells isolated from the peripheral blood proliferate rapidly upon IL-2 or IL-15 stimulation, produce high levels of interferon (IFN)-γ in response to IL-12 and IL-18 stimulation, express high levels of the inhibitory receptor NKG2A, and lack expression of the low affinity Fc receptor CD16 and killer immunoglobulin like receptors (KIR). CD56$^{bright}$ NK cells have limited cytotoxic potential, as they express very low levels of perforin and granzymes. While they comprise a minor fraction of total peripheral blood NK cells, CD56$^{bright}$ NK cells are significantly enriched in secondary lymphoid tissues where they are presumed to differentiate into CD56$^{dim}$ NK cells.

In other embodiments, the NK cell and/or adaptive NK cell may be a CD56$^{dim}$ NK cell. Canonical CD56$^{dim}$ NK cells represent a phenotypically diverse subset of NK cells that express very high levels of perforin and granzymes and readily degranulate in response to virally infected cells, neoplastic cells and autologous, activated immune cells. Canonical CD56$^{dim}$ NK cells are strong mediators of antibody-dependent cellular cytotoxicity (ADCC) due to high expression levels of CD16 and can be readily stimulated through activating KIR. Degranulation by canonical CD56$^{dim}$ NK cells is potentiated by the expression of educating inhibitory KIR that recognize self-MHC class I molecules. As such, canonical CD56$^{dim}$ NK cells can efficiently mediate cytotoxic immunoregulation of activated lymphocytes and early immunosurveillance of infected or transformed cells. Compared to CD56$^{bright}$ NK cells, canonical CD56$^{dim}$ NK cells produce less IFN-γ in response to IL-12 and IL-18.

CMV Seropositivity and Reactivation

Cytomegalovirus (CMV) is a β-herpesvirus that is generally acquired early in life and establishes a persistent, lifelong infection. CMV seroprevalence is ~50% among U.S. adults, and infections are generally asymptomatic as they are well controlled by CD8$^+$ T cells and NK cells in healthy individuals. CMV seropositivity is associated with an increased proportion of NK cells that express the heterodimeric activating receptor CD94-NKG2C and with an increase in NKG2C$^{high}$CD57$^+$ NK cells in healthy adults (Lopez-Verges et al., Proc Natl Acad Sci USA. 2011; 108 (36):14725-14732). Individuals who have not been exposed to CMV are CMV "naïve."

After a primary infection, CMV is typically not eradicated but establishes life-long infection in its host. CMV is dispersed and becomes dormant in multiple end organs but can later be reactivated by a number of different stimuli, including, for example, immunosuppression and inflammation.

As shown in Example 1 and FIG. 1, CMV reactivation is associated with reduced leukemia relapse and improved disease-free survival in patients with a hematologic malignancy treated with reduced-intensity conditioning (RIC) and hematopoietic stem cell transplantation (HCT) (a regimen known to lead to relapse rates of 30-40%). Example 1 and FIG. 2 establish a novel link between CMV reactivation and adaptive NK cell expansion in vivo, especially in patients receiving RIC.

Adaptive NK Cells

As used herein, an "adaptive NK cell" includes a single adaptive NK cell, more than one adaptive NK cell, and/or an isolated population of cells including adaptive NK cells.

In some embodiments, an adaptive NK cell is CD57+. On average, 40% of CD56$^{dim}$ NK cells from adults express CD57, with a significant variation between individuals ranging from 5% to 70%. The vast majority of NK cells expressing perforin are CD57+. Functionally, CD56$^{dim}$CD57+ NK cells proliferate poorly compared to CD56$^{dim}$CD57- NK cells in response to IL-2 or IL-15 and are less responsive to stimulation by IL-12 and IL-18 (Bjorkstrom et al., *Blood.* 2010; 116(19):3853-3864). However, CD56$^{dim}$CD57+ NK cells produce more IFN-γ and demonstrate more potent lytic activity when stimulated through CD16 (Lopez-Verges et al., *Blood.* 2010; 116(19): 3865-3874). As described herein, CD57 can be a marker of terminally differentiated canonical NK cells that exhibit robust cytotoxicity and inflammatory cytokine production in response to triggering through activating receptors.

In some embodiments, an adaptive NK cell is NKG2C+. In some embodiments, the adaptive NK cell is SYK-, FcεRγ-, EAT-2-, CD45RO+, CD45RA-, and/or TIGIT$^{low}$. In some embodiments, the adaptive NK cell is TIGIT-.

In some embodiments, the adaptive NK cell is at least two of CD57+, NKG2C+, SYK-, FcεRγ-, EAT-2-, CD56$^{dim}$, TIGIT$^{low}$, CD45RO+, and CD45RA-. In some embodiments, the adaptive NK cell is long-lived. For example, the adaptive NK cell can be CD57+ and NKG2C+ or CD56$^{dim}$ and TIGIT$^{low}$ or CD56$^{dim}$ and NKG2C+. In some embodiments, the adaptive NK cells are at least three of CD57+, NKG2C+, SYK-, FcεRγ-, EAT-2-, CD56$^{dim}$, TIGIT$^{low}$, CD45RO+, and CD45RA-. For example, the adaptive NK cell can be SYK-, FcεRγ-, and EAT-2- or CD56$^{dim}$, NKG2C+, and TIGIT$^{low}$.

In some embodiments, expression of the promyelocytic leukemia zinc finger (PLZF) transcription factor is decreased in an adaptive NK cell compared to a canonical NK cell. In some embodiments, expression of the promyelocytic leukemia zinc finger (PLZF) transcription factor is decreased by at least 20%, at least 30%, at least 40%, at least 50%, at least 60%, at least 70%, at least 80%, at least 90%, or at least 95% in an adaptive NK cell compared to a canonical NK cell. In some embodiments, the adaptive NK cell does not express PLZF. In some embodiments, not expressing a marker or protein is preferably defined as having a level of expression of the marker or protein that is not detectable using FACS, and being positive for or expressing a marker or a protein is defined as having a level of expression of the marker or protein that is detectable using FACS.

In some embodiments, expression of PD-1 is decreased in an adaptive NK cell compared to a canonical NK cell. In some embodiments, expression of PD-1 is decreased by at least 20%, at least 30%, at least 40%, at least 50%, at least 60%, at least 70%, at least 80%, at least 90%, or at least 95% in an adaptive NK cell compared to a canonical NK cell. In some embodiments, the decreased level of PD-1 (an inhibitory receptor) allows an adaptive NK cells to resist PDL1, which is expressed by many tumor cells.

In some embodiments, expression of TIGIT is decreased in an adaptive NK cell compared to a canonical NK cell. In some embodiments, expression of TIGIT is decreased by at least 20%, at least 30%, at least 40%, at least 50%, at least 60%, at least 70%, at least 80%, at least 90%, or at least 95% in an adaptive NK cell compared to a canonical NK cell.

In some embodiments, expression of PLZF, PD-1, and TIGIT is decreased in an adaptive NK cell compared to a canonical NK cell.

In some embodiments, the adaptive NK cell has anti-tumor activity. In some embodiments, the tumor is a tumor of a hematopoietic and/or lymphoid tissue. In some embodiments, the tumor is a solid tumor.

In some embodiments, the adaptive NK cell expresses the cell cytotoxicity receptor 2B4, the low affinity Fc receptor CD16, and/or a killer immunoglobulin like receptor (KIR). In some embodiments the adaptive NK cell lacks expression of the inhibitory receptor NKG2A. In some embodiments, the adaptive NK cell expresses high levels of granzyme and/or perforin and exhibits a capacity to degranulate in response to virally infected cells, neoplastic cells and/or autologous, activated immune cells.

In some embodiments, the adaptive NK cell is long-lived NK cell and/or is a memory NK cell. In some embodiments, a long-lived NK cell persists at least 21 days, at least 30 days, at least 60 days, at least 80 days, or at least 100 days after infection. In comparison, a canonical NK cell typically exhibits lower persistency, usually less than 7 to 14 days.

In some embodiments, the adaptive NK cell has enhanced anti-tumor immune activity compared to a canonical NK cell. In some embodiments, the adaptive NK cell has an enhanced ability to overcome an MDSC-induced suppression of an immune response compared to a canonical NK cell. In some embodiments, an adaptive NK cell exhibits an enhanced ability to overcome MDSC-induced suppression when, in the presence of an MDSC, the adaptive NK cell exhibits enhanced proliferation compared to a canonical NK in the presence of an MDSC.

In some embodiments, the adaptive NK cell has an enhanced ability to overcome a regulatory T cell (Treg)-induced suppression of an immune response compared to a canonical NK cell. In some embodiments, an adaptive NK cell exhibits an enhanced ability to overcome Treg-induced suppression when, in the presence of a Treg, the adaptive NK cell exhibits enhanced degranulation (e.g., as measured by CD107a expression) and/or IFN-γ production compared to a canonical NK in the presence of a Treg.

In some embodiments, the adaptive NK cell can be included in a population of cells including, for example, an isolated population of cells and/or a population of NK cells. In some embodiments, a population of cells is considered "enriched" for an adaptive NK cell when the population of cells includes at least 10% adaptive NK cells, at least 20% adaptive NK cells, at least 30% adaptive NK cells, at least 40% adaptive NK cells, at least 50% adaptive NK cells, at least 60% adaptive NK cells, at least 70% adaptive NK cells, at least 80% adaptive NK cells, at least 90% adaptive NK cells, or at least 95% adaptive NK cells.

In Vitro Preparation of an Adaptive NK Cell

In some embodiments, the production and/or preparation of an adaptive NK cell is in vitro. The in vitro preparation may include cell differentiation, expansion, enrichment, and/or isolation.

In some embodiments, an adaptive NK cell may be prepared from a blood sample from a subject or from a population of cells isolated from the blood sample. In some embodiments, a method for preparing and/or producing an adaptive NK cell includes obtaining a blood sample from a subject and culturing a population of NK cells of the blood sample. In some embodiments, the population of NK cells from the blood sample is isolated prior to culturing the population of NK cells. In some embodiments, the population of NK cells of the blood sample can be cultured in culture medium; cultured with a dendritic cell including, for example, a mature dendritic cell, a CMV peptide-supplemented mature dendritic cell, or both; and/or cultured with a monocyte.

In some embodiments, an adaptive NK cell may be prepared from a cytomegalovirus (CMV) naïve and/or CMV seronegative source. For example, an adaptive NK cell may be prepared from a cell isolated from the blood of a CMV seronegative donor.

In some embodiments, an adaptive NK cell may be prepared from a CMV seropositive source. For example, an adaptive NK cell may be prepared from a cell isolated from the blood of a CMV seropositive donor or a population of cells isolated from the blood of a CMV seropositive donor. In some embodiments, a method for preparing and/or producing an adaptive NK cell that includes obtaining a blood sample from a subject can further include administering a cytomegalovirus (CMV) vaccine to the subject.

In some embodiments, an adaptive NK cell may be prepared from a pluripotent stem cell, from an embryonic stem cell, from a cell isolated from umbilical cord blood, from an induced pluripotent stem cell (iPSC), from hemogenic endothelium, from a hematopoietic stem or progenitor cell, from an iPSC-derived hematopoietic stem cell, from a hematopoietic stem cell derived through trans-differentiation, from a canonical NK cell, and/or from an NK cell progenitor.

In some embodiments, a method for preparing and/or producing an adaptive NK cell includes culturing a cell or a population of cells including, for example, a population of NK cells in a culture medium. In some embodiments, an adaptive NK cell is derived from a cell cultured in a culture medium.

In some embodiments, the culture medium includes one or more cytokines. The culture medium can include, for example, IL-15, IL-21, IL-18, IL-12, IL-2, IFN-α, or IFN-β, or combinations thereof. In some embodiments, the cytokine may be membrane-bound as described, for example, in Denman et al., *PLOS One*. 2012 7(1):e.30264. In some embodiments, the culture medium can include a Notch ligand. In some embodiments, the cell culture medium includes rapamycin. In some embodiments, the cell culture medium is feeder-free. In some embodiments, the cell culture medium includes an activator of CD16 signaling including, for example, an anti-CD16 antibody, a ligand of an Fc receptor, a ligand of CD16, a bi-specific killer cell engager (BiKE), and/or a tri-specific killer engager (TriKE).

In some embodiments, the culture medium can include a TIGIT inhibitor, a TIGIT blocker, a TIGIT antagonist, a TIGIT ligand blocker, and/or a TIGIT ligand antagonist. In some embodiments, a TIGIT inhibitor includes an antibody against TIGIT. In some embodiments, a TIGIT ligand may, include, for example, CD155 or CD112. In some embodiments, the blocker or antagonist may include, for example, a blocking antibody. In some embodiments, the culture medium can include an inhibitor of the production of reactive oxygen species (ROS) including, for example, a catalase. As shown in Example 7, blocking TIGIT or inhibiting ROS can increase the signaling cascades that activate NK cell cytotoxicity.

In some embodiments, the method for preparing an adaptive NK cell includes contacting the NK cells of the blood sample with a TIGIT inhibitor, a PLZF inhibitor, and/or a PD-1 inhibitor. In some embodiments, the TIGIT inhibitor includes an antibody against TIGIT.

In some embodiments, the method for preparing an adaptive NK cell includes suppressing the expression of PLZF, TIGIT, and/or PD-1 in the NK cells of the blood sample or in the adaptive NK cell. In some embodiments, the expression may be suppressed by genetic knockdown of a nucleic acid encoding PLZF, TIGIT, and/or PD-1. In some embodiments, the expression may be suppressed by the use of siRNA.

In some embodiments, including, for example, where a method for preparing and/or producing an adaptive NK cell includes obtaining a blood sample from a subject and culturing a population of NK cells of the blood sample, the adaptive NK cell may have altered features or functions compared to the population of NK cells prior to culture. For example, the adaptive NK cell can have an enhanced anti-tumor immune activity compared to the population of NK cells prior to culture. The enhanced anti-tumor immune activity can include, for example, one or more of increased cytotoxicity, increased cytokine production, and increased resistance to T regulatory (Treg) cells. In some embodiments, the adaptive NK cell can have one or more of increased cytotoxicity; increased cytokine production; increased persistence in vivo and/or in vitro; and increased resistance to T regulatory cells compared to the population of NK cells prior to culture. In some embodiments, the adaptive NK cell can have reduced expression of PLZF, TIGIT, and/or PD-1 compared to the population of NK cells prior to culture.

In some embodiments, the adaptive NK cell can have an enhanced ability to overcome MDSC-induced suppression of an immune response compared to the population of NK cells prior to culture. In some embodiments, an adaptive NK cell exhibits an enhanced ability to overcome MDSC-induced suppression when, in the presence of an MDSC, the adaptive NK cell exhibits enhanced proliferation compared to an NK cell of the population of NK cells prior to culture in the presence of an MDSC.

In some embodiments, the adaptive NK cell has an enhanced ability to overcome a regulatory T cell (Treg)-induced suppression of an immune response compared to the population of NK cells prior to culture. In some embodiments, an adaptive NK cell exhibits an enhanced ability to overcome Treg-induced suppression when, in the presence of a Treg, the adaptive NK cell exhibits enhanced degranulation (e.g., as measured by CD107a expression) and/or IFN-γ production compared to an NK cell of the population of NK cells prior to culture in the presence of a Treg.

In some embodiments, including, for example, where a method for preparing and/or producing an adaptive NK cell includes obtaining a blood sample from a subject and culturing a population of NK cells of the blood sample, the method may include cell expansion.

In some embodiments, the method for preparing or producing an adaptive NK cell includes isolating the adaptive NK cell. In some embodiments, the NK cell may be isolated using its expression or lack of expression of one or more surface markers. Useful surface markers can include, for example, CD56, CD3, CD57, NKG2C, TIGIT, CD45RO, and CD45RA.

In some embodiments, the method for preparing or producing an adaptive NK cell results in a population of NK cells enriched for an adaptive NK cell. In some embodiments, a population of NK cells is considered "enriched" for an adaptive NK cell when the population of NK cells includes at least 10% adaptive NK cells, at least 20% adaptive NK cells, at least 30% adaptive NK cells, at least 40% adaptive NK cells, at least 50% adaptive NK cells, at least 60% adaptive NK cells, at least 70% adaptive NK cells, at least 80% adaptive NK cells, at least 90% adaptive NK cells, or at least 95% adaptive NK cells. In some embodiments, a method for preparing or producing an adaptive NK cell from a population of NK cells results in a population "enriched" for an adaptive NK cell when the population of NK cells after performing the method includes a greater proportion of adaptive NK cells than the proportion of NK cells found before the method was performed. In some embodiments, a method of preparing and/or producing an adaptive NK cell that includes obtaining a blood sample from a subject and culturing a population of NK cells of the blood sample results in a population "enriched" for an adaptive NK cell when the population of NK cells after performing the method includes a greater proportion of adaptive NK cells than the proportion of NK cells found in the population of NK cells of the blood sample.

In some embodiments, the adaptive NK cell is derived from a cell co-cultured with a feeder cell. In some embodiments, the adaptive NK cell is derived from a cell cultured in feeder-free cell culture medium. In some embodiments, the feeder cell is an adherent cell. In some embodiments, the feeder cell is an irradiated cell. In some embodiments, the feeder cell is a stromal cell. In some embodiments, the stromal cell may be an OP9 cell. In some embodiments, the feeder cell may express a ligand that stimulates and/or differentiates an adaptive NK cell including, for example, a Notch ligand including, for example, Delta-like 1 (DL-1); a membrane-bound cytokine; a human leukocyte antigen (HLA) class I molecule (either classical or non-classical HLA, such as HLA-E, for example); or combinations thereof.

In some embodiments, the adaptive NK cell is derived from a cell co-cultured with an a monocyte. In some embodiments, a method for preparing and/or producing an adaptive NK cell includes culturing a cell or a population of cells including, for example, a population of NK cells with a monocyte. In some embodiments, a monocyte includes a $CD14^+$ monocyte, a macrophage; a dendritic cell including, for example, a mature dendritic cells; an antigen presenting cell; and/or another myeloid cell. In some embodiments, the monocyte may present an antigen including, for example, an antigen derived from CMV. In some embodiments, the antigen is preferably a CMV peptide. In some embodiments, the culture medium can include a cytokine to stimulate an antigen presenting cell and/or a monocyte including, for example, an inflammatory cytokine or GM-CSF, or both. In some embodiments, the culture medium can include a cytokine to induce maturation of the monocyte including, for example IL-15. In some embodiments, the monocyte can be an autologous monocyte.

In some embodiments, the adaptive NK cell is derived from a cell cultured in a culture medium comprising an agonist of one or more activating receptors including, but not limited to, CD16, NKG2C, DNAM-1, and 2B4. In some embodiments, an agonist can be a single monoclonal antibody or a combination of monoclonal or polyclonal antibodies that stimulate one or more activating receptors. In some embodiments, an agonist can be the natural ligand of the receptor. In some embodiments, the adaptive NK cell is derived from a cell cultured with a stimulator of an activating receptor including, for example, HLA-E, the natural ligand for the NKG2C receptor. In some embodiments, the adaptive NK cell can be cultured according to the culture methods described in WO 2014/037422 for obtaining $NKG2C^+$ NK cells.

As shown in Example 2, in vitro culture of cord blood-derived NK cells on the OP9 delta-like 1 (DL1) stromal cell line with high-dose IL-15 (10 ng/mL) and IL-21 (50 ng/mL) promotes the differentiation and expansion of terminally differentiated cells expressing CD57. Furthermore, these culture conditions support the expansion of cord blood-derived $CD56^+SYK^-PLZF^-$ adaptive NK cells. Thus, a culture system as described herein can be used to drive the maturation and expansion of highly functional subsets of NK cells ex vivo for adoptive transfer into a subject with cancer and/or a viral infection. As shown in Example 1, $CD56^{dim}CD57^+$ $NKG2C^+$ NK cell expansion is associated with reduced leukemia relapse after reduced intensity HCT, supporting the idea that terminal NK cell maturation and adaptive NK cell expansion are associated with anti-tumor effects in vivo.

In some embodiments, the adaptive NK cell is derived from a cell selected for its downregulation or failure to express TIGIT. In some embodiments, a population of cells including an adaptive NK cell may be further enriched for $TIGIT^{low}$ and/or $TIGIT^-$ cells.

In some embodiments, the adaptive NK cell can be derived from a cell cultured with a dendritic cell. In some embodiments, the dendritic cell can be a mature dendritic cell. In some embodiments, the dendritic cell can be cultured with a CMV peptide. In some embodiments, a CMV peptide can include multiple CMV peptides and/or a pool of CMV peptides. For example, as shown in Example 8, adaptive NK cell expansion can be induced by incubating $CD3^-CD56^+$ NK cells and $CD14^+$ monocytes with CMV peptide-supplemented mature dendritic cells.

In some embodiments, the adaptive NK cell can be derived from a cell cultured with a monocyte. In some embodiments, the monocyte can be an autologous monocyte. In some embodiments, the adaptive NK cell can be derived from a cell cultured with a monocyte in the presence of IL-15. For example, as shown in Example 9, NK cells from CMV seropositive donors skew towards a CD45RA− CD45RO+ phenotype when cultured in the presence of autologous monocytes and IL-15.

In Vivo Preparation of an Adaptive NK Cell

In some embodiments, the preparation of an adaptive NK cell is in vivo. An adaptive NK cell prepared in vivo may be used in the same subject in which it is prepared or in a distinct subject, including an allogenic application of the adaptive NK cell preparation. In some embodiments the adaptive NK cell prepared in vivo can be removed from the subject and subsequently readministered to the subject.

In some embodiments, the preparation can include administering a cytomegalovirus (CMV) vaccine, including, for example, an attenuated CMV vaccine, a recombinant CMV vaccine, and/or inactivated CMV to a subject. In some embodiments the subject is CMV seropositive before the administration of the vaccine and/or inactivated CMV.

In some embodiments, the preparation includes administering a cytokine to a subject including, for example, one or more of IL-15, IL-21, IL-18, IL-12, IL-2, IFN-α, IFN-β, and GM-CSF. In some embodiments, the cytokine may be membrane-bound. In some embodiments, the preparation includes administering a Notch ligand to a subject and/or inducing expression of a Notch ligand in a subject. In some embodiments, the preparation further includes administering rapamycin.

As shown in Example 1, CMV seropositive reduced intensity conditioning (RIC) recipients had moderately higher absolute monocyte counts (AMC) at viral reactivation compared to myeloablative (MA) conditioning recipients. Furthermore, AMC at viral diagnosis correlated with subsequent $CD56^{dim}CD57^+$ $NKG2C^+$ NK cell expansion. One way in which monocytes likely promote adaptive NK cell differentiation and expansion is through production of IL-12. Other inflammatory cytokines, such as IL-18 and type-I IFN (IFN-α and IFN-β), produced by monocyte-derived dendritic cells can enhance NK cell function and may contribute to the differentiation or maturation of adaptive NK cells. In some embodiments, a monocyte includes a CD14$^+$ monocyte, a macrophage; a dendritic cell including, for example, a mature dendritic cells; an antigen presenting cell; and/or another myeloid cell.

Although the expansion of CD56$^{dim}$CD57$^+$ NKG2C$^+$ NK cells is associated with CMV infection or reactivation post-transplant, the cells do not appear to have strict specificity for CMV antigen. In fact, in vitro experiments demonstrated that, compared to other NK cell subsets, CD56$^{dim}$CD57$^+$ NKG2C$^+$ NK cells exhibit markedly elevated TNF and IFN-γ production in response to K562 myeloid leukemia cells. Similar to virally infected cells, cancer cells can down-regulate classical class I HLA molecules while retaining expression of HLA-E. The switch in receptor usage for HLA-E recognition from predominantly inhibitory NKG2A to activating NKG2C may be a mechanism by which adaptive NK cells mediate graft vs. leukemia effects.

In leukemia patients undergoing hematopoietic cell transplantation (HCT), CMV reactivation is associated with the expansion of NKG2C$^{high}$CD57$^+$ NK cells. These cells persist at high frequencies for at least 1 year post-transplant, were enriched for the expression of educating inhibitory KIR, and produced interferon (IFN)-γ at a high frequency in response to stimulation with K562 myeloid leukemia cells (Foley et al., *Blood.* 2011; 118(10):2784-2792; Foley et al., *J Immunol.* 2012; 189(10):5082-5088).

Administration

An adaptive NK cell prepared in vitro or in vivo can be administered to a subject alone or in a pharmaceutical composition that includes additional active agent and/or a pharmaceutically acceptable carrier. The adaptive NK cell can be administered to a patient, preferably a mammal, and more preferably a human, in an amount effective to produce the desired effect. The adaptive NK cell can be administered via a variety of routes, including, for example, intravenously, intratumorally, intraarterially, transdermally, via local delivery by catheter or stent, via a needle or other device for intratumoral injection, subcutaneously, etc. The adaptive NK cell can be administered once or multiple times. A physician having ordinary skill in the art can determine and prescribe the effective amount and dosing of adaptive NK cells and, optionally, the pharmaceutical composition required.

In some embodiments, a composition can be administered to a subject. In some embodiments, the composition includes an adaptive NK cell or a composition including an isolated population of NK cells including an adaptive NK cell. In some embodiments, the composition can include an inhibitor of reactive oxygen species (ROS) production including, for example, a catalase; a CD155 inhibitor; and/or a TIGIT inhibitor. In some embodiments, the ROS production inhibitor and/or the CD155 inhibitor is present in an amount sufficient to reduce the expression of CD155 on MDSCs in vivo and/or in vitro.

Methods of Treatment

In one aspect, an adaptive NK cell can be used to treat or prevent cancer, a precancerous condition, or a virus in a subject a subject. In a another aspect, an adaptive NK cell can be prepared in vivo in a subject suffering from cancer, a precancerous condition, or a virus to treat the cancer, precancerous condition, or virus.

In some embodiments a myeloid-derived suppressor cell (MDSC) may be found in the subject including, for example, in the subject's blood. In some embodiments, the level of MDSCs may be elevated relative to the level of MDSCs in a subject without cancer, a precancerous condition, or a virus. In some embodiments, the MDSC express CD11b, CD33, and low or no HLA-DR. In some embodiments, the MDSCs are either CD14+ (monocytic MDSCs [mMDSCs]) or CD15+CD66b+ (granulocytic MDSCs [gMDSCs]) (see Marvel et al. The Journal of Clinical Investigation. 2015; 125(9):3356-64).

The cancer may include, for example, bone cancer, brain cancer, breast cancer, cervical cancer, cancer of the larynx, lung cancer, pancreatic cancer, prostate cancer, skin cancer, cancer of the spine, stomach cancer, uterine cancer, hematopoietic cancer, and/or lymphoid cancer, etc. A hematopoietic cancer and/or lymphoid cancer may include, for example, acute myelogenous leukemia (AML), acute lymphoblastic leukemia (ALL), myelodysplastic syndromes (MDS), non-Hodgkin lymphoma (NHL), chronic myelogenous leukemia (CIVIL), Hodgkin's disease, and/or multiple myeloma. The cancer can be a metastatic cancer.

The virus can include, for example, a herpes virus, including for example, CMV, Varicella zoster virus (VZV), Epstein-Barr virus (EBV), a herpes simplex virus (HSV) or Kaposi's sarcoma-associated herpesvirus (KSHV); or a lentivirus, including for example, human immunodeficiency virus (HIV).

In a further aspect, an adaptive NK cell can be administered to or prepared in a subject inhibit the growth of a tumor in a subject. In some embodiments, the tumor can include a solid tumor.

An adaptive NK cell can be administered or prepared in a subject before, during, and/or after other treatments. Such combination therapy can involve the administration or preparation of an adaptive NK cell before, during, and/or after the use of a therapeutic agent, an anti-cancer agent and/or an anti-viral agents. Other therapeutic agents, anti-cancer agents, and anti-viral agents can include, for example, a cytokine; a chemokine; a therapeutic antibody including, for example, a high affinity anti-CMV IgG antibody; an NK cell receptor ligand, including, for example, BiKE or TRiKE; an adjuvant; an antioxidant; a chemotherapeutic agent; and/or radiation. The administration or preparation can be separated in time from the administration of other anti-cancer agents and/or anti-viral agents by hours, days, or even weeks. Additionally or alternatively, the administration or preparation can be combined with other biologically active agents or modalities such as, but not limited to, an antineoplastic agent, and non-drug therapies, such as, but not limited to, surgery.

In some embodiments, the present disclosure provides a method for enhancing anti-tumor immune responses. In some embodiments, the method can include the use of an adaptive NK cell or an isolated population of cells including an adaptive NK cell. In some embodiments, the method can further include altering the control of inhibitory receptors including, for example, TIGIT or PD-1.

In a further aspect, the present disclosure provides a method of modulating conventional NK cells. In some embodiments the method includes blocking the suppressive capacity of MDSCs to rescue or reverse functional hyporesponsiveness of conventional NK cells. In some embodiments, the method of modulating includes inhibiting TIGIT expression. In some embodiments, the method can include administration of a composition that includes an inhibitor of reactive oxygen species (ROS) production including, for example, a catalase; a CD155 inhibitor; and/or a TIGIT inhibitor. In some embodiments, the ROS production inhibitor and/or the CD155 inhibitor is present in an amount sufficient to reduce the expression of CD155 on MDSCs.

EXEMPLARY EMBODIMENTS

Embodiment 1

A composition comprising an adaptive NK cell.

Embodiment 2

The composition of Embodiment 1, wherein the adaptive NK cell is $CD3^-$ and $CD56^+$.

Embodiment 3

The composition of either of Embodiments 1 or 2, wherein the adaptive NK cell is $CD57^+$.

Embodiment 4

The composition of any of Embodiments 1 to 3, wherein the adaptive NK cell is $NKG2C^+$.

Embodiment 5

The composition of any of Embodiments 1 to 4, wherein the adaptive NK cell is $SYK^-$.

Embodiment 6

The composition of any of Embodiments 1 to 5, wherein the adaptive NK cell is $Fc\varepsilon R\gamma^-$.

Embodiment 7

The composition of any of Embodiments 1 to 6, wherein the adaptive NK cell is $EAT-2^-$.

Embodiment 8

The composition of any of Embodiments 1 to 7, wherein the adaptive NK cell is $CD56^{dim}$.

Embodiment 9

The composition of any of Embodiments 1 to 8, wherein the adaptive NK cell is $TIGIT^{low}$.

Embodiment 10

The composition of any of Embodiments 1 to 9, wherein the adaptive NK cell is $CD45RO^+$.

Embodiment 11

The composition of any of Embodiments 1 to 10, wherein the adaptive NK cell is $CD45RA^-$.

Embodiment 12

The composition of any of Embodiments 1 to 11, wherein the adaptive NK cell is long-lived.

Embodiment 13

The composition of any of Embodiments 1 to 12, wherein PD-1 expression or expression of the promyelocytic leukemia zinc finger (PLZF) transcription factor is decreased in an adaptive NK cell compared to a canonical NK cell.

Embodiment 14

The composition of Embodiment 13, wherein PLZF expression is decreased by at least 90%.

Embodiment 15

The composition of any of Embodiments 1 to 14, wherein the adaptive NK cell does not express the transcription factor promyelocytic leukemia zinc finger (PLZF).

Embodiment 16

The composition of any of Embodiments 1 to 15, wherein the adaptive NK cell demonstrates anti-tumor activity.

Embodiment 17

The composition of Embodiment 16, wherein the tumor comprises a tumor of a hematopoietic and/or lymphoid tissue.

Embodiment 18

The composition of Embodiment 16, wherein the tumor is a solid tumor.

Embodiment 19

The composition of any of Embodiments 1 to 18 wherein the composition comprises a pharmaceutically acceptable carrier.

Embodiment 20

A method of preparing the adaptive NK cell of any of Embodiments 1 to 18.

Embodiment 21

The method of Embodiment 20, wherein the adaptive NK cell is prepared in vitro.

Embodiment 22

The method of either of Embodiments 20 or 21, wherein the adaptive NK cell is derived from a cell from a cytomegalovirus (CMV) naïve source.

Embodiment 23

The method of any of Embodiments 20 to 22, wherein the adaptive NK cell is derived from a cell isolated from blood.

Embodiment 24

The method of any of Embodiments 20 to 23, wherein the adaptive NK cell is derived from a pluripotent stem cell.

Embodiment 25

The method of Embodiment 24, wherein the pluripotent stem cell is an induced pluripotent stem cell.

Embodiment 26

The method of any of Embodiments 20 to 25, wherein the adaptive NK cell is derived from an embryonic stem cell.

Embodiment 27

The method of any of Embodiments 20 to 26, wherein the adaptive NK cell is derived from a cell isolated from umbilical cord blood.

Embodiment 28

The method of any of Embodiments 20 to 27, wherein the adaptive NK cell is derived from a cell cultured in a culture medium comprising at least one of IL-15, IL-21, IL-18, IL-12, IL-2, IFN-α, or IFN-β.

Embodiment 29

The method of any of Embodiments 20 to 28, wherein the adaptive NK cell is derived from a cell cultured in a culture medium comprising rapamycin.

Embodiment 30

The method of any of Embodiments 20 to 29, wherein the adaptive NK cell is derived from a cell cultured in a culture medium comprising a Notch ligand.

Embodiment 31

The method of any of Embodiments 20 to 30, wherein the adaptive NK cell is derived from a cell cultured in a culture medium comprising an NKG2C receptor agonist.

Embodiment 32

The method of any of Embodiments 20 to 31, wherein the adaptive NK cell is derived from a cell co-cultured with an antigen presenting cell.

Embodiment 33

The method of embodiment 32, wherein the antigen presenting cell comprises a dendritic cell.

Embodiment 34

The method of any of Embodiments 20 to 33, wherein the adaptive NK cell is derived from a cell cultured in media comprising a CMV peptide or from a cell co-cultured with an antigen presenting cell, wherein the antigen presenting cell is cultured in media with a CMV peptide.

Embodiment 35

The method of Embodiment 20, wherein the adaptive NK cell is prepared in vivo.

Embodiment 36

The method of Embodiment 35, wherein the method comprises administering a cytomegalovirus (CMV) vaccine to a subject.

Embodiment 37

The method of either of Embodiment 35 or Embodiment 36, wherein the method comprises administering inactivated cytomegalovirus (CMV) to a subject.

Embodiment 38

The method of any of Embodiments 35 to 37, wherein the method comprises administering a cytokine to a subject.

Embodiment 39

The method of Embodiment 38, wherein the cytokine comprises at least one of IL-15, IL-21, IL-12, IL-18, and GM-CSF.

Embodiment 40

The method of any of Embodiments 35 to 39, wherein the method comprises administering a Notch ligand to a subject.

Embodiment 41

The method of any of Embodiments 35 to 40, wherein the method comprises inducing expression of a Notch ligand in a subject.

Embodiment 42

The method of any of Embodiments 35 to 41, wherein the subject is CMV seropositive.

Embodiment 43

A method for treating or preventing cancer, a precancerous condition, or a virus in a subject, the method comprising:
administering to the subject the adaptive NK cell of any of Embodiments 1 to 18.

Embodiment 44

The method of Embodiment 43, wherein the cancer comprises bone cancer, brain cancer, breast cancer, cervical cancer, ovarian cancer, cancer of the larynx, lung cancer, pancreatic cancer, prostate cancer, skin cancer, cancer of the spine, stomach cancer, uterine cancer, hematopoietic cancer, or lymphoid cancer.

Embodiment 45

The method of either of Embodiments 43 or 44, wherein the cancer is a metastatic cancer.

Embodiment 46

A method of inhibiting the growth of a tumor in a subject, the method comprising administering to the subject a composition comprising the adaptive NK cell of any of Embodiments 1 to 18.

Embodiment 47

The method of Embodiment 46, wherein the tumor comprises a solid tumor.

Embodiment 48

The method of Embodiment 43, wherein the virus comprises a lentivirus or a herpes virus.

Embodiment 49

A method for treating or preventing cancer or a precancerous condition in a subject, the method comprising administering the in vivo preparation of any of Embodiments 35 to 42 to the subject.

Embodiment 50

The method of Embodiment 49, wherein the cancer comprises bone cancer, brain cancer, breast cancer, cervical cancer, ovarian cancer, cancer of the larynx, lung cancer, pancreatic cancer, prostate cancer, skin cancer, cancer of the spine, stomach cancer, uterine cancer, hematopoietic cancer, or lymphoid cancer.

Embodiment 51

The method of either of Embodiments 49 or 50, wherein the cancer is a metastatic cancer.

Embodiment 52

A method of inhibiting the growth of a tumor in a subject, the method comprising the in vivo preparation of Embodiments 35 to 42.

Embodiment 53

The method of Embodiment 52, wherein the tumor comprises a solid tumor.

Embodiment 54

The method of any of Embodiments 43 to 53 further comprising administering a composition comprising a therapeutic agent.

Embodiment 55

The method of Embodiment 54, wherein the therapeutic agent comprises at least one of a cytokine, a chemokine, a therapeutic antibody, an adjuvant, an antioxidant, or a chemotherapeutic agent.

Embodiment 56

The method of any of Embodiments 43 to 55, wherein the subject comprises a myeloid-derived suppressor cell (MDSC).

Embodiment 57

The method of any of Embodiments 43 to 56, wherein the subject has received a hematopoietic cell transplant.

Embodiment 58

A method for treating or preventing cancer, a precancerous condition, or a virus in a subject, the method comprising preparing an adaptive NK cell in the subject.

Embodiment 59

The method of Embodiment 58, wherein the method comprises administering a cytomegalovirus (CMV) vaccine to a subject.

Embodiment 60

The method of either of Embodiment 58 or Embodiment 59, wherein the method comprises administering inactivated cytomegalovirus (CMV) to a subject.

Embodiment 61

The method of any of Embodiments 58 to 60, wherein the method comprises administering a cytokine to a subject.

Embodiment 62

The method of Embodiment 61, wherein the cytokine comprises at least one of IL-15, IL-21, IL-12, IL-18, and GM-CSF.

Embodiment 63

The method of any of Embodiments 58 to 62, wherein the method comprises administering a Notch ligand to a subject.

Embodiment 64

The method of any of Embodiments 58 to 63, wherein the method comprises inducing expression of a Notch ligand in a subject.

Embodiment 65

The method of any of Embodiments 58 to 64, wherein the subject is CMV seropositive.

Embodiment 66

The method of any of Embodiments 58 to 65, wherein the subject has received a hematopoietic cell transplant.

Embodiment 67

The method of any of Embodiments 58 to 66, wherein the subject has been diagnosed with a leukemia.

Embodiment 68

The method of any of Embodiments 58 to 67, wherein the subject comprises a myeloid-derived suppressor cell (MDSC).

Embodiment 69

A method comprising:
(a) obtaining a blood sample from a subject; and
(b) culturing a population of NK cells of the blood sample in a culture medium comprising one or more of IL-15, IL-21, and a Notch ligand to obtain an adaptive NK cell;
wherein the adaptive NK cell is $CD56^{dim}$ and is one or more of $NKG2C^+$ and $TIGIT^{low}$.

Embodiment 70

The method of Embodiment 69, wherein the culture medium of step (b) further comprises at least one of rapamycin and an activator of CD16 signaling.

Embodiment 71

A method comprising
(a) obtaining a blood sample from a subject; and
(b) culturing a population of NK cells of the blood sample with a CMV peptide-supplemented mature dendritic cell to obtain an adaptive NK cell;
wherein the adaptive NK cell is CD56$^{dim}$ and is one or more of NKG2C$^+$ and TIGIT$^{low}$.

Embodiment 72

A method comprising
(a) obtaining a blood sample from a subject, wherein the subject is CMV seropositive; and (b) culturing a population of NK cells of the blood sample with autologous monocytes and
IL-15 to obtain an adaptive NK cell;
wherein the adaptive NK cell is CD56$^{dim}$ and is one or more of NKG2C$^+$ and TIGIT$^{low}$.

Embodiment 73

The method of any of Embodiments 69 to 72, wherein step (b) further comprises contacting the NK cells of the blood sample with a TIGIT inhibitor.

Embodiment 74

The method of Embodiment 73, wherein the TIGIT inhibitor comprises an antibody against TIGIT.

Embodiment 75

The method of any of Embodiments 69 to 74, wherein step (b) further comprises contacting the NK cells of the blood sample with an inhibitor of at least one of PLZF, TIGIT, or PD-1

Embodiment 76

The method of any of Embodiments 69 to 75, the method further comprising genetic knockdown of at least one of PLZF, TIGIT, or PD-1 in the NK cells of the blood sample or in the adaptive NK cell or both.

Embodiment 77

The method of any of Embodiments 69 to 76, wherein the adaptive NK cell is at least one of CD57$^+$, SYK$^-$, FcεRγ$^-$, EAT-2$^-$, CD45RO$^+$, and CD45RA$^-$.

Embodiment 78

The method of any of Embodiments 69 to 77, wherein the adaptive NK cell exhibits reduced expression of PLZF compared to the population of NK cells prior to culture.

Embodiment 79

The method of any of Embodiments 69 to 78, wherein the adaptive NK cell exhibits an enhanced anti-tumor immune activity compared to the population of NK cells prior to culture.

Embodiment 80

The method of any of Embodiments 69 to 79, wherein the adaptive NK cell exhibits one or more of increased cytotoxicity, increased cytokine production, increased persistence, and increased resistance to T regulatory cells compared to the population of NK cells prior to culture.

Embodiment 81

The method of any of Embodiments 69 to 80, the method further comprising administering a cytomegalovirus (CMV) vaccine to the subject.

Embodiment 82

The method of any of Embodiments 69 to 81, wherein culturing the population of NK cells comprises cell expansion or cell phenotype skewing or both.

Embodiment 83

The method of any of Embodiments 69 to 82, the method further comprising
(c) isolating the adaptive NK cell.

Embodiment 84

A composition comprising an adaptive NK cell obtained by the method of any of Embodiments 69 to 83.

Embodiment 85

A composition comprising a population of NK cells, wherein the population of NK cells is enriched for an adaptive NK cell obtained by the method of any of Embodiments 69 to 83.

Embodiment 86

An isolated population of NK cells wherein the cells are CD56$^{dim}$, and one or more of NKG2C$^+$, CD57$^+$, and TIGIT$^{low}$.

Embodiment 87

The isolated population of NK cells of Embodiment 86, wherein the cells exhibit reduced expression of at least one of PLZF and PD-1 compared to a canonical NK cell.

Embodiment 88

An isolated population of NK cells, wherein the isolated population is enriched for an NK cell that is CD56$^{dim}$ and NKG2C$^+$.

Embodiment 89

The isolated population of NK cells of Embodiment 88, wherein the isolated population is enriched for an NK cell exhibiting reduced expression of at least one of PLZF, TIGIT, and PD-1 compared to a canonical NK cell.

Embodiment 90

The isolated population of NK cells of any of Embodiments 86 to 89, wherein the NK cell population exhibits an enhanced anti-tumor immune activity compared to a canonical NK cell.

Embodiment 91

The isolated population of NK cells of any of Embodiments 86 to 90, wherein, wherein the NK cell population can overcome myeloid-derived suppressor cell (MDSC)-induced suppression of an immune response.

Embodiment 92

The isolated population of NK cells of any of Embodiments 86 to 91, wherein the NK cell population can overcome Treg-induced suppression of an immune response.

Embodiment 93

A composition comprising the isolated population of NK cells of any one of Embodiments 86 to 92.

Embodiment 94

The composition of Embodiment 93, the composition further comprising at least one of a CD155 inhibitor, a TIGIT inhibitor, and an inhibitor of the production of reactive oxygen species (ROS).

Embodiment 95

The composition of Embodiment 94, wherein the inhibitor of the production of ROS comprises a catalase.

Embodiment 96

The composition of either of Embodiments 94 or 95, wherein the ROS production inhibitor or the CD155 inhibitor is present in an amount sufficient to reduce the expression of CD155 on a myeloid-derived suppressor cell (MDSC).

The present invention is illustrated by the following examples. It is to be understood that the particular examples, materials, amounts, and procedures are to be interpreted broadly in accordance with the scope and spirit of the invention as set forth herein.

Examples

Example 1

CD56$^{dim}$CD57$^+$ NKG2C$^+$ NK Cell Expansion is Associated with Reduced Leukemia Relapse after Reduced Intensity HCT
Introduction Natural killer (NK) cells are the predominant lymphocyte population to reconstitute early after hematopoietic cell transplantation (HCT) and have the potential to influence post-HCT outcomes. However, the graft vs. leukemia (GvL) activity of NK cells is limited by delayed NK cell functional maturation throughout the first year after HCT. The immature phenotype of reconstituting donor NK cells is associated with significant impairments in NK cell-mediated cytotoxicity and interferon (IFN)-γ production in response to tumor cell lines and primary acute myelogenous leukemia (AML) blasts ex vivo. Overall, the phenotypic and functional immaturity of donor NK cells reconstituting early after HCT limits their clinical benefit.

NK cells expressing high levels of the activating receptor NKG2C robustly expand in HCT recipients after CMV reactivation, preferentially acquire the maturation marker CD57 and persist for at least 1 year post-HCT. In many respects, CD56$^{dim}$CD57$^+$ NKG2C$^+$ NK cells appear to represent a human analogue of Ly49H$^+$ memory NK cells that participate in the clearance of murine CMV (MCMV) infections. Thus, CMV reactivation has a powerful effect in HCT recipients and drives the maturation of NK cells with heightened effector functions. CD56$^{dim}$CD57$^+$ NKG2C$^+$ NK cells are referred to herein as adaptive.

Several recent studies have reported an association between CMV reactivation and reduced risk of relapse after HCT, but a specific mechanism for this observation has not been described. CMV-induced CD56$^{dim}$CD57$^+$ NKG2C$^+$ NK cells with enhanced function and long-term persistence may promote cancer control in transplant recipients. This study sought to define the relevant transplant-related variables that influence the protective effect of CMV reactivation on relapse and to determine whether CD56$^{dim}$CD57$^+$ NKG2C$^+$ NK cells are directly associated with clinical outcomes post-HCT.

Patients and Methods
Transplant Procedures

Myeloablative (MA) conditioning was used in 366 patients with malignant hematologic diseases and consisted of cyclophosphamide (60 mg/kg×2) and total body irradiation (13.2 Gy, 165 cGy twice daily×4 days). For some, this regimen also included fludarabine (25 mg/m$^2$/day on day −8 through −6 and mycophenolate mofetil (1 g every 12 hours from day −3 to day +30). All patients also received cyclosporine A starting at day −3 and continuing through 180 days post-HCT. Reduced intensity conditioning (RIC) was used in 308 patients and consisted of cyclophosphamide (50 mg/kg) and fludarabine (200 mg/m$^2$) and total body irradiation (2 Gy). Following conditioning, stem cells from bone marrow, peripheral blood or cord blood (single or double) were infused. Table I describes the HCT patient demographics stratified by recipient CMV status (seronegative, seropositive without reactivation and seropositive with reactivation).

TABLE I

Demographics by CMV serostatus and reactivation

| | Variable | CMV seronegative | CMV seropositive | CMV reactivation | p* |
|---|---|---|---|---|---|
| n | | 270 | 214 | 190 | 0.07 |
| Age | Median (range) | 42 (2-72) | 37 (1-74) | 45 (1-71) | |
| | IQR | (22-57) | (15-54) | (25-56) | |
| Gender | Male | 163 (60%) | 120 (56%) | 107 (56%) | 0.56 |
| | Female | 107 (40%) | 94 (44%) | 83 (44%) | |
| | ALL | 81 (30%) | 57 (26%) | 49 (26%) | 0.97 |
| | AML | 123 (46%) | 99 (46%) | 91 (48%) | |
| | CML | 14 (5%) | 8 (4%) | 6 (3%) | |
| Diagnosis | MDS | 31 (12%) | 29 (14%) | 25 (13%) | |
| | NHL | 16 (6%) | 14 (7%) | 12 (6%) | |
| | Hodgkins | 4 (2%) | 5 (2%) | 5 (3%) | |
| | Multiple Myeloma | 1 (<1%) | 2 (1%) | 2 (1%) | |

TABLE I-continued

Demographics by CMV serostatus and reactivation

| | Variable | CMV seronegative | CMV seropositive | CMV reactivation | p* |
|---|---|---|---|---|---|
| Diagnosis Risk | Standard risk | 211 (78%) | 160 (75%) | 145 (76%) | 0.68 |
| | High risk | 59 (22%) | 54 (25%) | 45 (24%) | |
| Prior Auto | Yes | 14 (5%) | 9 (4%) | 13 (7%) | 0.50 |
| CMV Serostatus D/R | neg/neg | 247 (92%) | | 7 (4%) | |
| | neg/pos | 23 (8%) | | 3 (2%) | |
| | pos/neg or pos/pos | | 214 (100%) | 180 (95%) | |
| Conditioning Intensity | MA | 140 (52%) | 127 (59%) | 99 (52%) | 0.20 |
| | RIC | 130 (48%) | 87 (41%) | 91 (48%) | |
| GvHD prophylaxis | Csa or Tac w/ MTX | 51 (19%) | 56 (26%) | 33 (17%) | 0.08 |
| | Csa or Tac w/ MMF | 206 (76%) | 151 (71%) | 153 (81%) | |
| | Other | 13 (5%) | 7 (3%) | 4 (2%) | |
| Donor type | Matched sibling | 75 (28%) | 81 (38%) | 48 (25%) | 0.01 |
| | Single UCB | 50 (19%) | 39 (18%) | 27 (14%) | |
| | Double UCB | 145 (54%) | 94 (44%) | 115 (61%) | |
| Date of transplant | 2001-2007 | 139 (52%) | 121 (57%) | 98 (52%) | 0.48 |
| | 2008-2013 | 131 (49%) | 93 (44%) | 92 (48%) | |

*A p-value for between-treatment comparisons. Continuous variables were analyzed by a general Wilcoxon test. Categorical variables were analyzed by chi-square CMV Screening and Treatment Prior to conditioning, all recipients were assessed for CMV exposure by serology using enzyme-linked immunosorbent assays: CMV IgG antibody level greater than (>) 10.0 ELISA Units per milliliter (EU/mL) was considered seropositive. After transplant, all recipients underwent weekly screening for CMV reactivation by either pp65 antigenemia (prior to 2006) or quantitative real-time polymerase chain reaction (PCR) (after 2006) until day +100 post-transplant. CMV prophylaxis included high-dose acyclovir (500 mg/m$^2$ [10-12 mg/kg] i.v. every 8 hours or 800 mg [18 mg/kg pediatric] orally 5 times daily) until day 100. CMV reactivation was defined as CMV antigenemia ($\geq$2 pp65-positive cells/50,000), DNAemia ($\geq$500 copies by quantitative real-time PCR) or culture of CMV from blood, body fluid or tissue and was treated with ganciclovir or foscarnet.

Data Collection

The University of Minnesota Blood and Marrow Transplant program prospectively collected all data regarding patient characteristics and outcomes. The University of Minnesota institutional review board approved all protocols, and all patients (and/or their legal guardians) provided informed consent in accordance with the Declaration of Helsinki.

Phenotypic Analysis of Reconstituting NK Cells in HCT Recipients

Peripheral blood mononuclear cells (PBMCs) from HCT recipients were isolated from peripheral blood samples by density gradient centrifugation and analyzed by fluorescence-activated cell sorting (FACS) using an LSR II (BD Biosciences, San Jose, Calif.). PBMCs from recipients that reactivated CMV were collected at viral diagnosis, at 2 weeks, 4 weeks, and 8 after antiviral therapy and at 6 months and 1 year post-transplant. For recipients that were CMV seronegative or were CMV seropositive without viral reactivation, PBMCs were collected at day 100, 6 months and 1 year post-transplant. The following fluorescently conjugated antibodies were used for phenotypic analysis: Energy Coupled Dye (ECD)-conjugated anti-CD3 (Beckman Coulter, Inc., Brea, Calif.; IM2705U), PECy7-conjugated anti-CD56 (BioLegend, San Diego, Calif.; 318318), Pacific Blue-conjugated anti-CD57 (BioLegend, San Diego, Calif.; 322316) and PE-conjugated NKG2C (R&D Systems, Minneapolis, Minn.; FAB138P-025). For statistical comparisons of adaptive NK cell percentages and absolute counts between RIC and MA recipients, unpaired, two-sided t-tests calculated using GraphPad were used. Error bars represent SEM. GraphPad was used to calculate $R^2$ values and associated p values for the correlation between absolute monocyte and lymphocyte counts and adaptive NK cell expansion in 28 CMV seropositive recipients.

Statistical Analysis of Clinical Associations in the HCT Cohort

Kaplan-Meier curves were used to estimate the probability of disease free survival (DFS) through 1-year post-HCT (Kaplan et al. *J. Am. Stat. Assoc.* 1958; 53:457-481.), and the log-rank test was used for comparisons. Adjusted survival curves were calculated based on a stratified Cox model (Chang et al. *J. Chronic Dis.* 1982; 35:669-674). Cox regression was used to examine the independent effect of factors on DFS, and proportional hazards were checked using Martingale residuals. The cumulative incidence of relapse was assessed treating non-relapse mortality (NRM) as a competing risk. The Fine and Gray proportional hazards model (Fine et al. *J. Am. Stat. Assoc.* 1999; 94:496-509) was used to determine the independent effect of CMV reactivation on relapse and to calculate adjusted relapse curves. The primary covariates of interest were CMV reactivation post-HCT, treated as a time-dependent covariate, and conditioning regimen intensity. Potential confounders included donor type, diagnosis, year of transplant (<2008 versus $\geq$2008), graft-versus-host disease (GvHD) prophylaxis, gender, disease risk and prior autologous transplant. Disease risk at the time of HCT was classified into standard risk or high risk based on the ASBMT RFI 2006 risk scoring schema (available on the world wide web at asbmt.org). Variance was similar between groups being compared. Recursive partitioning was used to determine the optimal cut points for the percentages and absolute numbers of adaptive CD56$^{dim}$CD57$^+$ NKG2C$^+$ NK cells in association with relapse. All clinical analyses were performed using SAS version 9.3 (SAS Institute, Cary, N.C.).

NK Cell Function Assays

Buffy coats collected from 5 healthy CMV seropositive donors were obtained from Memorial Blood Bank (Minneapolis, Minn.). Peripheral blood mononuclear cells (PBMCs) were isolated by density gradient centrifugation using Ficoll-Paque (GE Healthcare, Little Chalfont, Buckinghamshire, United Kingdom) and cultured with K562 cells at a 2:1 (effector:target) ratio for 5 hours in RPMI media supplemented with 10% fetal bovine serum (Gibco, LifeTechnologies, Thermo Fisher Scientific Inc., Waltham, Mass.). GolgiStop and GolgiPlug protein transport inhibitors (BD Biosciences, San Jose, Calif.) were added 1 hour into the assay. The following antibodies were used for functional analysis of NK cell subsets: BV785-conjugated anti-CD3 (BioLegend, San Diego, Calif.; 318318), PECy7-conjugated anti-CD56 (BioLegend, San Diego, Calif.; 359620), PE-CF594-conjugated anti-CD57 (BioLegend, San Diego, Calif.; 359620), PE-conjugated NKG2C (R&D Systems, Minneapolis, Minn.; FAB138P-025), PerCP-Cy5.5-conjugated anti-CD107a (BioLegend, San Diego, Calif.; 328616), and BV605-conjugated IFN-γ (BioLegend, San Diego, Calif.; 502536). The K562 cell line was purchased from ATCC (Manassas, Va.) and is screened monthly for *mycoplasma* contamination. The experiment was performed 2 independent times. Two-sided, paired t-tests in GraphPad were used to determine significance. Error bars represent SEM.

Results

Lower Relapse Risk Post-HCT in RIC Recipients that Reactivate CMV.

One year relapse risk and DFS was analyzed in 674 allogeneic HCT recipients with acute myelogenous leukemia (AML), (n=313), acute lymphoblastic leukemia (ALL) (n=187), myelodysplastic syndromes (MDS) (n=85), non-Hodgkin lymphoma (NHL) (n=42), chronic myelogenous leukemia (CML) (n=28), Hodgkin's disease (n=14), and multiple myeloma (n=5) treated at the University of Minnesota between 2001 and 2013. 516 patients were classified as standard risk, 148 patients as high risk and 36 patients had a prior autologous transplant. 37 patients received bone marrow, 166 patients received peripheral blood stem cells and 471 patients received cord blood grafts. The entire cohort was stratified by recipient CMV serostatus (CMV seronegative [n=270] vs. CMV seropositive without reactivation [n=214] vs. CMV seropositive with reactivation [n=190]) and by conditioning regimen (reduced intensity [n=308] vs. myeloablative [n=366]). Disease type and treatment-related variables were balanced across groups stratified by CMV serostatus (Table I).

Following RIC (n=308), CMV reactivation was associated with a lower risk of relapse 1 year post-HCT (26% [17-35%], p=0.05) compared to CMV seropositive recipients without reactivation (30% [20-40%]) or CMV seronegative recipients (35% [27-43%]) (FIG. 1A). Similarly, in RIC transplants CMV reactivation was associated with improved DFS (55% [45-65%] p=0.04) compared to CMV seropositive recipients without reactivation (45% [35-55%]) or CMV seronegative recipients (46% [38-54%]) (FIG. 1B). Following myeloablative conditioning (n=366), CMV serostatus or reactivation did not influence either relapse or DFS post-HCT (FIGS. 1C, 1D).

In regression analyses, CMV reactivation, but not seropositivity without reactivation, trended towards a lower risk of relapse (RR=0.6 [0.4-1.0], p=0.06) and was associated with significantly better DFS (RR=0.7 [0.6-1.0], p=0.04) in RIC recipients. There was no statistically significant effect of graft-versus-host disease (GvHD) and age on relapse and non-relapse mortality (NRM) in multivariate models within the RIC group (Table II). In contrast, for the MA cohort, grade II-IV acute GVHD and lower age were associated with both relapse protection and higher rates of NRM. While CMV reactivation or recipient seropositivity had no effect on relapse in the MA cohort, patients who were CMV positive but did not reactivate had lower disease free survival. Regression analyses were also performed separately for myeloid (AML and MDS) and other diagnoses (ALL, CIVIL, NHL, Hodgkin's and multiple myeloma). Though power was compromised and thus confidence intervals were wider with this further subsetting of these data, similar trends towards a lower risk of relapse in RIC recipients with CMV reactivation were observed in all disease groups (data not shown).

The primary beneficial effect of CMV reactivation occurs early (when it is most often detected), as the protective effect is less apparent for late relapses. There was no observed protection against late relapse (occurring after day 100) in survivors with earlier CMV reactivation (RR=1.0 [0.5-1.9], p=0.98). Similarly, there was no association between previous CMV reactivation and DFS in survivors beyond day 100. Since CMV reactivation after 100 days post-HCT is uncommon and asymptomatic reactivation is less often detected because it occurs beyond the window of routine monitoring, there were not enough events to fully evaluate the association between late CMV reactivation and late relapse. Together, these results show that the beneficial effect of CMV reactivation in the HCT setting is observed early after transplant and is evident only in recipients of RIC HCT.

TABLE II

Multiple variable regression analysis of relapse and NRM post-transplant

| Conditioning Intensity | Outcome | Recipient CMV Status | n | RR | P |
|---|---|---|---|---|---|
| RIC | Relapse | seronegative | 130 | 1.0 | |
| | | seropositive | 87 | 0.8 (0.5-1.4) | 0.46 |
| | | reactivation | 91 | 0.6 (0.4-1.0) | 0.06 |
| | NRM | seronegative | 130 | 1.0 | |
| | | seropositive | 87 | 1.0 (0.7-1.5) | 0.89 |
| | | reactivation | 91 | 0.7 (0.5-1.0) | 0.04 |
| MA | Relapse | seronegative | 140 | 1.0 | |
| | | seropositive | 127 | 1.2 (0.7-2.2) | 0.49 |
| | | reactivation | 99 | 1.0 (0.5-1.7) | 0.76 |
| | | No aGvHD | 210 | 1.0 | |
| | | Grade II-IV aGVHD | 156 | 0.5 (0.3-0.9) | 0.02 |
| | NRM | seronegative | 140 | 1.0 | |
| | | seropositive | 127 | 1.5 (1.0-2.6) | 0.04 |
| | | reactivation | 99 | 0.8 (0.5-1.3) | 0.35 |
| | | <21 years old | 171 | 1.0 | |
| | | ≥21 years old | 195 | 1.6 (1.2-2.3) | <0.01 |
| | | No aGvHD | 210 | 1.0 | |
| | | Grade II-IV aGvHD | 156 | 0.6 (0.4-0.8) | <0.01 |

Covariates tested included donor type (sibling vs. UCB), diagnosis (AML vs. others), year of transplant (<2008 vs. ≥2008), conditioning (MA vs. RIC), GvHD prophylaxis (MTX vs. MMF vs. other), gender (male vs. female), disease risk (standard vs. high), age (<21 vs. ≥21), grade II-IV aGvHD as a time-dependent variable (no vs. yes) and prior autologous transplant (no vs. yes).

CD56$^{dim}$CD57$^+$ NKG2C$^+$ NK Cells Preferentially Expand in RIC HCT Recipients after CMV Reactivation.

Figure 2B:
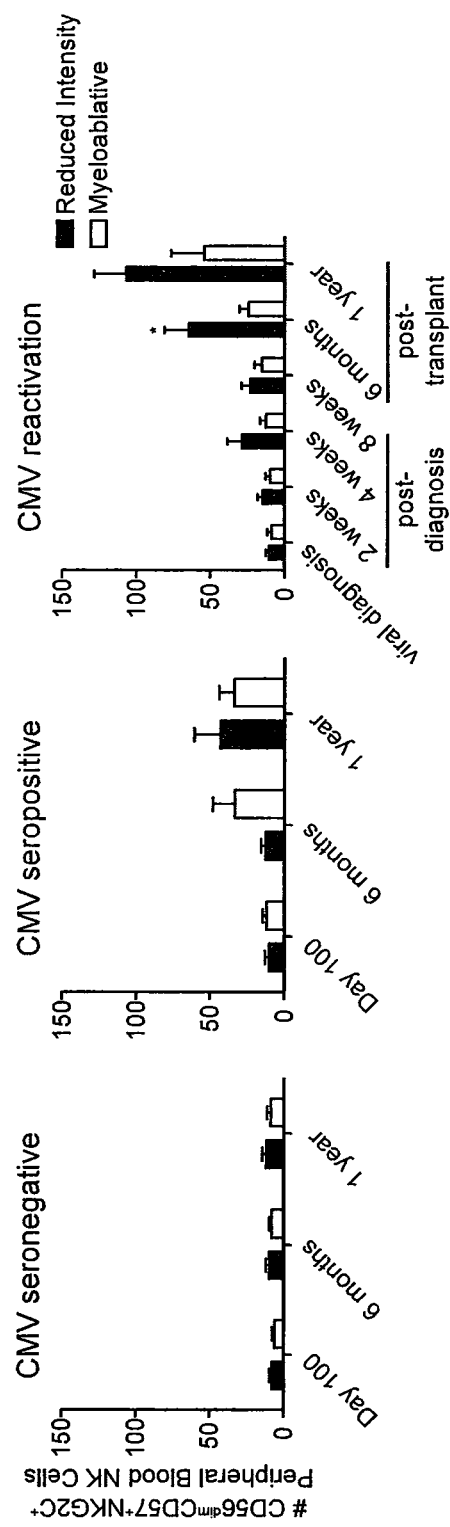

To further evaluate the association between CMV reactivation, relapse protection and improved DFS after RIC HCT, the phenotype of donor-derived peripheral blood NK cells post-HCT was analyzed. Increases in the frequency of CD56$^{dim}$CD57$^+$ NKG2C$^+$ NK cells in CMV seropositive, but not seronegative recipients, were observed at 6 months and 1 year (FIG. 2A, left and middle panels). Recipients who reactivated CMV exhibited the highest proportions of $CD56^{dim}CD57^+$ $NKG2C^+$ NK cells. Further analysis revealed that the frequencies of $CD56^{dim}CD57^+$ $NKG2C^+$ NK cells were significantly higher in RIC vs. MA recipients at 4 weeks (8.58% vs. 4.64%, p=0.02), 8 weeks (7.77% vs. 3.84%, p=0.02) and 6 months post-reactivation (14.80% vs. 6.29%, p=0.01) (FIG. 2A, right panel). Similarly, an association towards greater absolute numbers of $CD56^{dim}CD57^+$ $NKG2C^+$ NK cells in CMV seropositive recipients relative to CMV seronegative recipients was observed at 6 months and 1 year (FIG. 2B, left and middle panels). The absolute numbers of $CD56^{dim}CD57^+$ $NKG2C^+$ NK cells were highest in CMV seropositive recipients who reactivated CMV and were also significantly higher in RIC vs. MA recipients at 6 months (22.2 vs. 10.44 cells/μl, p=0.04) post-transplant. A similar trend in absolute numbers was observed at 1 year. The higher rate of $CD56^{dim}CD57^+$ $NKG2C^+$ NK cell expansion in RIC recipients was not explained by differences in acute GvHD rates at day 100, as these rates were not significantly different (p=0.46) between RIC (43% [38-43%]) and MA (42% [36-48%]) preparative regimens. The $CD56^{dim}CD57^+$ $NKG2C^+$ NK cells expanding from day 100 onward likely differentiated from cells of donor origin, as 91% of survivors had ≥90% donor chimerism at day 100, and 93% of survivors at 6 months had ≥90% donor chimerism. Thus, the expansion of donor-derived $CD56^{dim}CD57^+$ $NKG2C^+$ NK cells in response to CMV reactivation correlated with reduced relapse risk and superior DFS, but only among RIC recipients.

Expansion of $CD56^{dim}CD57^+$ $NKG2C^+$ NK Cells at 6 Months Post HCT is Directly Associated with Lower 2 Year Relapse Rates.

At 6 months post-HCT (n=68), absolute $CD56^{dim}CD57^+$ $NKG2C^+$ NK cell counts in recipients was analyzed independently of CMV serostatus or reactivation. At this time point, nearly all patients were greater than (>) 90% donor engrafted. To determine the optimal cut point for absolute counts of $CD56^{dim}CD57^+$ $NKG2C^+$ NK cells recursive partitioning was used. Recipients in the expanding group based on $CD56^{dim}CD57^+$ $NKG2C^+$ NK cell numbers (>2.5 cells/μl, n=54) trended toward a lower 2-year relapse rate (16% [6-26%], p=0.06) compared with the non-expanding group (0.1-2.5 cells/μl, n=14), who had higher 2-year relapse rates (46% [10-82%]) (Table III). Thus, these data suggest that $CD56^{dim}CD57^+$ $NKG2C^+$ NK cells that expand in response to CMV reactivation early after transplant protect against relapse.

TABLE III

Relapse rates stratified by $CD56^{dim}CD57^+NKG2C^+$ NK cell absolute counts at 6 months post-transplant
All Patients

| Absolute Counts | n | 2 year relapse (95% CI) | p (2 year estimate) | TRM (2 year estimate) |
|---|---|---|---|---|
| | | | 0.06 | |
| 0.1-2.5 cells/μl | 14 | 46% (10-82%) | | 7% |
| >2.5 | 54 | 16% (6-26%) | | 7% |

Recursive partitioning was used to determine optimal cut points of the absolute counts (cells/μl of blood) of $CD56^{dim}CD57^+NKG2C^+$ NK cells at 6 months post-transplant in association with 2 year relapse rates.

Higher Absolute Monocyte Counts at Viral Diagnosis are Associated with the Subsequent Expansion of $CD56^{dim}CD57^+$ $NKG2C^+$ NK Cells.

Figure 3A:
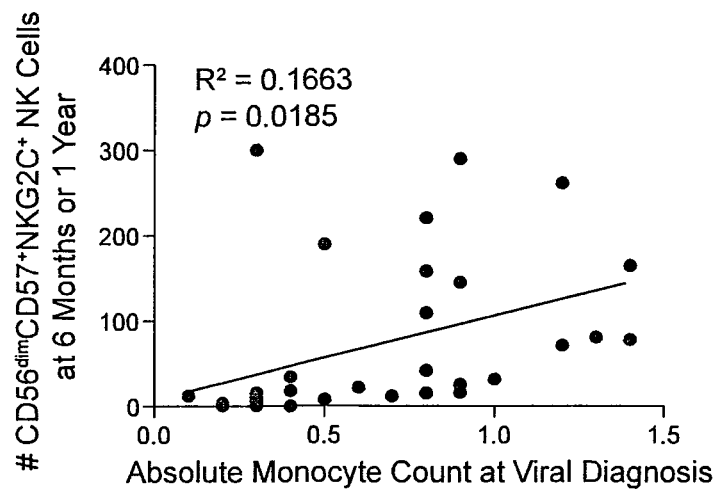
FIG. 3(A-D) shows absolute monocyte counts at the time of CMV reactivation are associated with $CD56^{dim}CD57^+$ $NKG2C^+$ NK cell expansion. Absolute monocyte counts from 28 CMV seropositive recipients at the time of viral reactivation were plotted against either the absolute number (FIG. 3A) or the percentage (FIG. 3B) of $CD56^{dim}CD57^+$ $NKG2C^+$ NK cells in peripheral blood samples from these recipients at either 6 months or 1 year. Absolute lymphocyte counts at the time of viral diagnosis from the same recipients were also plotted against either the absolute number (FIG. 3C) or the percentage (FIG. 3D) of $CD56^{dim}CD57^+$ $NKG2C^+$ NK cells in peripheral blood samples at either 6 months or 1 year.
Figure 3B:
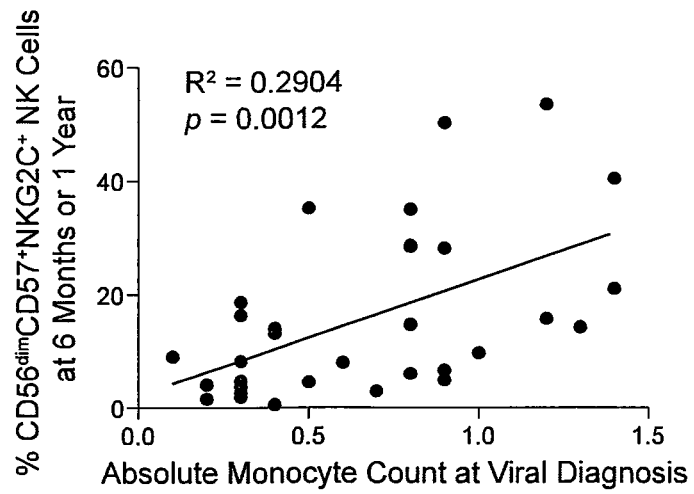
Figure 3C:
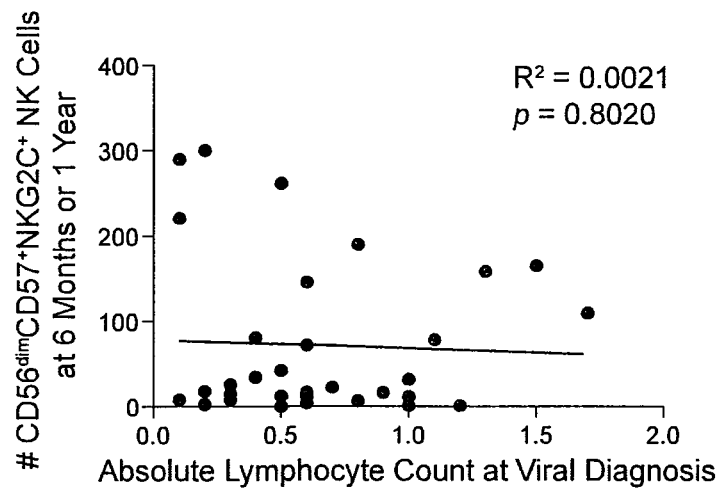
Figure 3D:
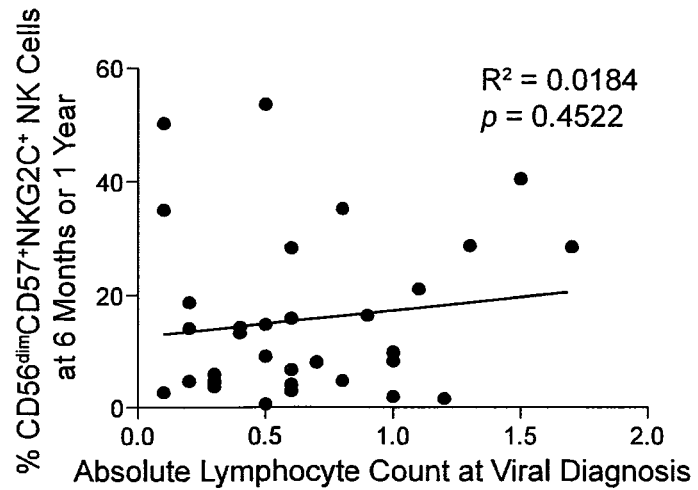

In vitro studies that mimic CMV infection have shown that monocytes play a role in promoting the expansion of NK cells expressing NKG2C (Rolle et al. *J Clin Invest.* 2014; 124:5305-5316). Thus, RIC recipients might have higher absolute monocyte counts (AMC) at viral diagnosis, accounting for the preferential expansion of $CD56^{dim}CD57^+$ $NKG2C^+$ NK cells relative to MA recipients (FIG. 2). Within the HCT cohort, there were 28 recipients (16 RIC and 12 MA) that experienced CMV reactivation for which AMC and absolute lymphocyte counts (ALC) at viral diagnosis and NK cell phenotypic data at 6 months and/or 1 year were available. At viral diagnosis, the average AMC trended higher in RIC compared to MA recipients (0.71 vs. 0.54×10$^9$ cells/L, p=0.08). In contrast, the average ALC was similar between RIC and MA recipients (0.65 vs. 0.61×10$^9$ cells/L, p=0.39). To determine whether an association exists between the number of monocytes present in the blood of recipients at the time of CMV reactivation and subsequent adaptive NK cell expansion, AMC values at viral diagnosis for each recipient were plotted against the absolute number and percentage of $CD56^{dim}CD57^+$ $NKG2C^+$ NK cells at either 6 months (if no 1 year phenotype was available) or 1 year. A significant positive correlation between AMC at viral diagnosis and both the absolute number (FIG. 3A, p=0.02) and relative percentage (FIG. 3B, p=0.01) of $CD56^{dim}CD57^+$ $NKG2C^+$ NK cells at 6 months or 1 year was observed. No such correlation was observed between ALC at viral diagnosis and $CD56^{dim}CD57^+$ $NKG2C^+$ NK cell expansion (FIG. 3C, FIG. 3D). Thus, a greater number of monocytes at the time of CMV reactivation may account for the preferential expansion of $CD56^{dim}CD57^+$ $NKG2C^+$ NK cells in RIC recipients.

$CD56^{dim}CD57^+$ $NKG2C^+$ NK Cells are Highly Functional Against the K562 Myeloid Leukemia Cell Line.

Figure 4A:
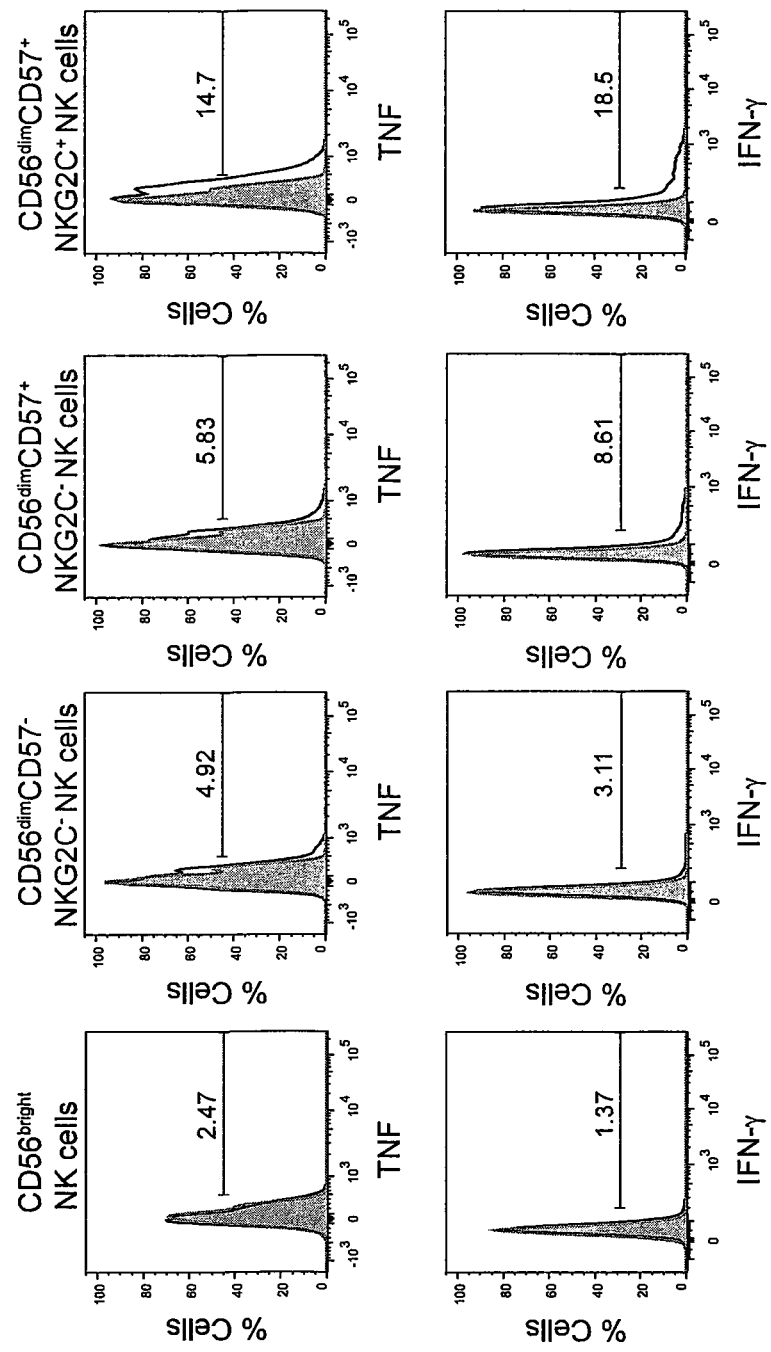
FIG. 4A. Histograms of TNF expression (open black lines) and intracellular IFN-γ expression (open black lines) in NK cells cultured with K562 targets compared to effector cells cultured alone (shaded grey lines) for a representative donor.
Figure 4B:
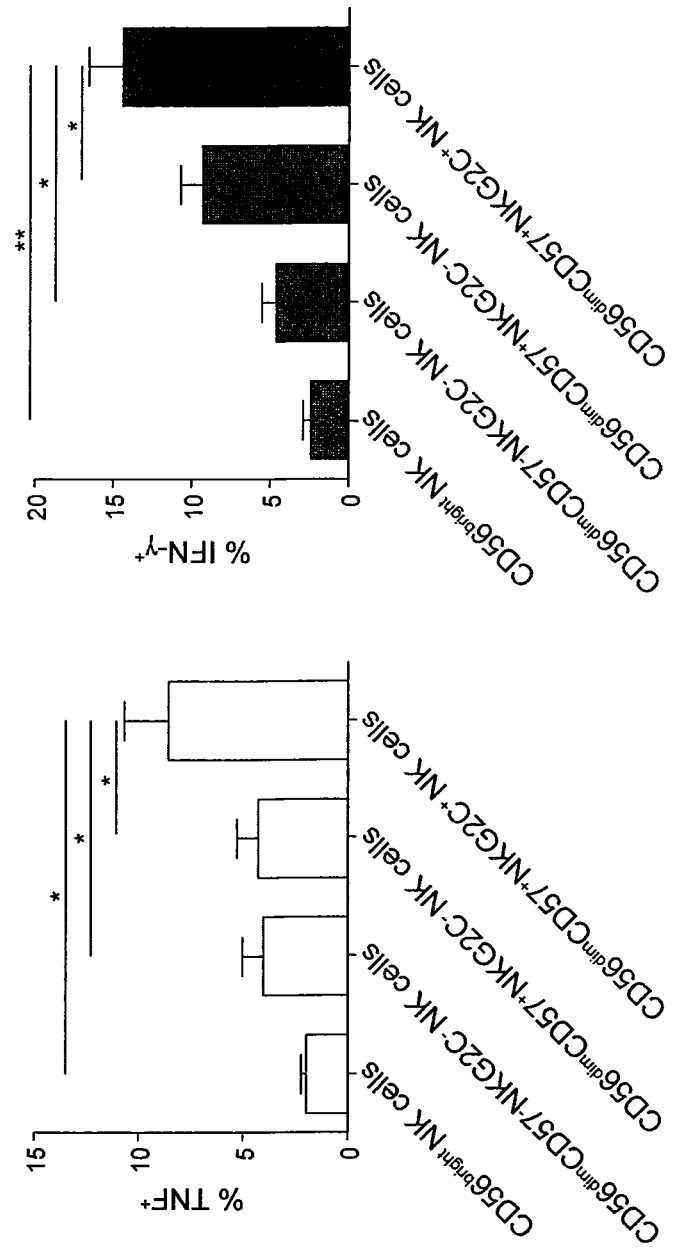
FIG. 4B. Cumulative TNF and IFN-γ expression data in NK cells cultured with K562 targets from 5 donors. Two independent experiments were performed. *=p≤0.05, **=p≤0.005. Two-sided, paired t-tests were used to determine significance. Error bars represent SEM.

To determine whether $CD56^{dim}CD57^+$ $NKG2C^+$ NK cells mediate heightened effector functions against leukemia targets relative to other NK cell subsets, peripheral blood mononuclear cells (PBMCs) were isolated from healthy CMV-seropositive blood donors and cultured at a 2:1 ratio with K562 myeloid leukemia cells. Tumor necrosis factor (TNF) and IFN-γ production were analyzed in immature $CD56^{bright}$ NK cells, early mature $CD56^{dim}CD57^-$ $NKG2C^-$ NK cells, late mature $CD56^{dim}CD57^+$ $NKG2C^-$ NK cells and adaptive $CD56^{dim}CD57^+$ $NKG2C^+$ NK cells. Relative to all other subsets analyzed, $CD56^{dim}CD57^+$ $NKG2C^+$ NK cells exhibited a higher frequency of both TNF and IFN-γ production in response to K562 cells (FIG. 4A, FIG. 4B). No significant differences were observed for NK cell degranulation, as determined by CD107a surface expression (not shown). Thus, $CD56^{dim}CD57^+$ $NKG2C^+$ NK cells likely contribute to relapse protection post-HCT directly through enhanced inflammatory cytokine production upon direct recognition of tumor targets.

Prior to this study, the mechanisms underlying the association between CMV reactivation and relapse protection have remained obscure. Here, it is shown that $CD56^{dim}CD57^+$ $NKG2C^+$ NK cells expand preferentially in reduced intensity recipients after CMV reactivation, and the expansion of these cells is directly associated with lower leukemia relapse.

Example 2

Methods
OP9 Native and OP9-DL1 Cells
OP9 stromal cells transduced with either the empty MigR1 retroviral vector (OP9 native) or with the MigR1 retroviral vector containing the Delta-like 1 gene (OP9-DL1) (Schmitt et al. *Immunity.* 2002; 17(6):749-756) were cultured in MEMα media+20% fetal bovine serum (FBS) at a concentration of 4×10$^5$ cells/well in 24-well plates for two days to allow for cell adherence. Plates were then irradiated with 2,000 cGy to stop cell proliferation.

Cord Blood-Derived NK Cell Culture on OP9 Cells

Mononuclear cells were isolated from whole cord blood by density gradient centrifugation. T cells and B cells were depleted by positive magnetic selection using anti-CD3 and anti-CD19 microbeads, respectively. CD3/CD19-depleted cells were then added to irradiated OP9 cells at a concentration of 5×10$^5$ cells/well and cultured for 14 days in RPMI media+10% FBS supplemented with either 1 ng/mL IL-15 or 10 ng/mL IL-15 with or without 50 ng/mL IL-21.

Phenotypic Analysis of NK Cells Before and after Culture

Cord blood-derived NK cells were analyzed before culture and after 7 and 14 days of culture by fluorescence activated cell sorting (FACS) using the following extracellular and intracellular antibodies: BV785-conjugated anti-CD3 (BioLegend, San Diego, Calif.), PE-Cy7-conjugated anti-CD56 (BioLegend, San Diego, Calif.), BV605-conjugated anti-CD57 (BioLegend, San Diego, Calif.), APC-conjugated SYK (eBioscience, San Diego, Calif.), and PE-conjugated anti-PLZF (BD Biosciences, San Jose, Calif.).

Results

Establishment of an In Vitro Culture System to Support the Expansion of Terminally Differentiated Canonical CD50$^{dim}$CD57$^+$ NK Cells and Adaptive CD56$^{dim}$SYK$^-$ NK Cells The Notch signaling pathway plays an essential role in effector CD8$^+$ T cell differentiation and controls the acquisition of effector function (Backer et al. *Nat Immunol.* 2014; 15(12):1143-1151). To determine if Notch signaling could play a role in driving the differentiation and expansion of terminally differentiated and adaptive NK cell subsets, CD3/CD19-depleted mononuclear cells were cultured from cord blood on native OP9 stromal cells or OP9 stromal cells stably transduced with the Notch ligand DL1 in the presence of low-dose (1 ng/mL) IL-15 or high-dose (10 ng/mL) IL-15 with or without IL-21 (50 ng/mL). Cells were harvested at days 7 and 14, and CD56$^+$ NK cells were analyzed by fluorescence activated cell sorting (FACS) for expression of CD57 and SYK. Prior to culture, an average of 2.13%±0.44 of CD56$^+$ NK cells expressed CD57. No expansion of CD57$^+$ NK cells was observed in OP9 native cultures with either low-dose IL-15 (0.59%±0.19) or high-dose IL-15 (0.70%±0.23) at day 7. Similarly, no expansion of CD57$^+$ NK cells was observed in OP9 native cultures with either low-dose IL-15 (0.24%±0.11) or high-dose IL-15 (0.22%±0.10) at day 14. No expansion of CD57$^+$ NK cells was observed in OP9-DL1 cultures with either low-dose IL-15 (0.91%±0.34) or high-dose IL-15 (1.30%±0.31) at day 7. Similarly, no expansion of CD57$^+$ NK cells was observed in OP9-DL1 cultures with either low-dose IL-15 (0.93%±0.40) or high-dose IL-15 (0.86%±0.44) at day 14. No expansion of CD57$^+$ NK cells was observed in OP9 native cultures with either low-dose IL-15 plus IL-21 (0.71%±0.24) or high-dose IL-15 plus IL-21 (1.05%±0.29) at day 7. Similarly, no expansion of CD57$^+$ NK cells was observed in OP9 native cultures with either low-dose IL-15 plus IL-21 (0.18%±0.06) or high-dose IL-15 plus IL-21 (2.74%±1.90) at day 14. No expansion of CD57$^+$ NK cells was observed in OP9-DL1 cultures with low-dose IL-15 plus IL-21 (2.06%±0.66) at day 7. Moderate expansion of CD57$^+$ NK cells was observed in OP9-DL1 cultures with high-dose IL-15 plus IL-21 (5.31%±2.10) at day 7. No expansion of CD57$^+$ NK cells was observed in OP9-DL1 cultures with low-dose IL-15 plus IL-21 (1.38%±0.56) at day 14. Robust expansion of CD57$^+$ NK cells was observed in OP9-DL1 cultures with high-dose IL-15 plus IL-21 (12.67%±5.11) at day 14.

Figure 5A:
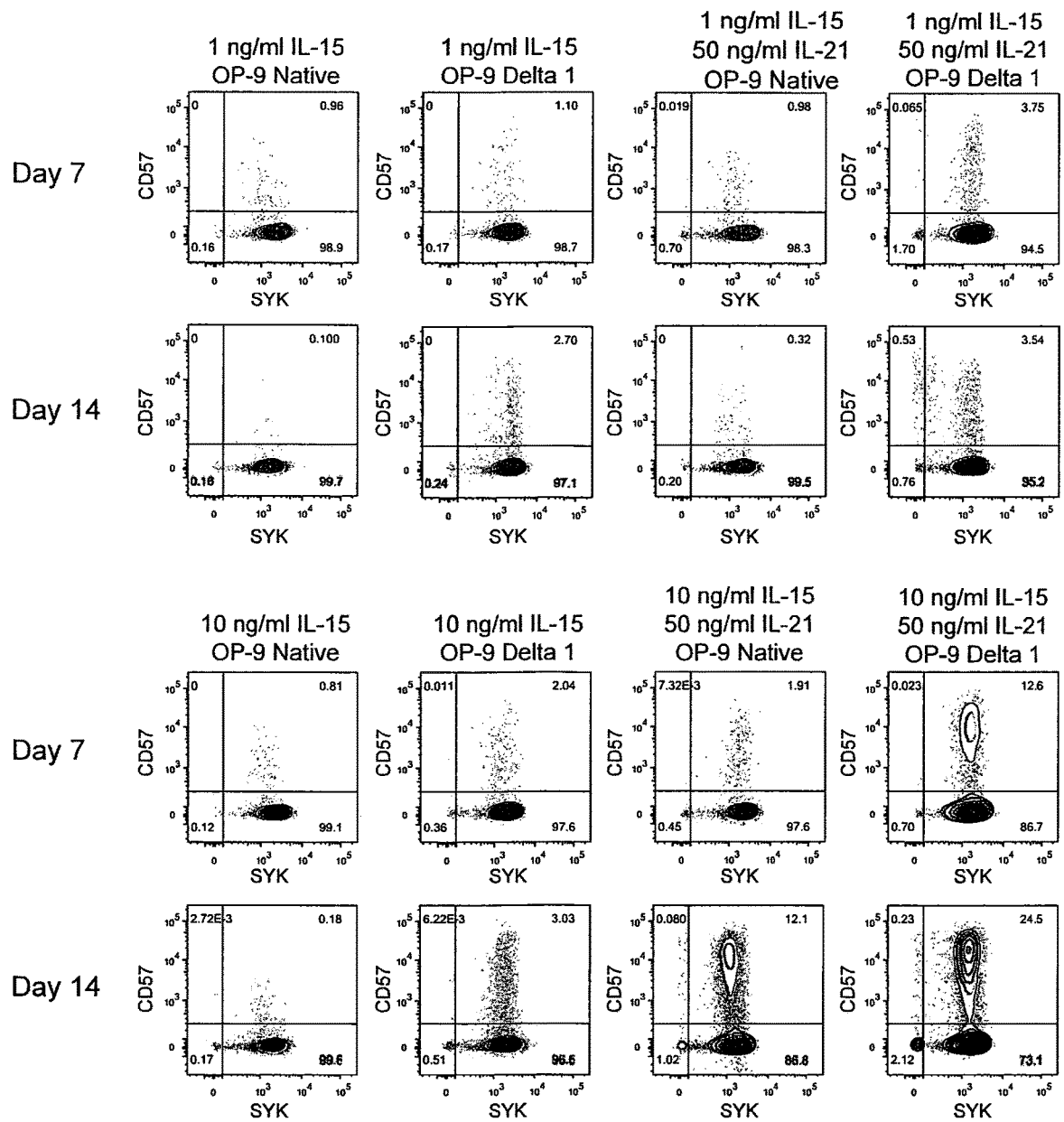
FIG. 5A. Fluorescence-activated cell sorting (FACS) plots of CD57 and SYK expression by $CD56^{dim}$ NK cells at days 7 and 14 in each culture condition from a representative donor. Also shown is cumulative data of the percentage of $CD56^{dim}$ NK cells expressing surface CD57 (FIG. 5B) and lacking intracellular SYK (FIG. 5C) from 6 cord blood donors after 14 days in culture. Two independent experiments were performed. Error bars represent SEM.
Figure 5B:
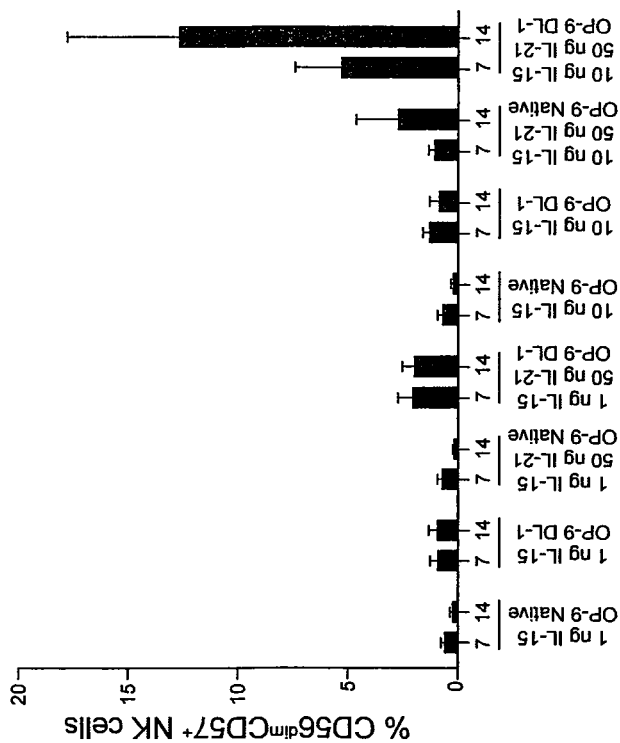
FIG. 5(A-C) shows high dose IL-15, IL-21, and Notch signaling support the expansion of terminally differentiated $CD57^+$ adaptive NK cells and $SYK^-$ adaptive NK cells. Mononuclear cells isolated from cord blood were CD3/CD16-depleted and cultured with the indicated cytokines on native or DL1-transduced OP9 stromal cells for 14 days.
Figure 5C:

Prior to culture, an average of 3.09%±0.91 of CD56$^+$ NK cells lacked expression of SYK. SYK$^-$ NK cells did not expand in OP9 native cultures with either low-dose IL-15 (0.18%±0.06) or high-dose IL-15 (0.21%±0.05) at day 7. Similarly, SYK$^-$ NK cells did not expand in OP9 native cultures with either low-dose IL-15 (0.07%±0.03) or high-dose IL-15 (0.43%±0.15) at day 14. SYK$^-$ NK cells were not maintained in OP9-DL1 cultures with either low-dose IL-15 (0.25%±0.06) or high-dose IL-15 (0.34%±0.04) at day 7. Similarly, SYK$^-$ NK cells did not expand in OP9-DL1 cultures with either low-dose IL-15 (0.17%±0.08) or high-dose IL-15 (0.43%±0.15) at day 14. SYK$^-$ NK cells did not expand in OP9 native cultures with either low-dose IL-15 plus IL-21 (0.39%±0.08) or high-dose IL-15 plus IL-21 (0.31%±0.06) at day 7. Similarly, SYK$^-$ NK cells did not expand in OP9 native cultures with either low-dose IL-15 plus IL-21 (0.16%±0.03) or high-dose IL-15 plus IL-21 (0.60%±0.32) at day 14. SYK$^-$ NK cells did not expand in OP9-DL1 cultures with low-dose IL-15 plus IL-21 (0.77%±0.25) or high-dose IL-15 (0.67%±0.10) at day 7. SYK$^-$ NK cells did not expand in OP9-DL1 cultures with low-dose IL-15 plus IL-21 (0.39%±0.10) at day 14. Expansion of SYK$^-$ NK cells was observed in OP9-DL1 cultures with high-dose IL-15 plus IL-21 (3.31%±1.32) at day 14. Together, these results show that high-dose IL-15 along with IL-21 and Notch ligand are required for expansion of CD56$^{dim}$CD57$^+$ and CD56$^{dim}$SYK$^-$ NK cells in vitro (FIG. 5).

CD56$^{dim}$SYK$^-$ NK Cells Derived from Cord Blood Downregulate PLZF in Response to IL-21

Figure 6A:
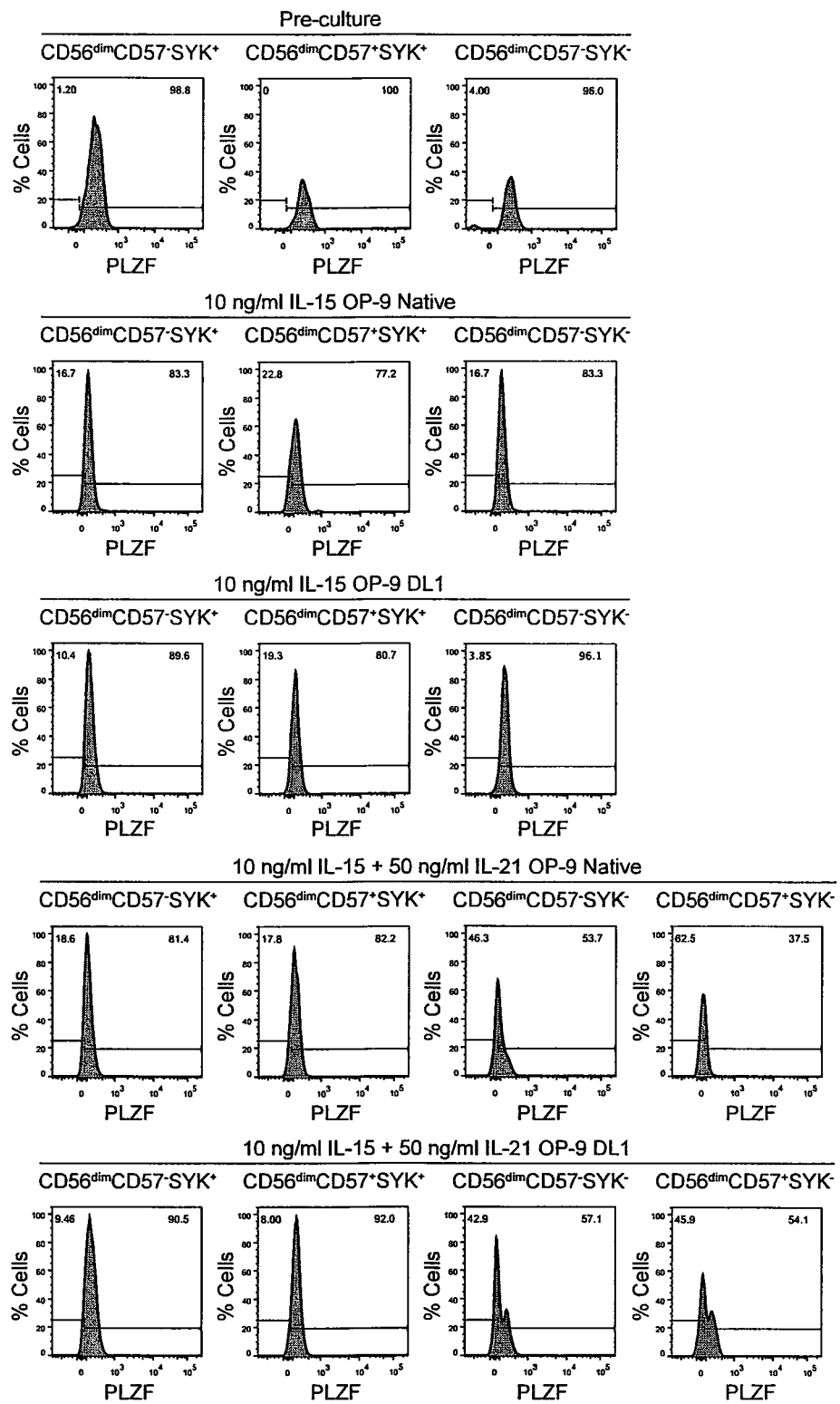
FIG. 6A. FACS plots of intracellular PLZF expression in cord blood-derived $CD56^{dim}$ NK cells from a representative donor after 14 days in the indicated culture conditions.
Figure 6B:
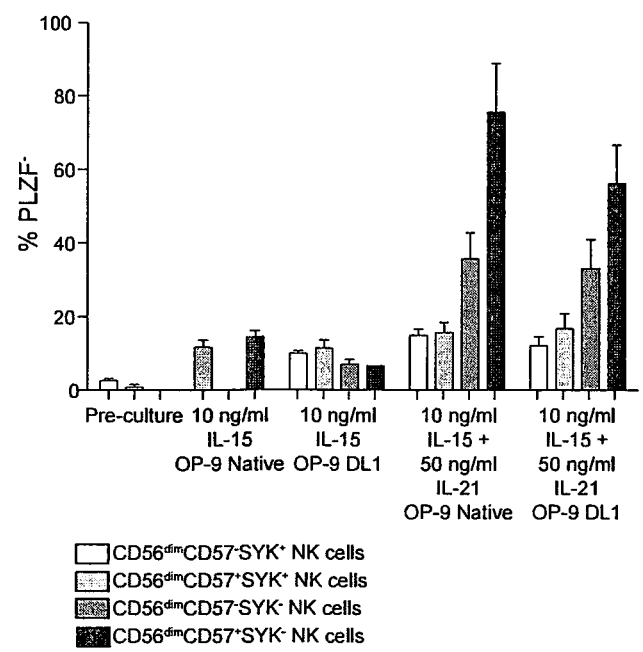
FIG. 6B. Cumulative data showing the percentage of $PLZF^-$ NK cells after 14 days in each culture condition from 6 donors. Two independent experiments were performed. Error bars represent SEM.

Transcriptional silencing of the transcription factor promyelocytic leukemia zinc finger (PLZF) is a hallmark of adaptive NK cells that expand in response to CMV infection (Schlums et al. *Immunity.* 2015; 42(3):443-456). Intracellular staining for PLZF was performed in NK cells from freshly isolated mononuclear cells and from cells that were cultured for 14 days in vitro. Freshly isolated CD56$^{dim}$SYK$^-$ NK cells from cord blood were predominantly PLZF-positive (99.3%±0.10). Culture with high-dose IL-15 led to a modest decrease in PLZF expression in CD56$^{dim}$CD57$^-$ SYK$^+$ NK cells (9.93%±0.75), CD56$^{dim}$CD57$^+$SYK$^+$ NK cells (11.47%±2.18), CD56$^{dim}$CD57$^-$ SYK$^-$ NK cells (7.05%±1.31), and CD56$^{dim}$CD57$^+$SYK$^+$ NK cells (6.67±1.05). However, the addition of IL-21 caused a marked decrease in PLZF expression in CD56$^{dim}$CD57$^-$ SYK$^-$ NK cells (35.82%±7.02) and CD56$^{dim}$CD57$^+$SYK$^-$ NK cells (66.0%±8.86) compared to CD56$^{dim}$CD57$^-$ SYK$^+$ NK cells (14.92%±1.80) and CD56$^{dim}$CD57$^+$SYK$^+$ NK cells (12.13%±2.43). Therefore, IL-21 drives down PLZF expression in CD56$^{dim}$SYK$^-$ NK cells, causing these cells to acquire adaptive characteristics (FIG. 6).

Example 3

Cord-blood derived NK cells, cultured as described in Example 2, are competent of cell cytotoxicity, as indicated by the expression of cell cytotocity receptor 2B4, low affinity Fc receptor CD16, and killer immunoglobulin like receptors (KIR). Additional data (not shown) indicates that these cells express high levels of granzyme and perforin, indicating a capacity to degranulate in response to virally infected cells, neoplastic cells and/or autologous, activated immune cells.

Example 4

Figure 7B:
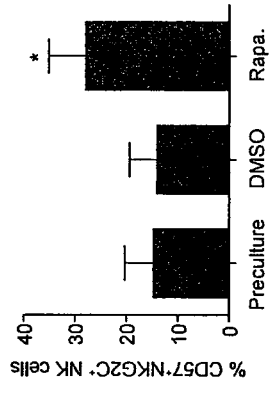
FIG. 7B. Cumulative data showing the percentage of $CD57^+ NKG2C^+$ adaptive NK cells from 4 donors freshly after isolation and after culture. Cells cultured under the conditions described above were analyzed for degranulation (CD107a) and TNF production with or without CD16 stimulation by FACS.
Figure 7A:
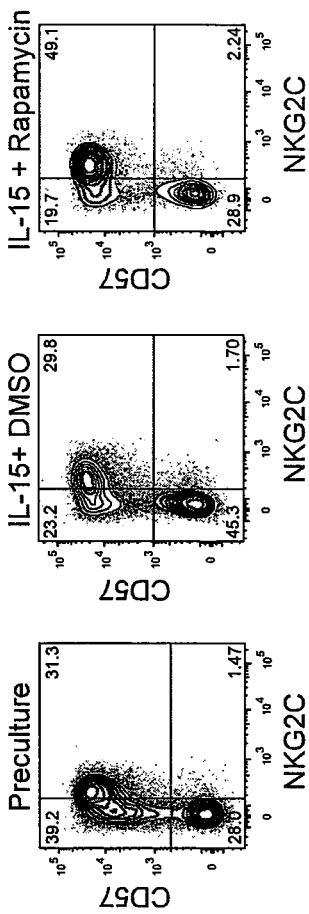
FIG. 7A. FACS plots of CD57 and NKG2C expression from a representative donor.
Figure 7C:
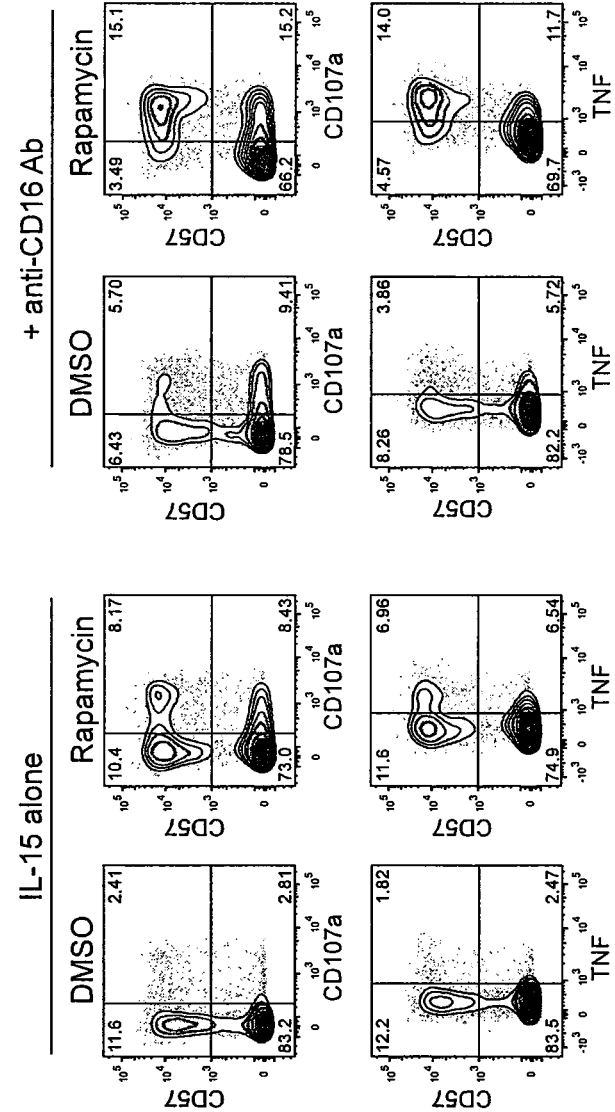
FIG. 7C. FACS plots from a representative donor.
Figure 7D:
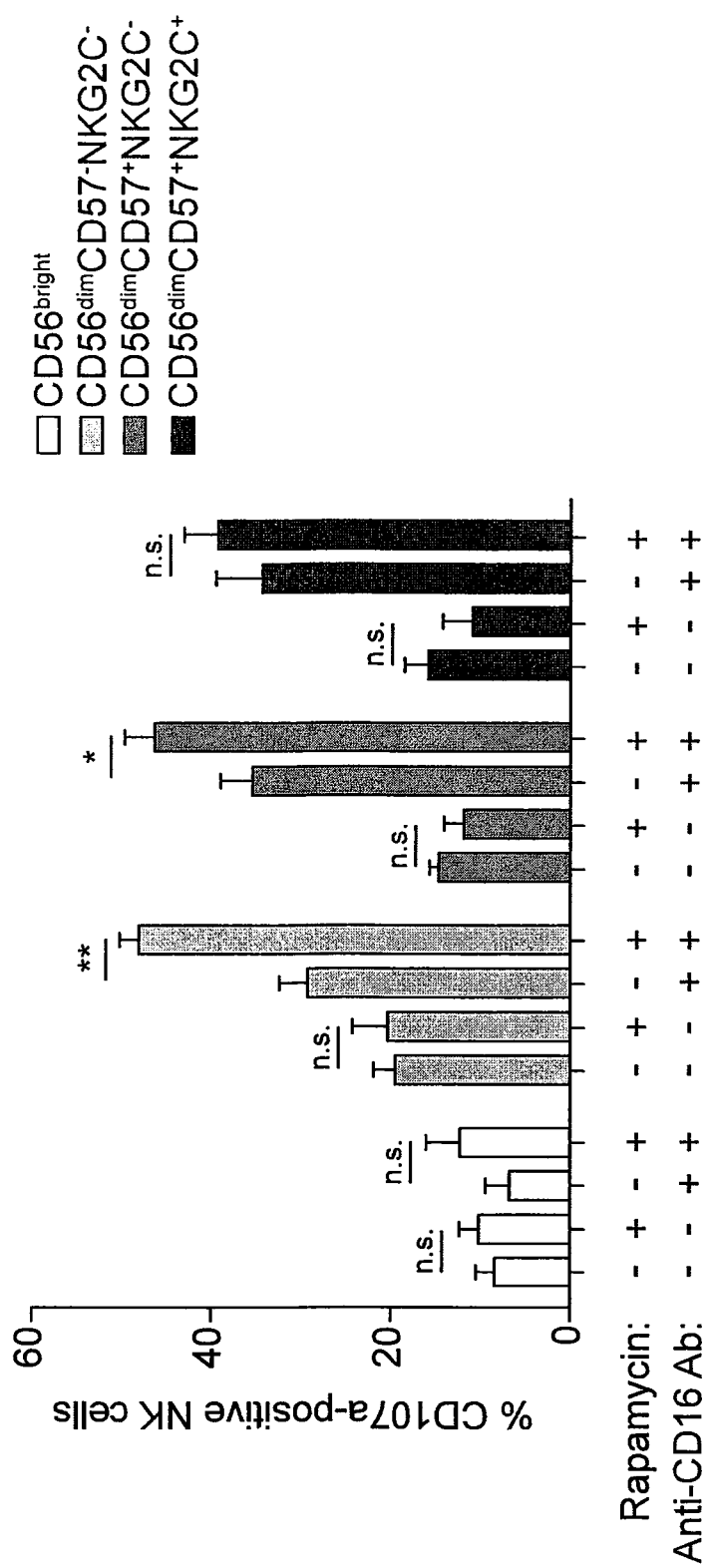
FIG. 7D. Cumulative degranulation data from 4 donors. $*=p<0.05$, $**=p<0.01$.

Addition of rapamycin to NK cells from CMV seropositive donors cultured in vitro accelerated the differentiation program of adaptive NK cells (FIG. 7A, FIG. 7B). In functional assays, NK cells treated with rapamycin exhibited enhanced degranulation and tumor necrosis factor (TNF) production (FIG. 7C, FIG. 7D). Thus, the addition of rapamycin to ex vivo NK cell expansion methods suggests a novel strategy to enhance NK cell differentiation, enrich for mature NK cell subsets with unique metabolic properties and enhance NK cell cytotoxicity and cytokine production prior to adoptive immunotherapy.

Example 5

Figure 8A:
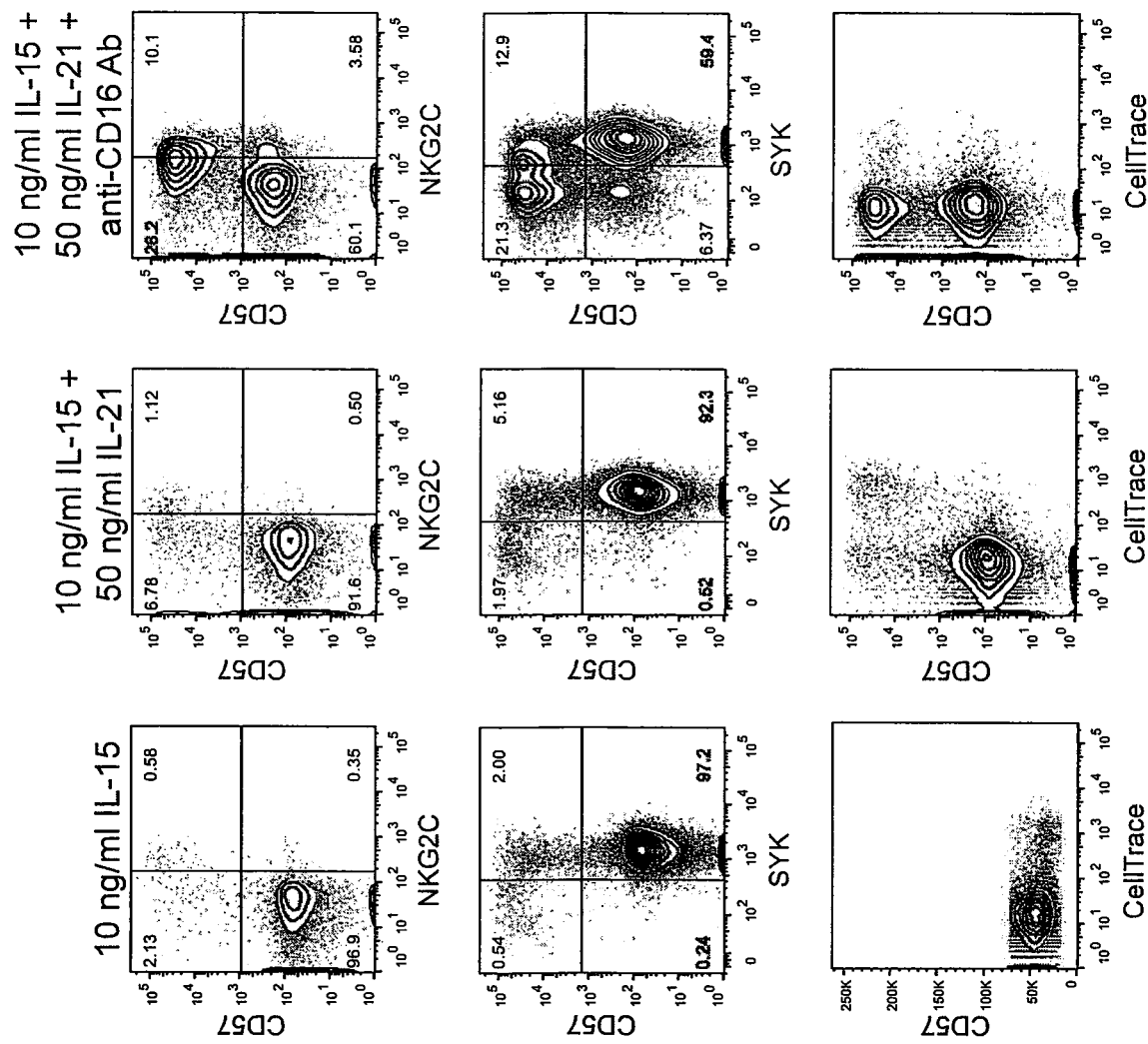
FIG. 8A. FACS plots of CD57 vs. NKG2C, SYK, and CellTrace from a representative CMV seropositive donor. Cumulative data of the percentage of NK cells expressing NKG2C (FIG. 8B) and the percentage of NK cells lacking SYK (FIG. 8C) from 4 CMV seropositive donors. $*=p<0.05$.
Figure 8B:
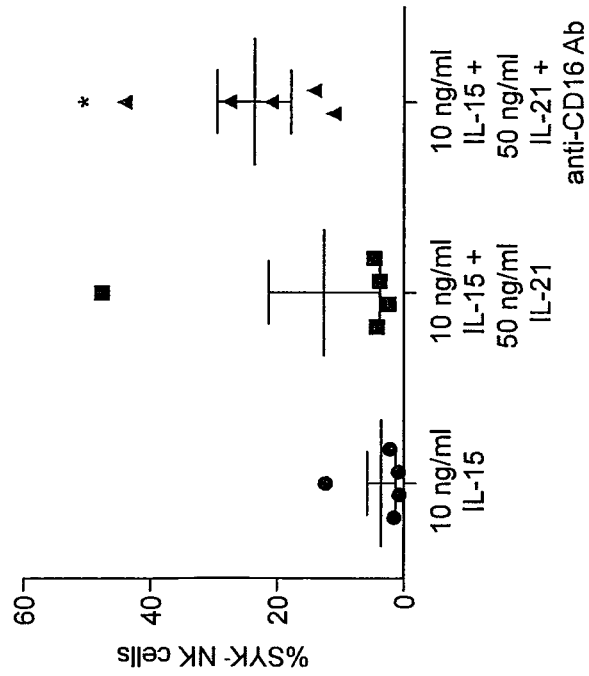
FIG. 8(A-C) shows adaptive NK cells from the peripheral blood of adult CMV seropositive donors can be expanded in vitro with high-dose IL-15, IL-2, and CD16 stimulation.
Figure 8C:
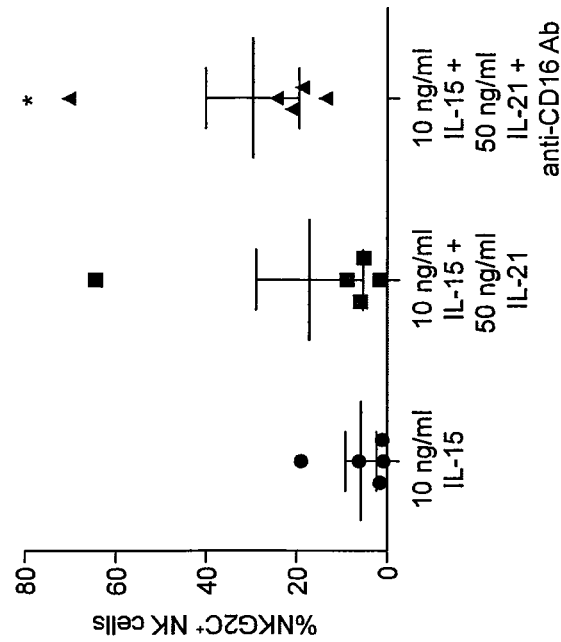

Adaptive NK cells from the peripheral blood of adult CMV seropositive donors can be expanded in vitro with high-dose IL-15, IL-21, and CD16 stimulation. CD3/CD19-depleted PBMCs from healthy CMV seropositive donors were labeled with CellTrace dye and cultured for 10 days with high-dose IL-15 (10 ng/mL) alone, IL-15 plus IL-21 (50 ng/mL), or IL-15 plus IL-21 plus anti-CD16 antibody (1:1000). FIG. 8A shows expression of CD57, NKG2C, SYK, and CellTrace from a representative CMV seropositive donor. FIG. 8B shows cumulative data of the percentage of NK cells expressing NKG2C. FIG. 8C shows the percentage of NK cells lacking SYK from 4 CMV seropositive donors.

Example 6

To induce NKG2C expression, NK cells will be cultured for 7 days and 14 days, as described in Example 2, with at least one of: soluble and/or membrane-bound inflammatory cytokines including, for example, IL-1, TNF-α, IL-6, IL-8, and IFN-γ; membrane-bound HLA-E; and membrane bound HLA-E presenting CMV peptides.

Example 7

Adaptive NK Cells with Low TIGIT Expression are Resistant to Myeloid-Derived Suppressor Cells
Introduction Natural killer cells are lymphocytes of the innate immune system. Unlike T cells and B cells, they do not express germline rearranged antigen-specific receptors in a clonal manner. Although they share similar mechanisms of killing with cytotoxic T cells, NK cells recognize targets through families of activating and inhibitory receptors. The balance between these receptors determines the final function of NK cells. The dominant paradigm of how NK cells distinguish between healthy and transformed or infected cells is explained by the "missing self" hypothesis. A down-regulation of MHC class I on damaged cells, or a mismatch between inhibitory subgroups of killer immunoglobulin-like receptors (KIRs) and their respective human leukocyte antigen (HLA) ligands on self-cells will render target cells susceptible to NK cell killing. NK cells also have the ability to recognize and kill tumor cells without the requirement of prior antigen exposure, a property which facilitates the development of NK cells as effectors for cancer therapies. However, like T cells, NK cell anti-tumor activity is limited by the suppressive factors present in the tumor microenvironment, which leads to dampened immunological function and poor prognosis. Emerging studies indicate that inhibitory receptors such as cytotoxic T lymphocyte-associated 4 (CTLA-4), programmed cell death 1 (PD-1) and T cell Ig and ITIM domain (TIGIT) on T and NK cells can suppress anti-tumor responses.

In the present study, the interaction between adaptive NK cells and myeloid-derived suppressor cells (MDSCs) was examined. MDSCs are a heterogeneous population of myeloid progenitor cells and immature myeloid cells. In humans, MDSCs commonly express CD11b, CD33, low or no HLA-DR and are either CD14+(monocytic MDSCs [mMDSCs]) or CD15+CD66b+(granulocytic MDSCs [gMDSCs]) (Marvel et al. The Journal of Clinical Investigation. 2015; 125(9):3356-64). These cells are induced by tumors and contribute to inhibition of both innate and adaptive anti-tumor immunity by producing TGF-β, IL-10, reactive oxygen species (ROS), and arginase (Ostrand-Rosenberg et al. Journal of Immunology. 2009; 182(8): 4499-506). However, a subset of NK cells, adaptive NK cells, which can be isolated and/or prepared using the methods and compositions disclosed herein, exhibits resistance to functional suppression by cancer patient-derived MDSCs. Compared to conventional NK cells, adaptive NK cells express lower levels of TIGIT, an inhibitory receptor known for direct regulation of effector T cell responses.

Results
MDSCs Suppress T and NK Cell Proliferation and NK Cell Function

Figure 9A:
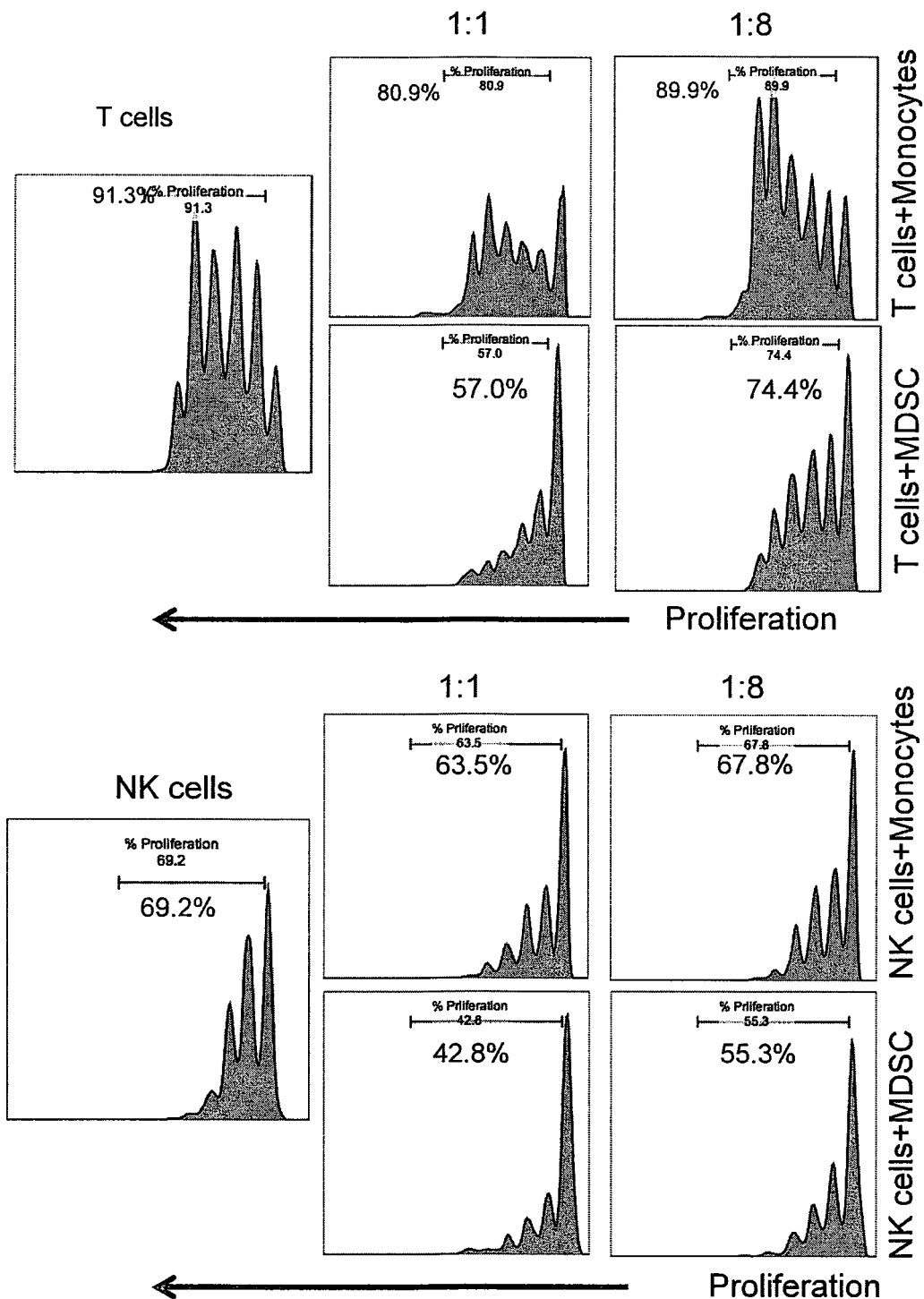
FIG. 9A. Purified T and NK cells from healthy blood donors were labeled by CellTrace Violet and co-cultured with cytokine-induced autologous MDSCs or freshly isolated monocytes at different ratios in the presence of CD3/CD28 beads (40 beads/$1\times10^5$ cells) and IL-15 (1 nanograms per milliliter (ng/mL)) for T cells or IL-15 (10 ng/mL) alone for NK cells. Proliferation was assessed on day 3 or 4, and representative data is shown of six independent experiments.
Figure 9B:
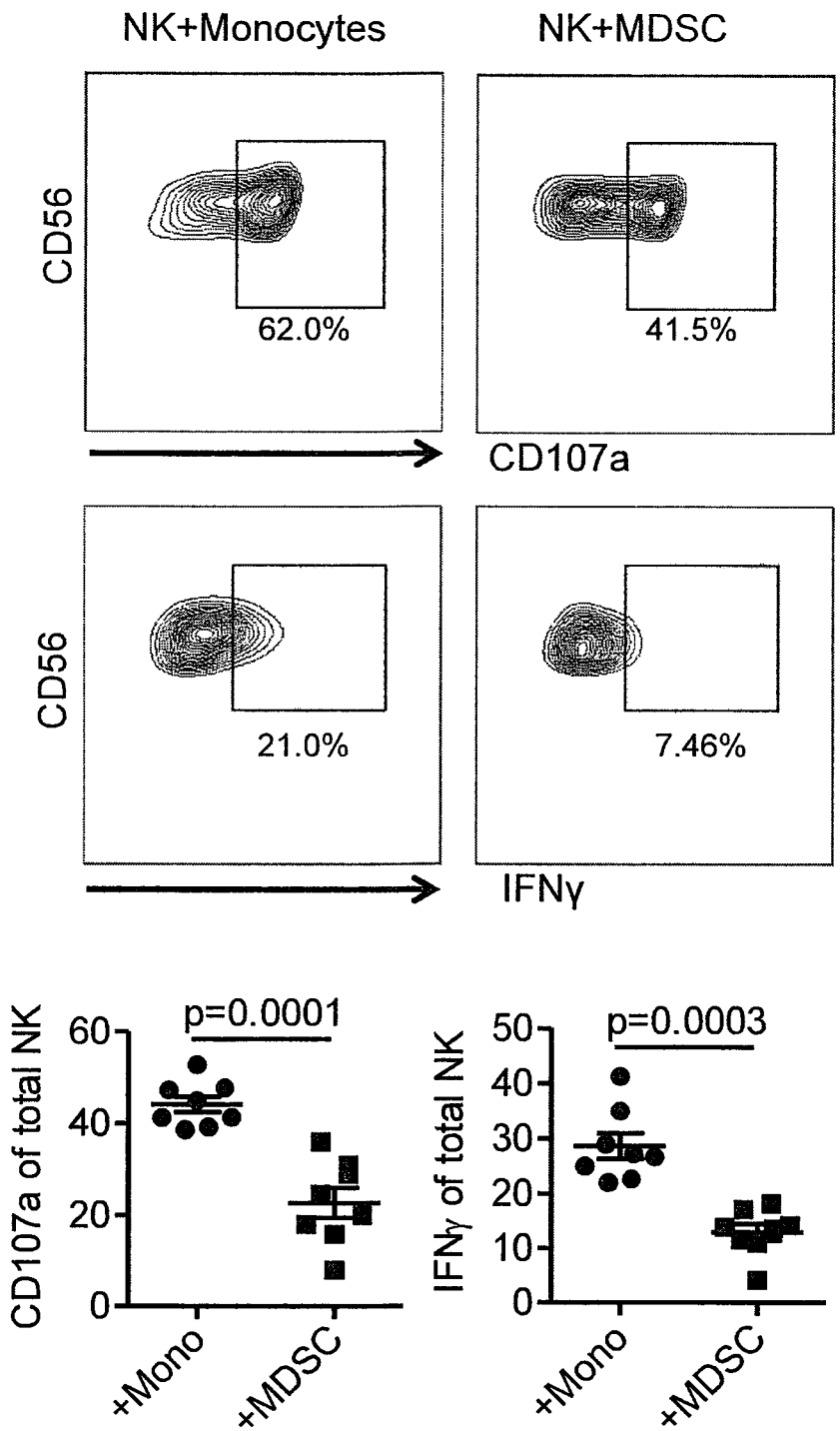
FIG. 9B. Purified NK cells were co-cultured with monocytes or MDSCs at a 2:1 ratio in the presence of IL-15 (10 ng/mL) for 5 days. Cells were stimulated with agonistic CD16 (anti-CD16; 1 micrograms per milliliter (µg/mL)) for 6 hours prior to staining and evaluated for degranulation (CD107a) and IFN-γ production. One representative contour-plot and cumulative (n=8) data are shown as mean±SEM. The Student's t-test was used for statistical analysis.
Figure 16A:
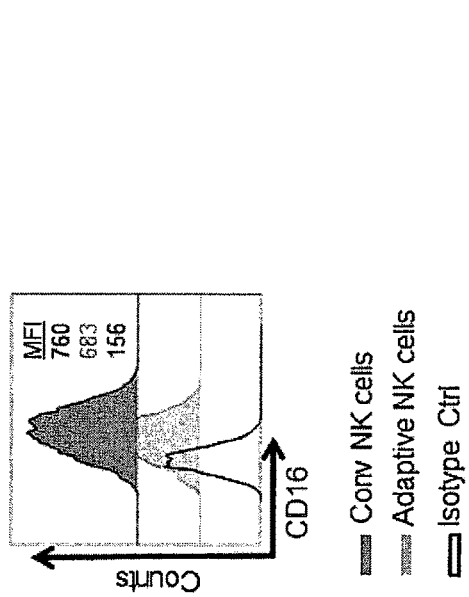
FIG. 16A Representative phenotype of in vitro induced MDSCs and freshly isolated monocytes.

To investigate the interaction between MDSCs and NK cell subsets, MDSCs were generated by culturing peripheral blood mononuclear cells from healthy donors with IL-6 and GM-CSF for one week, followed by enrichment of $CD33^+$ cells (FIG. 16A). Fresh monocytes were used as a myeloid cell control for these experiments. Purified T and NK cells were co-cultured with monocytes or MDSCs at different ratios and evaluated for proliferation following 3-4 days of culture. While monocytes had a little effect on proliferation, MDSCs induced a 2.7±1.6-fold T cell suppression (p=0.005) of proliferation with a similar effect on NK cells (1.5±0.27-fold suppression, p=0.006) (FIG. 9A). Similarly, CD16 engagement stimulated NK cell degranulation and IFN-γ production that was significantly suppressed by MDSC (2.4±1.4 fold suppression, p=0.0001 and 2.6±1.5 fold suppression, p=0.003, respectively) relative to NK cells cultured with fresh monocytes (FIG. 9B).

Adaptive NK Cells Resist MDSC Suppression

Figure 10A:
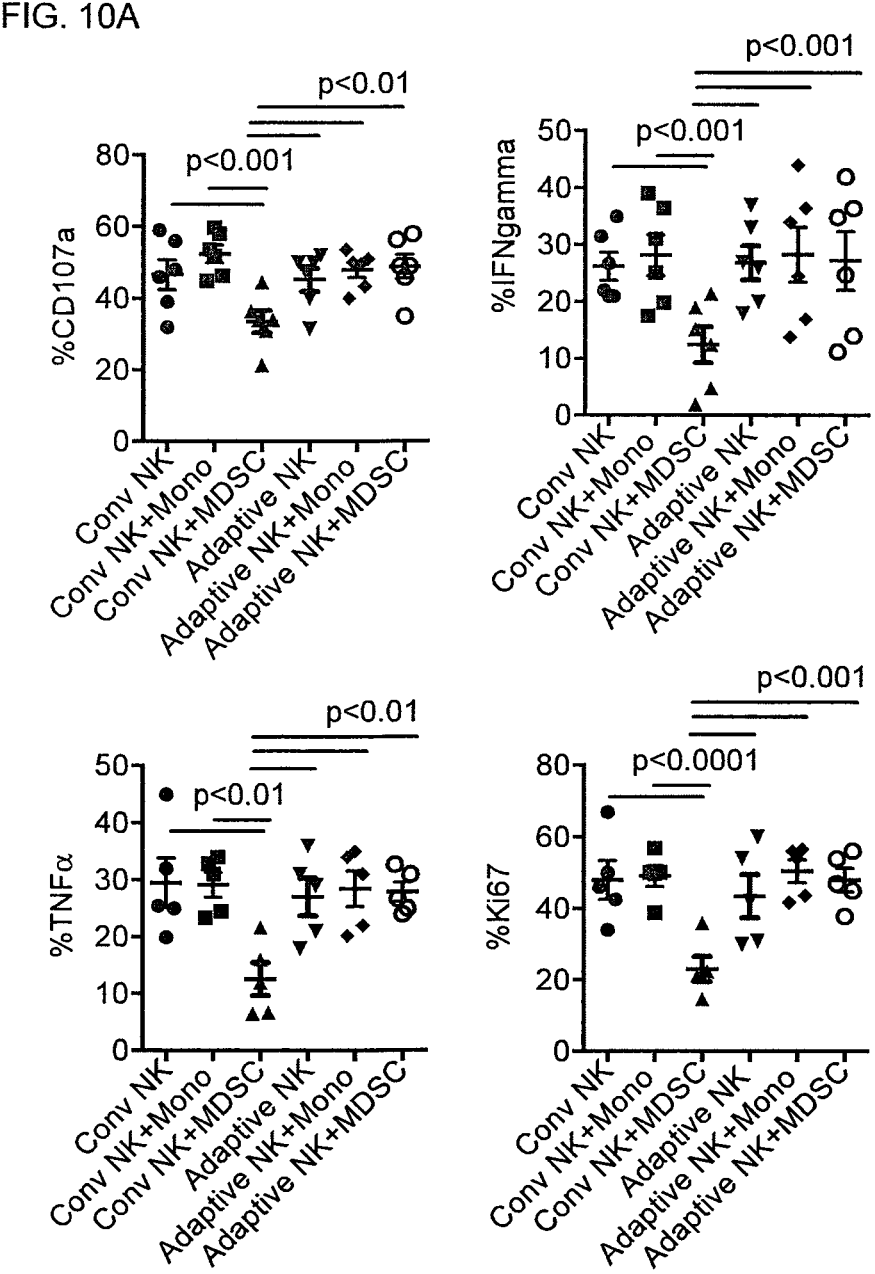
FIG. 10(A-B) shows adaptive NK cells resist MDSC suppression. Purified NK cells from healthy blood donors were co-cultured with autologous MDSCs or freshly isolated monocytes at a 2:1 ratio in the presence of IL-15 (10 ng/mL) for 5 days in cell contact (FIG. 10A) or in transwells (FIG. 10B) allowing soluble factor exchange only. Cells were stimulated with anti-CD16 six hours prior to staining, and degranulation, IFN-γ (FIG. 10A, FIG. 10B) and TNF-production (FIG. 10A), and proliferation (Ki67) (FIG. 10A) were each assessed by flow cytometry. Conventional (Conv) NK cells are identified as $CD56^+CD3^-CD57^+ NKG2C^-$ and adaptive NK cells as $CD56^+CD3^- CD57^+ NKG2C^+Fc\epsilon R\gamma^-$. Pooled data of 5-7 independent experiments are shown as the mean±SEM and statistical analysis were done using the Student's t-test.
Figure 10B:
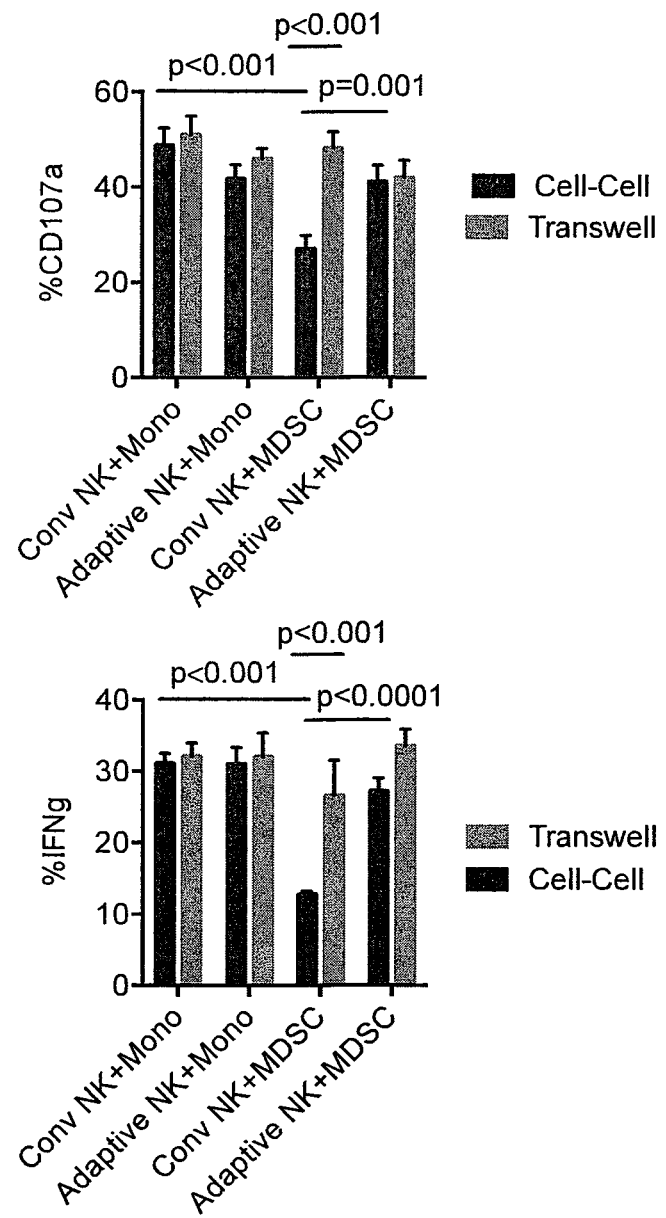
Figure 16B:
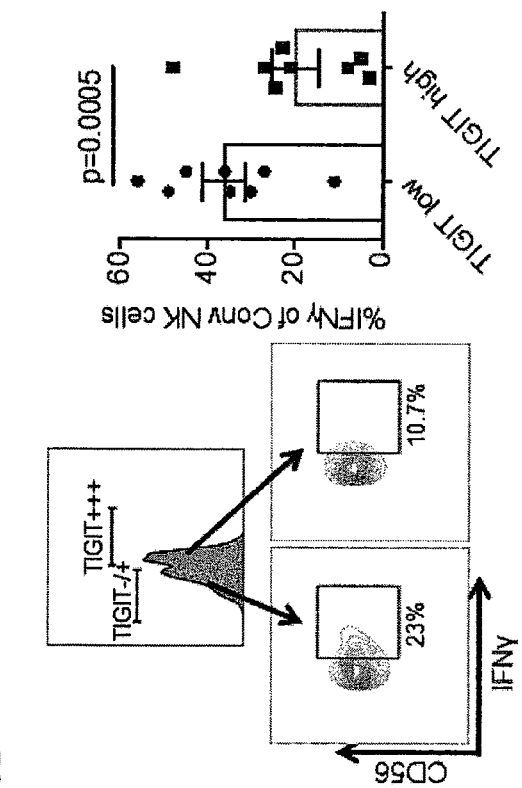
FIG. 16B. NK cells were cultured in the presence of IL-15 (10 ng/ml) for 5 days and representative histograms is showing of the expression of CD16 in conv vs adaptive NK cells. Mean fluoresces intensity (MFI) is shown.

To examine whether adaptive NK cells could resist MDSC suppression compared with conventional NK cells, purified polyclonal NK cells were co-cultured with monocytes or MDSCs at 2:1 ratio for 5 days and examined for degranulation, proliferation and cytokine production following CD16 stimulation. Conventional and adaptive NK cells express a similar amount of CD16 (FIG. 16B); adaptive NK cells were defined as NK cells from CMV-seropositive donors that were $CD57^+$ $NKG2C^+FcεRγ^-$ (Schlums et al. Immunity. 2015; 42(3):443-56). Similar NK cell activity was observed when cultured alone or in co-culture with monocytes in the presence of IL-15 (degranulation: 44±14% vs 49±12, IFNγ: 28±14.0% vs 27±9.0%) (FIG. 10A). Compared to monocyte controls, MDSCs mediated significant suppression of CD107a (52.4±2.4% vs. 33.5±3.1%, p=0.0007), IFN-γ (31.3±3.8% vs. 13.8±3.0%, p=0.009), TNF (29.1±2.1% vs. 13.6±3.3%, p=0.007) and proliferation (49.0±2.9% vs. 23.0±3.5%, p=0.001) (measured by Ki67) within the population of conventional NK cells. However, adaptive NK cells were resistant to the same MDSC population (FIG. 10A). Moreover, conventional NK cell degranulation and IFNγ, in the presence of MDSC, were completely restored when separated by transwell (FIG. 10B). Thus, CMV infection gives rise to a population of adaptive NK cells that are resistant to MDSC suppression.

Figure 11A:
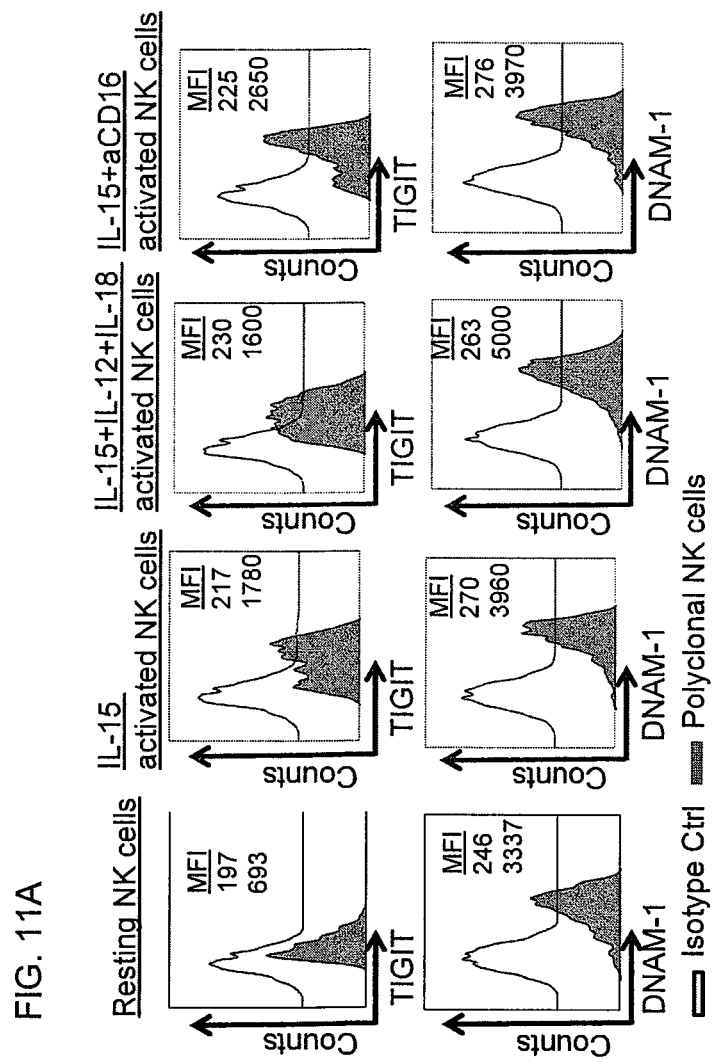
FIG. 11A. Purified NK cells from healthy blood donors were cultured before staining in the absence or presence of IL-15 (10 ng/mL) alone or with the additional stimulation of IL-12 (10 ng/mL) and IL-18 (100 ng/mL) for 18 hours or with stimulation with anti-CD16 (1 µg/mL) for 6 hours. One of four independent experiments is shown. NK cells were cultured with autologous MDSCs or freshly isolated monocytes at a 2:1 ratio in presence of IL-15 (10 ng/mL) for 5 days. Cells were stimulated with anti-CD16 six hours prior to analysis. Representative histograms for DNAM-1 (FIG. 11B) and TIGIT expression (FIG. 11C) and aggregate data for TIGIT expression (n=8) are shown as mean fluorescence intensity (MFI)±SEM. Two-Way ANOVA was used for statistical analysis.
Figure 11B:
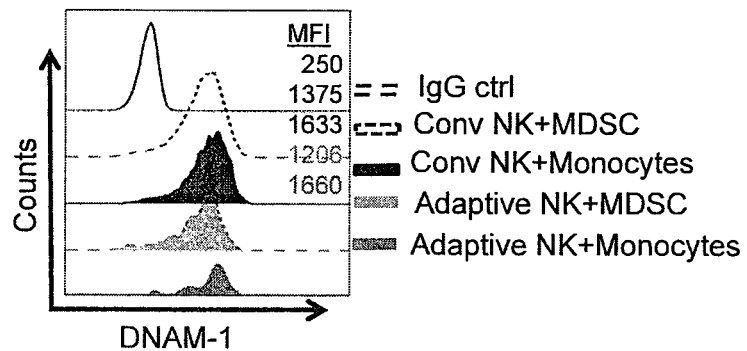
FIG. 11(A-D) shows conventional NK cells express higher TIGIT compared to adaptive NK cells.
FIG. 11D. NK cells before and after co-culture with monocytes or MDSC were analyzed for co-expression of DNAM-1 and TIGIT. Representative data is shown of 3 independent experiments and 7 replicates.
Figure 11C:
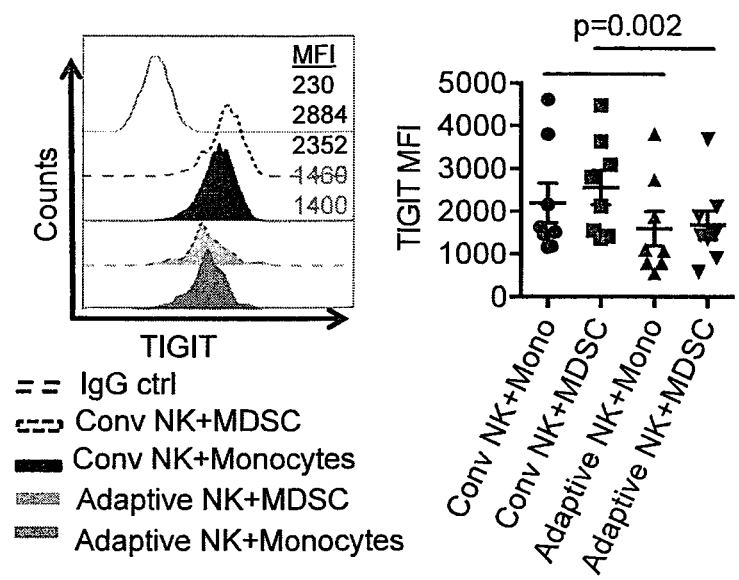
Figure 11D:
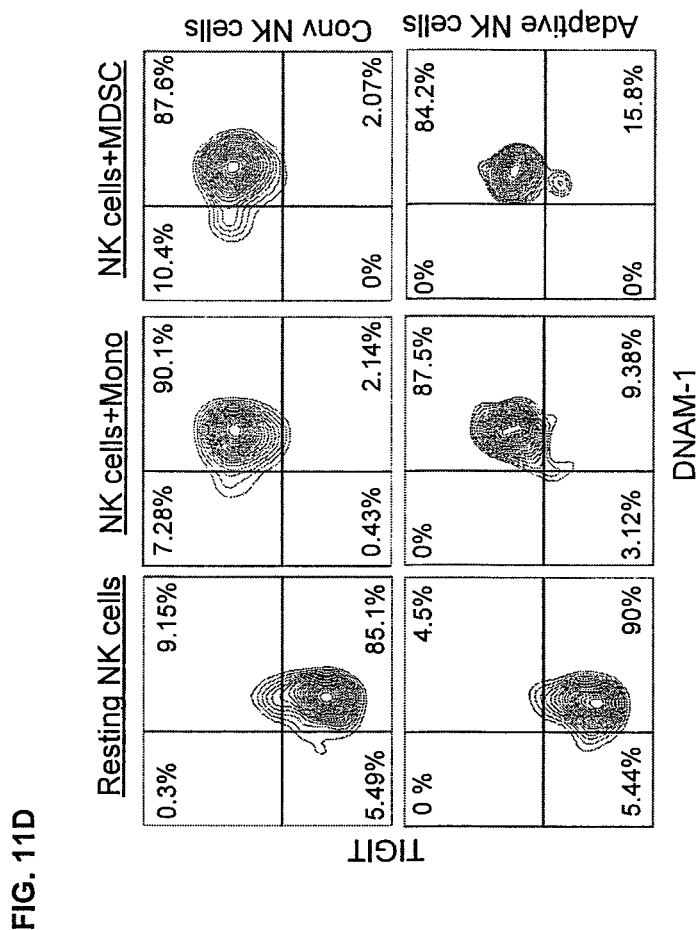
Figure 16C:
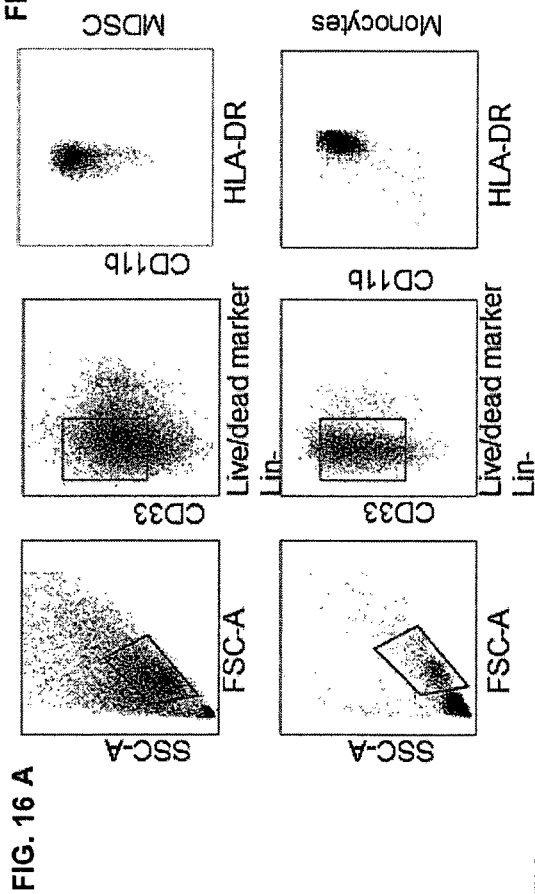
FIG. 16C. NK cells were cultured with autologous MDSC or freshly isolated monocytes at 2:1 ratio in presence of IL-15 (10 ng/mL) for 5 days. Six hours prior to staining, cells were stimulated with anti-CD16; cells were analyzed by flow cytometry. Representative histograms are shown as mean fluorescence intensity (MFI).

Adaptive NK Cell Resistance to MDSC Suppression Correlates with Lower TIGIT Expression Purified NK cells from healthy blood donors were cultured overnight in the absence or presence of IL-15 (10 ng/mL) alone or with the additional stimulation of IL-12 (10 ng/mL) and IL-18 (100 ng/mL) or anti-CD16 (1 µg/mL) prior to staining. TIGIT expression was low without stimulation and was slighted upregulated with IL-15 alone. Additional stimulation by anti-CD16 further increased TIGIT expression. However, DNAM-1 could not be further increased due to high baseline expression level (FIG. 11A). The staining pattern for TIGIT on these polyclonal activated NK cells showed bi-modal expression (FIG. 11A). To explore this phenomenon further, the expression of TIGIT and other inhibitory receptors on adaptive and conventional NK cells was examined. There were no expression differences between adaptive and conventional NK cells for DNAM-1, CD96, NKp44, NKp46, PD-1, Tim3, or NKG2A (FIG. 11B, FIG. 16C). In contrast, TIGIT expression was significantly less on adaptive vs. conventional NK cells whether co-cultured with monocytes (TIGIT MFI: 1595±407 vs. 2196±461, p=0.008) or MDSCs (TIGIT MFI: 1680±336 vs. 2556±403, p=0.008) (FIG. 11C). Although conventional and adaptive NK cells co-expressed TIGIT and DNAM-1 at similar levels before and after co-culture with monocytes or MDSC (NK alone: 18%±10% vs. 14%±11.5%, NK+ monocytes: 86%±8% vs. 83%±9%, NK+MDSC: 84%±9% vs. 82%±6%, FIG. 11D), adaptive NK cell expression of TIGIT remained low.

TIGIT-Dependent Suppression of Conventional NK Cells by MDSCs

Figure 12A:
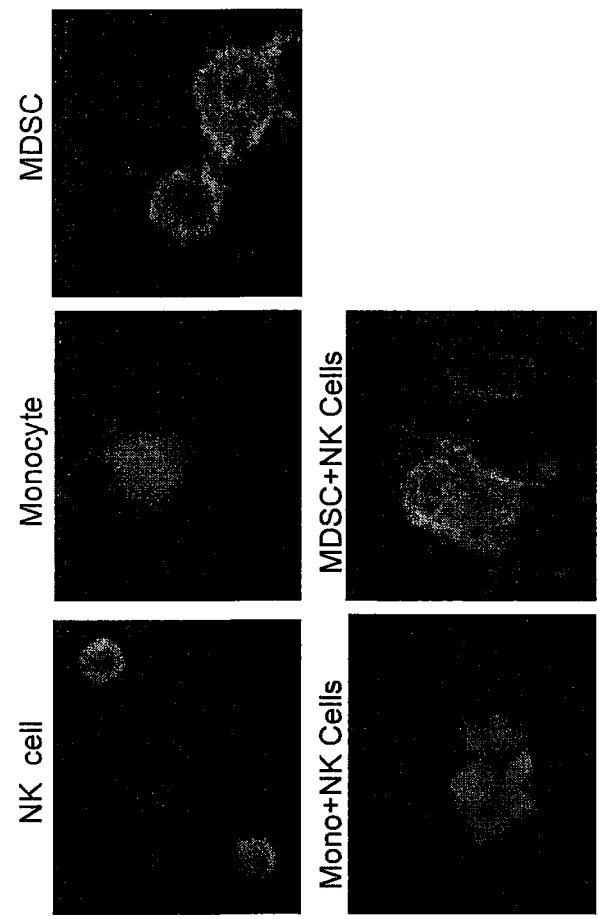
FIG. 12A. Monocytes, MDSCs, and NK cells were labeled with CellTracker Blue, co-cultured on slides overnight then stimulated with anti-CD16 prior to staining with anti-CD155 (green) and anti-TIGIT (red) followed by confocal microscopy. Individual cell types are shown at the upper panel or at the lower panel when co-cultured. Representative data of 2 independent experiments and 6 donors is shown. NK cells were cultured with monocytes or MDSCs in the presence of IL-15 and IgG control (10 ug/ml) or blocking antibodies against TIGIT (10 µg/ml) for 5 days. Degranulation (n=9) and IFN-γ production (n=8) were evaluated in polyclonal NK cells (FIG. 12B), conventional (n=8) (FIG. 12C) and adaptive NK cells (n=9) (FIG. 12D).
Figure 12B:
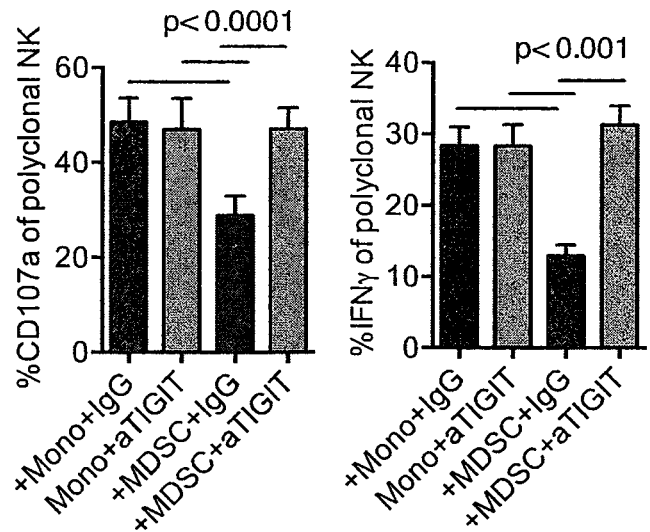
FIG. 12(A-E) shows TIGIT-dependent suppression of conventional NK cells MDSCs.
FIG. 12E. Alternatively, cells were co-blocked by anti-TIGIT and anti-DNAM-1 (10 µg/ml) (n=6). Pooled data are shown as mean±SEM of n number of replicates, and the Two-Way and One-way ANOVA were used for statistical analysis.
Figure 16D:
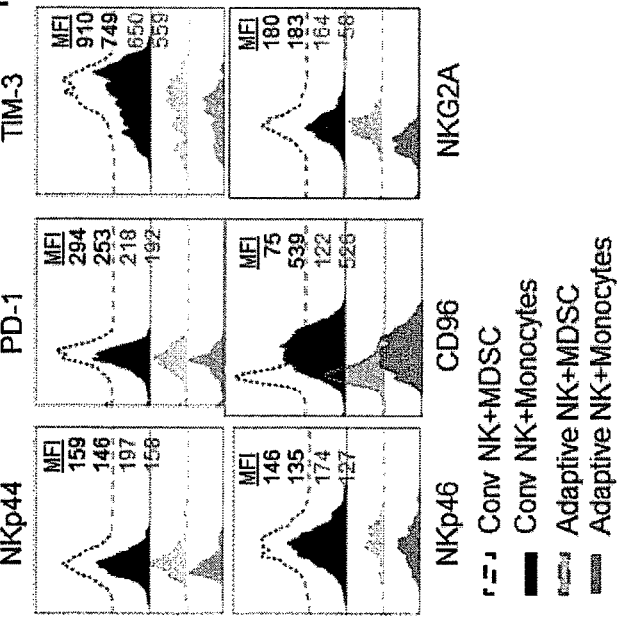
FIG. 16D. Purified NK cells (n=6) from healthy blood donors were co-cultured with autologous monocytes or allogeneic MDSC enriched from the blood of MDS-patients at a 2:1 ratio in the presence of IL-15 (10 ng/mL) for 5 days. Following 6 hours stimulation by anti-CD16, IFN-γ production was evaluated in conventional and adaptive NK cells by flow cytometry. Representative and cumulative data are shown from 8 experiments as mean±SEM. Statistical analysis were done using the Student's t test.

Monocytes, MDSCs, and NK cells were labeled with CellTracker Blue and co-cultured in chamber slides overnight. Cells were stained with anti-CD155 (green) and anti-TIGIT (red) and distinguished by size. As expected, TIGIT on NK cells co-localized with CD155 on MDSCs (FIG. 12A). To assess whether TIGIT plays a role in MDSC-dependent regulation of NK cells, polyclonal NK cells from healthy blood donors were co-cultured with autologous MDSCs or freshly isolated monocytes at a 2:1 ratio in the presence of IL-15 (10 ng/mL) for 5 days. IFN-γ production was evaluated in conventional NK cells co-cultured with MDSCs based on differential high versus low TIGIT expression after 6 hours of CD16 stimulation. These data show that NK cells with low TIGIT expression produce significantly more IFN-γ relative to NK cells with high TIGIT expression (36.2% vs. 19.9%, p=0.0005, FIG. 16D). Next, whether engagement of TIGIT is responsible for driving the MDSC-suppression of NK cells was examined. The function of the anti-TIGIT antibody was tested as previously described (Warren et al. *Int Immunol.* 2001; 13(8):1043-52) in a P815 assay with normal NK cells. While the presence of anti-CD158b control inhibited NK cell cytotoxicity, NK cell function was not affected in the presence of anti-TIGIT (FIG. 18A) indicating the lack of agonistic function.

Figure 12C:
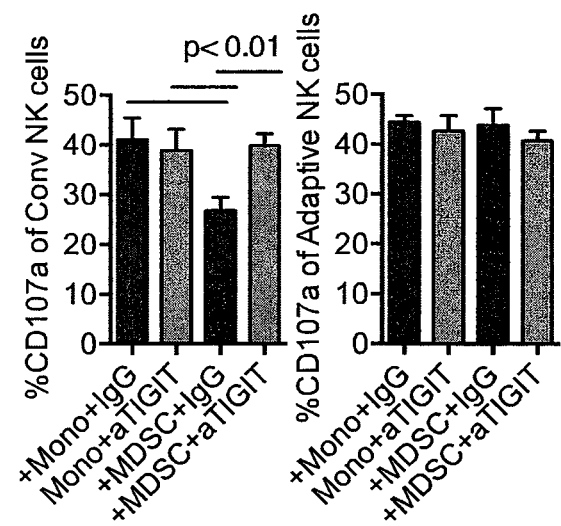
Figure 12D:
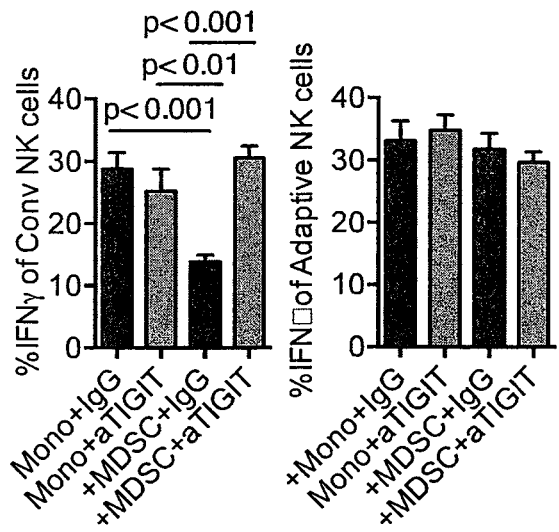
Figure 12E:
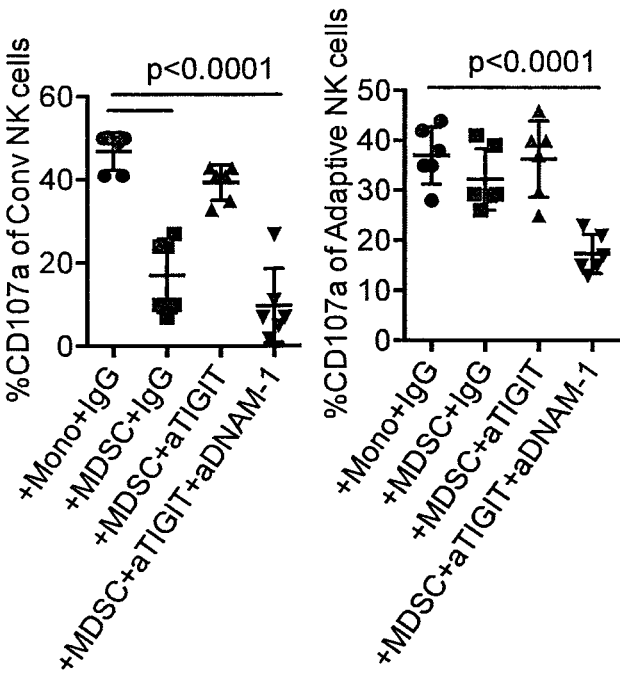

NK cells were co-cultured with monocytes or MDSCs for 5 days in the presence or absence of blocking antibodies against TIGIT. MDSC-induced suppression of polyclonal NK cell function was completely abrogated by blocking TIGIT (FIG. 12C). As TIGIT blockade had little effect on adaptive NK cells, this effect was entirely based on the large conventional NK cell population (FIG. 12C, FIG. 12D). Simultaneous blockade of TIGIT and DNAM-1 in conventional NK cells co-cultured with MDSC reversed the effect of TIGIT-blockade and inhibited the degranulation and IFN-γ of adaptive NK cells (FIG. 12E, FIG. 18B), indicating a TIGIT-dependent inhibition of DNAM-1 signaling.

ROS-Induce CD155 Expression on the Surface of MDSCs

The expression of the TIGIT ligands CD155 and CD112 in monocytes and MDSCs alone were further examined. MDSCs expressed high levels of CD155 compared with almost no expression in monocytes (MFI: 675±124 vs. 107±23, p=0.015). Moreover, CD112 expression was significantly higher in MDSCs compared to monocytes (MFI: 1714±331 vs. 865±196, p=0.015) (FIG. 13A). To further investigate the mechanisms of MDSC-induced conventional NK cell suppression, pathways utilized by MDSCs including superoxide, arginase, ROS, TGF-β, and iNOS were blocked overnight at the end of MDSC generation. While no substantial difference in CD155 expression was observed when blocking superoxide, arginase, TGF-β or iNOS, inhibition of ROS production with catalase resulted in a significant decrease in the expression of CD155 on MDSCs (55%±23 decrease, p=0.03) (FIG. 13B).

Several studies have shown that increased ROS production in MDSCs correlates with suppression of T cell function. Furthermore, ROS production is increased by enhanced NADPH oxidase activity (NOX2) (Corzo et al. *Journal of Immunology.* 2009; 182(9):5693-701). Here, the ROS production levels in MDSCs were compared to the levels freshly isolated monocytes. Monocytes expressed almost no ROS and were predominantly CD155 negative. In contrast, MDSCs produced high basal levels of ROS and were uniformly CD155 positive (FIG. 13C). Furthermore, inducing ROS production in monocytes by $H_2O_2$ treatment could induce the expression of CD155 in ROS$^+$ monocytes (FIG. 13D).

TIGIT Engagement Inhibits pZAP70/Syk and pERK1/2 and Results in Inhibition of NK Cell Cytotoxicity Given the strong suppressive effect of TIGIT engagement on conventional NK cell function and proliferation, the CD16 induced signaling interaction with TIGIT in NK cells co-cultured with MDSC was analyzed. Compared to when co-cultured with control monocytes, NK cells co-cultured with MDSCs exhibited decreased phosphorylation of ERK1/2 (MFI: 1356±143 vs. 696±202, p=0.03) and ZAP70/Syk (MFI: 159±14 vs. 109±14, p=0.03). Furthermore, blocking TIGIT or inhibiting ROS increased the phosphorylation of ZAP70/Syk and ERK1/2 (p=0.03, FIG. 14A, FIG. 14B). To investigate whether blocking TIGIT or ROS could recover the function of NK cells cultured with MDSCs in cytotoxicity assays, NK cells were cultured with either monocytes or MDSCs were pre-treated with TIGIT blockade or catalase, washed, and then incubated with $^{51}$Cr-labeled K562 cells. NK cell cytotoxicity was significantly decreased after co-culture with MDSCs relative to co-culture with monocytes (FIG. 14C). Neither anti-TIGIT nor catalase had any effect on NK cells cultured alone, but both TIGIT blockade and ROS inhibition completely reversed the suppressive effect mediated by MDSCs (FIG. 14C). Moreover, blocking TIGIT combined with catalase treatment in NK cell and MDSC co-cultures had no additive effect on either pZAP70/Syk and pERK1/2 or NK cell cytotoxicity.

Figure 15C:
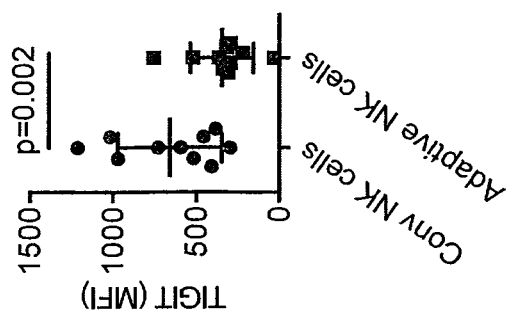
FIG. 15C. PBMCs (n=10) from MDS patients were rested overnight and evaluated for TIGIT expression by flow cytometry.
Figure 15B:
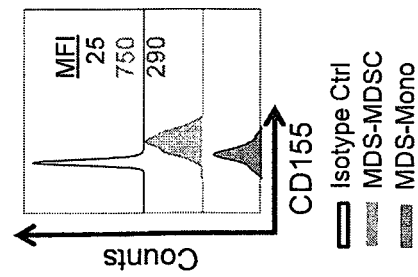
FIG. 15B. MDS-PBMC were stained for CD155 and gated for mMDSC and monocytes. Representative histograms are shown of 15.
Figure 15A:
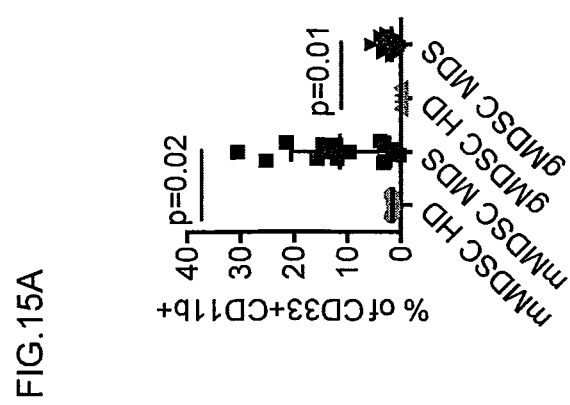
FIG. 15A. PBMC (n=15) from MDS patients and healthy donors (n=6) were rested overnight, stained and the MDSC frequency were determined by flow cytometry. Monocytic MDSCs (mMDSCs) were defined as CD45$^+$Lin$^-$CD11b$^+$CD33$^+$HLA-DR$^{-/low}$CD14$^+$ and granulocytic MDSCs (gMDSCs) as CD45$^+$Lin$^-$CD11b$^+$CD33$^+$CD15$^+$.
Figure 15D:
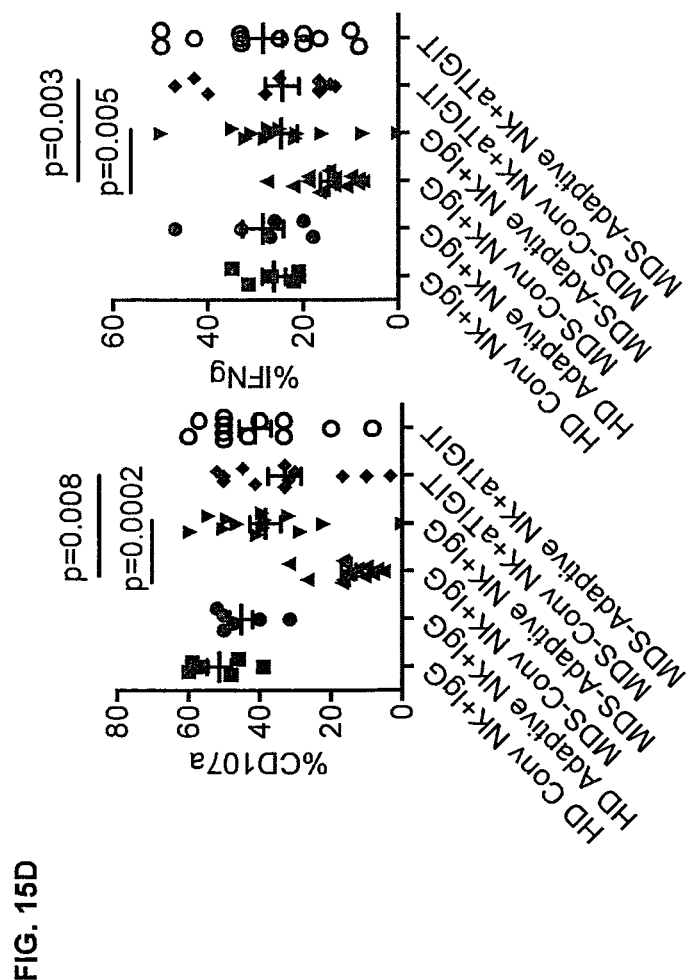
FIG. 15D. PBMCs from healthy donors (HD, n=6) or MDS patients (n=13) were stimulated with IL-15 (10 ng/ml) in the presence of IgG control or anti-TIGIT, and anti-CD16 (1 ug/ml) for 6 hours and assessed for NK cell degranulation and IFN-γ production.

TIGIT-Dependent Suppression of Conventional NK Cells by Myelodysplastic Syndrome (MDS) Patient MDSCs Having identified the contact-mediated suppressive mechanism of cytokine-generated MDSCs, whether this mechanism was operant in a physiologic setting in vivo was investigated. PBMC from CMV-seropositive MDS-patients and healthy donors (HD) were analyzed for the frequency of adaptive NK cells and MDSCs. Although there was a high frequency of adaptive NK cells in the blood of CMV+ MDS patients (n=10, 17%±15% vs 7%±5%), the total NK cell frequency was significantly lower compared to HD (n=8, 1.3%±1.2 vs. 8%±7%). Monocytic MDSCs (mMDSCs) were defined as CD45$^+$Lin$^-$CD11b$^+$CD33$^+$HLA-DR$^{-/low}$CD14$^+$ and granulocytic MDSCs (gMDSCs) as CD45$^+$Lin$^-$CD11b$^+$CD33$^+$CD15$^+$. Compared to healthy blood donors, significant increase in the frequency of both mMD-SCs (1.6±0.2 vs. 11.4±9.2, p=0.02) and gMDSCs (0.02±0.02 vs. 1.84±1.6, p=0.01) was observed in the blood of MDS patients (FIG. 15A). In addition, MDS-MDSCs have increased CD155 expression compared to MDS-monocytes (FIG. 15B). PBMC from MDS patients were evaluated for the expression of TIGIT on conventional and adaptive NK cells. In MDS patients, TIGIT expression was significantly lower on adaptive compared to conventional NK cells (MFI: 347±189 vs. 660±311, p=0.002; FIG. 15C). MDS patient CMV-induced adaptive NK cells exhibited significantly greater function after activation with IL-15 and CD16 stimulation relative to MDS-conventional NK cells. Moreover, adaptive NK cells displayed similar degranulation and IFNγ production as in healthy donor NK cells (FIG. 15D). Blocking TIGIT signaling in conventional NK cells rescued their functional hyporesponsiveness, but there was little added effect on adaptive NK cells that have low levels of TIGIT expression (FIG. 15D).

Figure 15E:
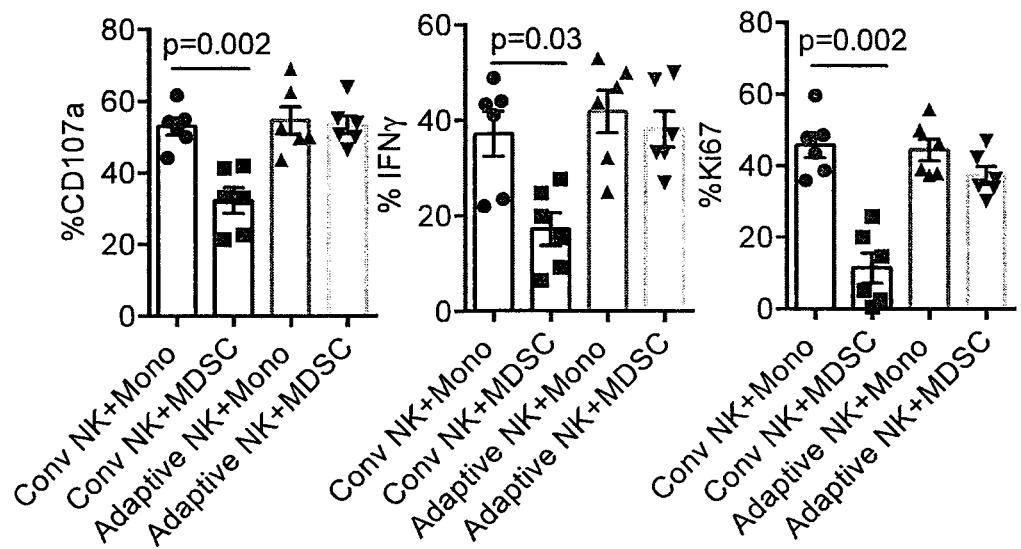
FIG. 15E. Purified NK cells (n=6) from healthy blood donors were co-cultured with autologous monocytes or allogeneic MDSCs enriched from the blood of MDS patients at a 2:1 ratio in the presence of IL-15 (10 ng/mL) for 5 days. Following 6 hours stimulation with anti-CD16, degranulation and IFN-γ production was evaluated in conventional and adaptive NK cells by flow cytometry.
Figure 15F:
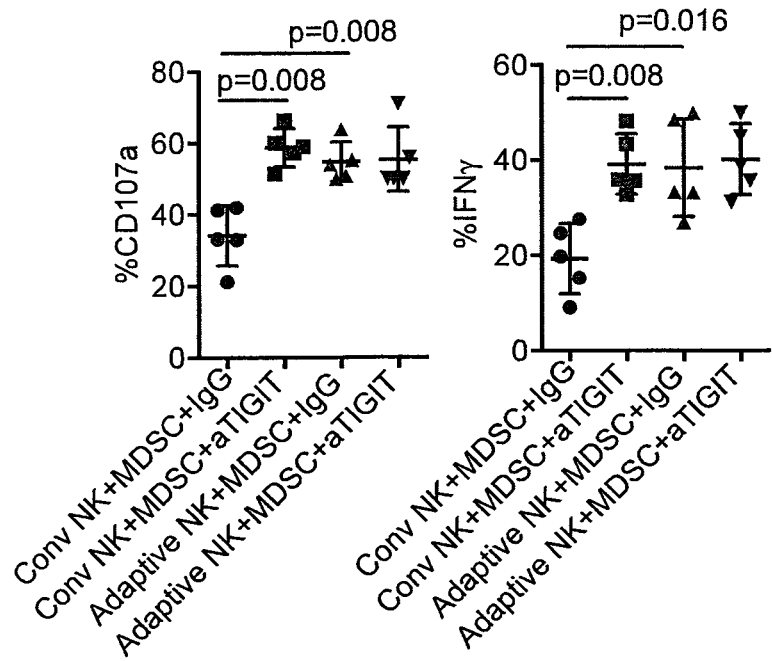
FIG. 15F. Purified NK cells (n=6) from healthy blood donors were co-cultured with allogeneic MDSCs enriched from the blood of MDS patients at a 2:1 ratio in the presence of IL-15 (10 ng/mL) and in the presence or absence of anti-TIGIT (10 ug/mL) for 5 days. 6 hours prior staining, cells were stimulated with anti-CD16 and degranulation and IFN-γ production was evaluated in conventional and adaptive NK cells by flow cytometry. Representative data are shown as mean±SD, and statistical analyses were done on pooled data using the Student's t-test for (FIG. 15A), (FIG. 15C), (FIG. 15D), and Mann-Whitney test for (FIG. 15E) and (FIG. 15F).

The suppressive capacity of MDSCs circulating in the blood of MDS patients on allogeneic NK cells from healthy volunteers was evaluated. Following 5 days of co-culture in the presence of IL-15 and CD16 stimulation, a marked reduction in allogeneic conventional NK cell function was observed compared to that of adaptive NK cells in the same sample (FIG. 15E, FIG. 18C). TIGIT blockade completely reversed the suppressive function of primary MDSCs from MDS patients on conventional NK cells, while no effect was seen on the CMV-induced adaptive NK cells that were inherently resistant to this suppressive mechanism (FIG. 15F). Thus, these data definitively demonstrate that the MDSC suppressive mechanism observed with cytokine-generated MDSCs from normal donors are identical to those of primary MDSCs from MDS patients.

Discussion

There has been an explosion in the immunotherapy literature describing the potential therapeutic benefits of NK and T cell immunotherapy in patients with active cancer. This excitement is fueled by unexpectedly strong clinical results with checkpoint blockade against T cell PD-1/PD-L1 and/or CTLA-4 pathways. Collectively, novel approaches to cancer therapy are undergoing strategic change, with an emphasis on antigen-specific responses and checkpoint blockade. While NK cell responses to targets are determined by a counterbalance of signals via activating and inhibitory receptors, similar checkpoint blockade mechanisms are less understood. In this study, TIGIT/CD155 was identified as a key axis underlying MDSC-induced suppression of conventional NK cells. CMV-induced adaptive NK cells expressed low levels of TIGIT and were not susceptible to MDSC suppression. The function of MDSCs generated from normal blood by cytokine exposure was equivalent to that of MDSCs induced in cancer (MDS) patients, which highlights the physiologic relevance of these findings and their potential translational role. As provided by this disclosure, and without wishing to be bound by theory, there are at least two ways to overcome TIGIT-induced immunosuppression of NK cells. The first is TIGIT blockade, which restores CD16 signaling in conventional NK cells to normal levels. The second is the expansion of TIGIT-resistant adaptive NK cells after CMV-exposure. Here it is shown that a subset of NK cells, with or without being isolated, can be expanded, and optionally modulated to carry out resistance to tumor induced immune suppression by maintaining a low expression level of TIGIT.

Immunosuppressive cell types, including MDSCs, accumulate in the tumor microenvironment and exert suppressive pressure on effector cells as such CTLs and NK cells resulting in a diminished capability for tumor clearance. Cytokine-induced MDSCs suppress polyclonal NK cell proliferation, degranulation and IFN-γ production. However, it was unexpectedly found that it is possible for NK cells to carry out resistance to MDSC suppression by segregating adaptive and conventional NK cells to obtain a subpopulation of NK cells that are amenable to blocking MDSC suppression. On the basis of the resistance of adaptive NK cells to MDSC suppression, whether there were any distinct phenotypic changes in adaptive versus conventional NK cells when co-cultured with MDSC compared to normal monocytes was investigated. TIGIT expression was found to be significantly lower in adaptive NK cells compared with conventional NK cells.

CD112 and CD155 are regulated by cellular stress and bind TIGIT with low and high affinity respectively. Both receptors are highly expressed on transformed cells. As shown herein, conversion of monocytes into MDSCs is associated with increased CD112 and induction of CD155 expression. CD155 expression was dependent on reactive oxygen species (ROS) production, and MDSCs produced high levels of ROS.

TIGIT engagement on NK cells following co-culture with MDSCs resulted in substantially less phosphorylation of ZAP70/Syk and ERK1/2 compared with NK cells co-cultured with CD155$^-$ monocytes. Blocking TIGIT or inhibiting ROS production reversed this defect in proximal signaling. Without wishing to be bound by theory, the findings herein reveal a role for TIGIT as an immune checkpoint-regulating, MDSC-mediated suppressor of NK cell signaling. As shown herein, blocking TIGIT or inhibiting ROS resulted in enhanced cytotoxicity of NK cells against K562. Notably, blood-circulating MDSCs from patients with MDS could not suppress conventional NK cells in the presence of anti-TIGIT. These results show that the phenotypic MDSCs induced by MDS are functionally suppressive, a finding that may contribute to the clinical progression of this disease.

These data implicate blockade of TIGIT to enhance the anti-tumor role of NK cells in cancer immunotherapy. Alternatively, clonal expansion of adaptive NK cells in cancer patients could improve tumor targeting with minimal suppression of the tumor microenvironment. Such expansion is seen after CMV reactivation in immunosuppressed patients (Davis et al. *Biology of Blood and Marrow Transplantation: Journal of the American Society for Blood and Marrow Transplantation.* 2015; 21(9):1653-62; Foley et al. *Journal of Immunology.* 2012; 189(10):5082-8), and could be promoted by infusion of adaptive NK cells or by CMV vaccines. Treatment with CMV envelope glycoprotein B and genetic immunization with dendritic cell CMV vaccines have been shown to be safe and feasible (Pass et al. *The New England Journal of Medicine.* 2009; 360(12):1191-9; Garu et al. *Molecular Therapy.* 2015; doi:10.1038/mt.2015.215). In summary, these novel data provide a new perspective on the suppression of different NK cell subsets by MDSCs.

Material and Methods

Patient and Healthy Donors

Normal peripheral blood was obtained from healthy subjects. Frozen peripheral blood mononuclear cells (PBMC)

from myelodysplastic syndrome patients (MDS, n=15) were obtained from the National Marrow Donor Program (NMDP)/Center for International Blood and Marrow Transplant Research. All healthy and MDS patient donors were CMV seropositive. All samples were de-identified and use was approved by the University of Minnesota and NMDP institutional review board in accordance with the Declaration of Helsinki.

Cell Isolation

PBMC from MDS patients and healthy blood donors were collected after Ficoll gradient centrifugation (Ficoll-Paque Plus, GE Healthcare, Little Chalfont, United Kingdom). Thereafter, cells were seeded at a destiny of $2\times10^6$/mL in RPMI medium containing 10% heat inactivated FBS, IL-6 (10 ng/mL, Sigma-Aldrich, St. Louis, Mo.) and GM-CSF (10 ng/mL, R&D Systems) for a week and refreshed on day 3 of culture to generate MDSCs (Koehn et al. *Blood.* 2015; 126(13):1621-8). Next, HLA-DR$^+$ cells were isolated with anti-human HLA-DR microbeads (Miltenyi Biotech, Bergisch Gladbach, Germany), and MDSCs were thereafter purified from the HLA-DR$^-$ fraction using anti-CD33 microbeads (Miltenyi Biotech, Bergisch Gladbach, Germany). Monocytic MDSC were used in all shown experiments (≥85% CD14$^+$HLA-DR$^-$). NK and T cells were isolated from overnight rested PBMC by negative depletion (EasySep Human NK Cell Enrichment Kit, Stemcell Technologies, Vancouver, Canada) or CD3 microbeads (Miltenyi Biotech, Bergisch Gladbach, Germany). Control monocytes were isolated from overnight rested PBMC using anti-CD33 microbeads.

Proliferation Assays

Purified monocytes or cytokine-induced MDSCs were seeded in duplicates in 96 well U-bottom plates at 1:1-1:16 ratios with CellTrace violet dye (5 uM, Invitrogen, Carlsbad, Calif.)-labeled autologous T or NK cells ($1\times10^5$) in RPMI medium (Gibco, Minneapolis, Minn.) supplemented with 10% FBS (referred below as medium). T cells were stimulated with anti-CD3/CD28 activation beads (40 beads/well) and IL-15 (1 ng/mL) or IL-15 (10 ng/mL) alone for NK cells and cultured for 3-5 days. Cells were acquired by LSRII flow cytometer (BD Biosciences) and data analyzed by FlowJo (Tree Star, Ashland, Oreg.).

Flow Cytometry Analysis

Purified NK cells or MDS PBMC (FIG. 17) cultured with monocytes or MDSCs for different time points and with different stimuli were resuspended in staining buffer (PBS containing 0.5% human AB serum) and stained with fluorochrome-conjugated antibodies (Table IV). Detection of CD107a, Ki67, IFN-γ, and TNFα production by cultured NK cells were performed using a Foxp3/Transcription Factor Fixation/Permeabilization kit (eBioscience, Inc., San Diego, Calif.) according to the manufacturer's instructions. Before fixation and extracellular staining, NK cells were treated with blefeldin A and monensin (GolgiPlug and GolgiStop; BD Bioscience, Franklin Lake, N.J.) at 37° C. for 6 hours. MDSCs were stained with antibodies against the following antigens to determine their purity and phenotype prior co-culture with NK cells: CD11b, HLA-DR, CD33, CD14, CD15, CD66b, CD56, CD3, CD19 (lin–), and fixabale dead cell marker (Table IV). In a few experiments prior to staining, MDSCs were cultured alone overnight in the presence of reagents targeting different suppressive mechanisms of MDSCs, including 10 μg/mL neutralizing antibodies for TGFβ (R&D systems), 200 IU/mL of the ROS scavenger catalase (Sigma-Aldrich, St. Louis, Mo.) or superoxide dismutase (Sigma-Aldrich), 500 μmol/L arginase inhibitor N(ω)-hydroxy-nor-1-arginine (nor-NOHA; Calbiochem) or iNOS inhibitor NG-monomethyl-1-arginine (L-NMMA; Sigma-Aldrich, St. Louis, Mo.) and stained for CD155 (PVR). All cells were acquired by LSRII and analyzed by FlowJo. Adaptive and conventional NK cells were gated and identified according to the gating strategy in FIG. 17.

Transwell Assays

Purified NK cells from healthy blood donors were co-cultured for 5 days with autologous MDSCs or freshly isolated monocytes at a 2:1 ratio in the presence of IL-15 (10 ng/mL) and seeded in 24-well plates in contact or separated with transwell inserts (0.4 um pores) (Corning, Corning, N.Y.) allowing soluble factor exchange only. Cells were stimulated with anti-CD16 for 6 hours prior staining for degranulation and IFNγ production and as described above.

Confocal Microscopy

MDSCs and monocytes were pre-labeled with Cell-Tracker Blue (14 μM, Invitrogen, Carlsbad, Calif.) for 20 min. They were then co-cultured with IL-15 (10 ng/mL) overnight pre-activated NK cells for 40 min. Mixed cells were loaded on a poly-lysine pretreated cover glass for 30 min, blocked with 3% BSA and fixed in 2% paraformaldehyde for 30 min at 37° C. Following fixation, cells were stained with anti-TIGIT and anti-PVR (CD155) for 2 hours at RT and then 1 hour with the fluorescence-labeled secondary antibodies before confocal microscopy.

TABLE IV

Antibodies and fluorescent dyes used in different Examples.

| Marker | Clone | Fluorochrome | Manufactory |
| --- | --- | --- | --- |
| CD3 | OKT3 | APC/CY7 | Biolegend |
| CD3 | OKT3 | BV785 | Biolegend |
| CD56 | NCAM | APC/CY7 | Biolegend |
| CD56 | NCAM | PE/CY7 | Biolegend |
| CD57 | NK-1 | BV605 | BD Biosciences |
| CD45 | HI30 | BV711 | Biolegend |
| HLA-DR | L243 | AF488 | Biolegend |
| CD11b | ICRF44 | PE | Biolegend |
| CD33 | WM53 | APC | Biolegend |
| CD66b | G10F5 | AF700 | Biolegend |
| CD14 | M5E2 | Pacific B | BD Biosciences |
| CD14 | M5E2 | APC/CY7 | BD Biosciences |
| CD19 | HIB19 | APC/CY7 | BD Biosciences |
| CD16 | 3G8 | AF700 | Biolegend |
| NKp44 | P44-8 | APC | BD Biosciences |
| NKp46 | 9E2 | PerCP-eFluor ® 710 | BD Biosciences |
| DNAM-1 | 11A8 | APC | Biolegend |
| pZAP/Syc | 17A/PZAP70 | AF647 | BD Biosciences |
| pERK | 20A | APC | BD Biosciences |
| CD155 (PVR) | SKII.4 | PerCP/Cy5.5 | Biolegend |
| CD112 (Nectin2) | TX31 | PE/CY7 | Biolegend |
| CellTrace | | Violet | Invitrogen |
| CD107a | H4A3 | PerCP/Cy5.5 | Biolegend |
| IFNγ | 4S.B3 | BV650 | Biolegend |
| Ki67 | B56 | AF700 | BD Biosciences |
| TIGIT | 741182 | APC | R&D systems |
| ROS | | 520 nm | eBiosciences |
| CellTracker | | Blue | Invitrogen |
| NKG2C | 134591 | PE | R&D systems |
| FCεRγ | RB Polyclonal | FITC | EMD millipore |
| PD-1 | MIH4 | APC | eBiosciences |
| NKG2A | 131411 | APC | R&D |
| TIM-3 | F38-2E2 | BV421 | Biolegend |
| TNFα | MAb11 | BV421 | BD Biosciences |
| Fixable dead cell marker | | Near-IR | Invitrogen |

Phosflow

Purified NK cells from healthy blood donors were co-cultured with autologous MDSCs or freshly isolated monocytes at a 2:1 ratio in the presence of IL-15 (10 ng/mL) and in the presence or absence of blocking antibodies against TIGIT (10 ug/mL), or catalase (200 IU/mL) for 5 days. Cells were then washed, rested for 4 hours, and stimulated with anti-CD16 agonist antibody for 10 and 30 min. before analysis of Zap-70 and ERK1/2 phosphorylation respectively. Cells were fixed and permeabilized with BD fixation buffer and permeabilization buffer III and stained for pZap-70 (pY319)/Syk (pY352) and pERK1/2 (pT202/pY204) according to the manufacturer's instructions (BD Biosciences, Franklin Lake, N.J.).

Chromium Release Assays

Following 5 days of co-culture with monocytes or MDSCs in the presence or absence of blocking antibodies against TIGIT (10 ug/mL) or ROS scavenger catalase (200 IU/mL), NK cell cytotoxicity was analyzed by chromium ($^{51}$Cr) release assays (4 hours) against K562 (ATCC, Manassas, Va.) cells at a 5:1-2.5:1 effector:target ratios. $^{51}$Cr release was measured by a γ scintillation counter (Perkin Elmer, Waltham, Mass.), and specific target lysis was determined.

Ex Vivo Analysis of MDSC Suppression

PBMC from MDS patients and healthy donors were rested overnight, and MDSCs were isolated as described above. NK cells and monocytes were isolated from overnight rested healthy PBMC as previously described. NK cells were co-cultured with autologous monocytes or allogeneic MDS MDSCs at a 2:1 ratio in the presence of IL-15 (10 ng/mL) for 5 days. Following 6 hours stimulation with anti-CD16, NK cells were evaluated for degranulation, proliferation and IFN-γ and TNFα production in the presence or absence of blocking antibodies against TIGIT.

Statistical Analysis

All data were first analyzed in the software mentioned above and summarized by Prism Version 6 software (GraphPad Software, La Jolla, Calif.). All data were first tested for normal distribution. Thereafter, differences among groups were analyzed by a Student's t test or nonparametric, Mann-Whitney U tests (as indicated in the figure legends). Data were presented as means and SEM for in vitro assays and means and SD for experiments done with cells from MDS patients. Representative histograms or images were chosen based on the average values.

Example 8

Mature Dendritic Cells Pulsed with a Pool of CMV Peptides Induces Adaptive NK Cell Expansion.

Monocytes (2×10$^6$/mL) were cultured in CellGro media (2.5% human AB serum) supplemented with 100 ng/mL GM-CSF and 20 ng/mL IL-4 to induce maturation of monocytes to immature dendritic cells. After 5 days of culture, immature dendritic cells were harvested, spun down, and seeded at 1×10$^6$ cells/mL in fresh CellGro media (2.5% human AB serum) supplemented with GM-CSF (100 ng/mL) and IL-4 (20 ng/mL) (for immature dendritic cells) or GM-CSF (100 ng/mL), IL-4 (20 ng/mL), polyinosinic:polycytidylic acid (Poly I:C) (20 μg/mL), lipopolysaccharide (LPS) (10 ng/mL), and IFN-γ (1000 IU/mL) (for mature dendritic cells). Selected mature dendritic cell cultures were further supplemented with or without a CMV pp65 peptide pool (10 μg/mL) (Catalog No. 11549, National Institutes of Health AIDS Reagent Program, Germantown, Md.; a list of the peptides in the pool is available on the world wide web at aidsreagent.org/pdfs/11549_TAB_002.pdf) or an HIV PTE Gag peptide pool (10 μg/mL) (Catalog No. 12437, National Institutes of Health AIDS Reagent Program, Germantown, Md.; a list of peptides in the pool is available on the world wide web at aidsreagent.org/support_docs/11554_Lot21164_Solubility-MW-Purity.docx). Autologous PBMCs were thawed on Day 5 and rested overnight in RPMI supplemented with 10% FBS at 37° C.

On Day 6, CD3$^-$CD56$^+$ NK cells and CD14$^+$ monocytes were isolated by bead selection from PBMCs that were rested overnight. Autologous co-cultures were then set up with NK cells and either fresh monocytes, cultured immature dendritic cells, cultured mature dendritic cells, cultured CMV peptide-supplemented mature dendritic cells, or cultured HIV peptide-supplemented mature dendritic cells in the presence of IL-15 (10 ng/mL) at a 1:1 ratio in 24-well plates. Culture conditions with NK cells alone were also set up. Cells were then cultured for 12-14 days prior to FACS analysis.

Figure 19:
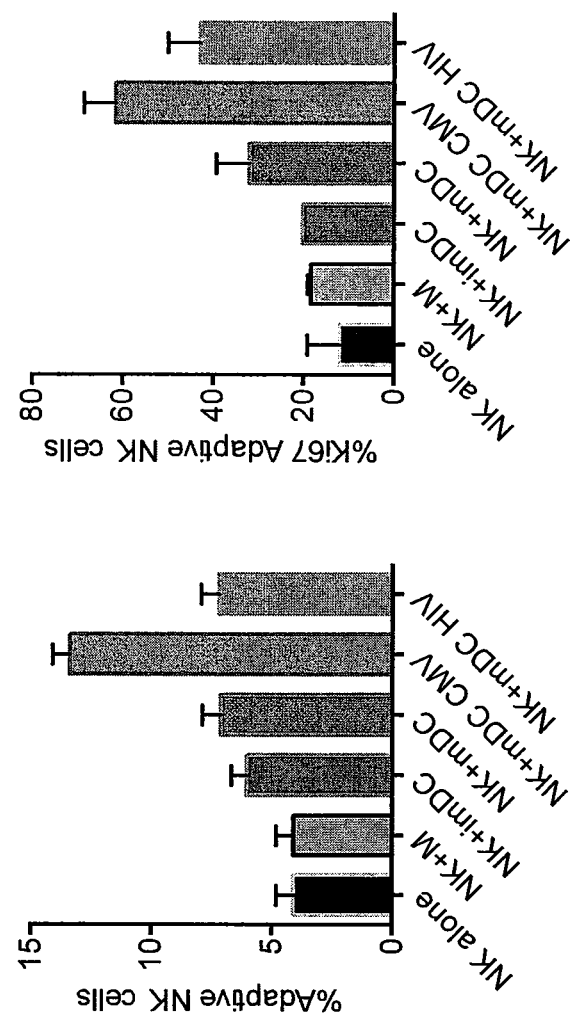
FIG. 19 shows pulsing mature dendritic cells with a pool of CMV peptides induces adaptive NK cell expansion. NK cells, unfractionated monocytes, immature dendritic cells (imDC), and mature dendritic cells (mDC) were isolated from peripheral blood mononuclear cells from healthy CMV seropositive donors. NK cells were then cultured with 10 ng/mL IL-15 or co-cultured with the indicated autologous cell types and 10 ng/mL IL-15. Selected mature dendritic cell cultures were further supplemented with a CMV pp65 peptide pool or an HIV PTE Gag peptide pool. Cells were harvested after 12 to 14 days, and FACS was used to determine the frequencies of adaptive NK cells (defined as CD3$^-$CD56$^+$CD57$^+$FcεR1γ$^-$) (left panel) and percentages of adaptive NK cells actively proliferating (right panel) in each culture condition. Cumulative data from one experiment with 5 donors is shown.

Results are shown in FIG. 19, which demonstrates that pulsing mature dendritic cells with a pool of CMV peptides induces adaptive NK cell expansion.

Example 9

NK Cells from CMV Seropositive Donors Skew Towards a CD45RA-CD45RO+ Phenotype when Cultured in the Presence of Autologous Monocytes and IL-15.

CD3/CD19-depleted peripheral blood mononuclear cells from typed healthy CMV seronegative and seropositive donors were cultured with 10 ng/mL IL-15. Percentages of CD3$^-$ CD56$^+$CD45RA$^-$CD45RO$^+$ NK cells from CMV seronegative and CMV seropositive donors pre- and post-culture were measured using FACS.

Figure 20:
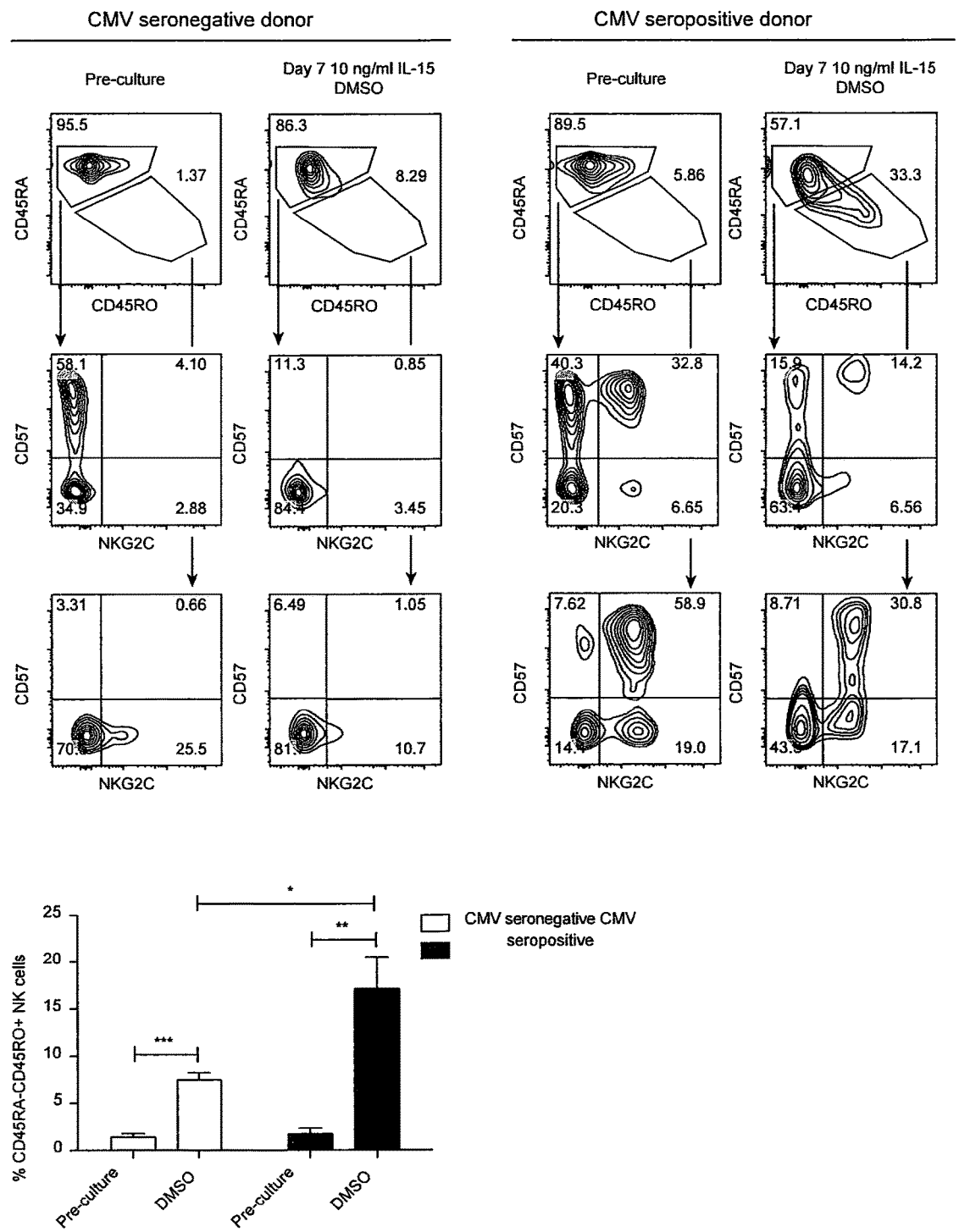
FIG. 20 shows NK cells from CMV seropositive donors skew towards a CD45RA$^-$ CD45RO$^+$ phenotype when cultured in the presence of autologous monocytes and IL-15. CD3/CD19-depleted peripheral blood mononuclear cells from typed healthy CMV seronegative and seropositive donors were cultured with 10 ng/mL IL-15. After 7 days, cells were harvested and analyzed by FACS. Shown are representative phenotypes from one CMV seropositive and one CMV seronegative donor both before and after culture (top). Cumulative data showing the percentages of CD3$^-$CD56$^+$CD45RA$^-$CD45RO$^+$ NK cells from five CMV seronegative and eight CMV seropositive donors pre- and post-culture are shown (bottom). Data are representative of two independent experiments. Paired student's t-tests were used to determine statistical significance within groups, and unpaired student's t-tests were used to determine statistical significance between groups (CMV seropositive and CMV seronegative). *p≤0.05, p≤0.01, *p≤0.001.

As shown in FIG. 20, NK cells from CMV seropositive donors skew towards a CD45RA$^-$ CD45RO$^+$ phenotype when cultured in the presence of autologous monocytes and IL-15.

Example 10

Adaptive NK Cells are Resistant to Treg-Mediated Suppression.

Regulatory T cells (Tregs) were generated in vitro using the following method: PBMCs were isolated from CMV seropositive donors by density gradient centrifugation. CD4$^+$ T cells were then isolated from total PBMCs by magnetic bead separation. CD4$^+$ T cells were then sorted to isolate the CD4$^+$CD25$^{hi}$CD127$^{low}$ Treg population. Sorted Tregs were then expanded in culture for 21 days with an irradiated K562-mbIL-21 feeder line, anti-CD3/CD28 beads, and 300 U/ml IL-2. Expanded Tregs were then cultured at 1:1, 1:2, 1:4, or 1:8 ratios with autologous or allogeneic NK cells and HLA-DR$^+$ antigen presenting cells for 6 days in media supplemented with 50 U/ml IL-2. For functional experiments, NK cells were stimulated for 5 hours with 1 μg/ml anti-CD16 agonist antibody, 5 ng/ml IL-12, and 50 ng/ml IL-18.

Figure 21C:
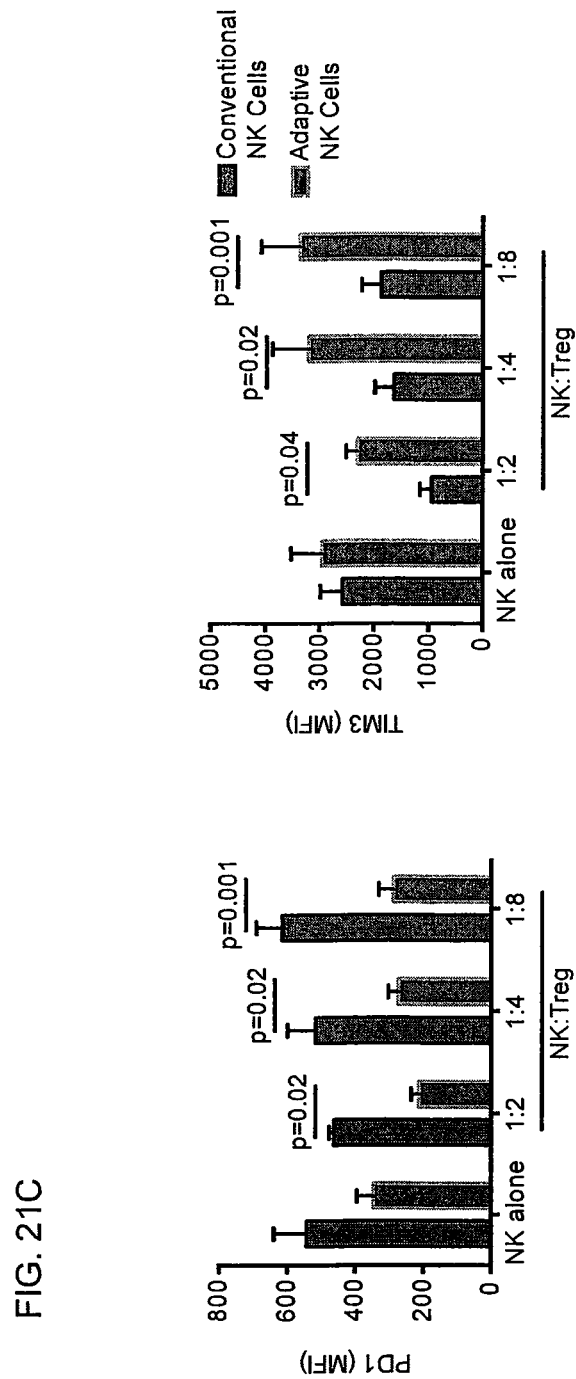
FIG. 21C. FACS was used to determine the expression of PD1 and TIM-3 on cultured NK cells. Results are from two independent experiments. p values were generated from paired Student's t-tests.

Flow cytometry was used to analyze proliferation of conventional (CD56$^+$CD57$^+$FcεRγ$^+$ NKG2C$^-$) and adaptive (CD56$^+$CD57$^+$FcεRγ$^-$ NKG2C$^+$) NK cell subsets. As shown in FIG. 21, adaptive NK cells are resistant to Treg-mediated suppression. FIG. 21A shows the percentages of NK cells that exhibited CellTrace dye dilution in each culture condition. FIG. 21B shows degranulation (as measured by CD107a expression) and IFN-γ production of cultured NK cells following stimulation with anti-CD16 agonist antibody, IL-12 and IL-18. FIG. 21C shows the expression of PD1 and TIM-3 on cultured NK cells, as measured by FACS using anti-PD1 (clone MIH4; color: APC; eBioscience Inc., San Diego, Calif.) and anti-TIM3 (clone: F382E2; color: BV650, Biolegend, San Diego, Calif.). Results are from two independent experiments. p-values were generated from paired Student's t-tests.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

What is claimed is:

1. A method comprising culturing a population of NK cells of a blood sample from a subject in a medium to obtain a population comprising an adaptive NK cell, wherein the medium comprises:
   (i-a) one or more of IL-15, IL-21, and a Notch ligand;
   (ii-a) a CMV peptide-supplemented mature dendritic cell;
   (iii-a) autologous monocytes and IL-15 and wherein the subject is CMV seropositive; or
   (iv-a) at least one of rapamycin and an activator of CD16 signaling;
   wherein the adaptive NK cell is $CD56^{dim}$ and is one or more of $NKG2C^+$ and $TIGIT^{low}$;
wherein said culturing step further comprises:
   (i-b) contacting the NK cells of the blood sample with an inhibitor of at least one of PLZF, TIGIT, or PD-1;
   (ii-b) contacting the NK cells of the blood sample with a TIGIT inhibitor; or
   (iii-b) genetically knocking down at least one of PLZF, TIGIT, or PD-1 in the NK cells of the blood sample or in the adaptive NK cell or both.

2. The method of claim 1, wherein
   (i) the TIGIT inhibitor comprises an antibody against TIGIT;
   (ii) the adaptive NK cell is at least one of $CD57^+$, $SYK^-$, $Fc\epsilon R\gamma^-$, $EAT-2^-$, $CD45RO^+$, and $CD45RA^-$;
   (iii) the adaptive NK cell exhibits reduced expression of PLZF compared to the population of NK cells prior to culture;
   (iv) the adaptive NK cell exhibits an enhanced anti-tumor immune activity compared to the population of NK cells prior to culture; or
   (v) the adaptive NK cell exhibits one or more of increased cytotoxicity, increased cytokine production, increased persistence, and increased resistance to T regulatory cells compared to the population of NK cells prior to culture.

3. A method comprising culturing a population of NK cells of a blood sample obtained from a subject in a medium to obtain a population comprising an adaptive NK cell, wherein the medium comprises:
   (i) one or more of IL-15, IL-21, and a Notch ligand;
   (ii) a CMV peptide-supplemented mature dendritic cell;
   (iii) autologous monocytes and IL-15 and wherein the subject is CMV seropositive; or
   (iv) at least one of rapamycin and an activator of CD16 signaling;
   wherein the adaptive NK cell is $CD56^{dim}$ and is one or more of $NKG2C^+$ and $TIGIT^{low}$;
   wherein the method further comprising administering a cytomegalovirus (CMV) vaccine to the subject.

4. A composition comprising an enriched or isolated population of adaptive NK cells obtained by the method of claim 3, wherein the adaptive NK cells
   (i) are one or more of $NKG2C^+$, $CD57^+$, and $TIGIT^{low}$;
   (ii) are $CD3^-$ and at least one of $CD57^+$, $NKG2C^+$, $SYK^-$, $Fc\epsilon R\gamma^-$, $EAT-2^-$, $TIGIT^{low}$, $CD45RO^+$, and $CD45RA^-$;
   (iii) exhibit reduced expression of at least one of PLZF and PD-1 compared to a canonical NK cell;
   (iv) are $NKG2C^+$;
   (v) exhibit an enhanced anti-tumor immune activity compared to a canonical NK cell;
   (vi) can overcome myeloid-derived suppressor cell (MDSC)-induced suppression of an immune response;
   (vii) can overcome Treg-induced suppression of an immune response; or
   (viii) are long-lived compared to a canonical NK cell.

5. The composition of claim 4, wherein the composition further comprises (i) at least one of a CD155 inhibitor, a TIGIT inhibitor, and an inhibitor of the production of reactive oxygen species (ROS); and/or (ii) a pharmaceutically acceptable carrier.

6. The composition of claim 5, wherein
   (i) the inhibitor of the production of ROS comprises a catalase; or
   (ii) the ROS production inhibitor or the CD155 inhibitor is present in an amount sufficient to reduce the expression of CD155 on a myeloid-derived suppressor cell (MDSC).

7. A composition comprising an enriched or isolated population of adaptive NK cells obtained by the method of claim 1, wherein the adaptive NK cells
   (i) are one or more of $NKG2C^+$, $CD57^+$, and $TIGIT^{low}$;
   (ii) are $CD3^-$ and at least one of $CD57^+$, $NKG2C^+$, $SYK^-$, $Fc\epsilon R\gamma^-$, $EAT-2^-$, $TIGIT^{low}$, $CD45RO^+$, and $CD45RA^-$;
   (iii) exhibit reduced expression of at least one of PLZF and PD-1 compared to a canonical NK cell;
   (iv) are $NKG2C^+$;

(v) exhibit an enhanced anti-tumor immune activity compared to a canonical NK cell;
(vi) can overcome myeloid-derived suppressor cell (MDSC)-induced suppression of an immune response;
(vii) can overcome Treg-induced suppression of an immune response; or
(viii) are long-lived compared to a canonical NK cell.

8. The composition of claim 7, wherein the composition further comprises (i) at least one of a CD155 inhibitor, a TIGIT inhibitor, and an inhibitor of the production of reactive oxygen species (ROS); and/or (ii) a pharmaceutically acceptable carrier.

9. The composition of claim 8, wherein
(i) the inhibitor of the production of ROS comprises a catalase; or
(ii) the ROS production inhibitor or the CD155 inhibitor is present in an amount sufficient to reduce the expression of CD155 on a myeloid-derived suppressor cell (MDSC).

10. A method for treating or preventing cancer, a precancerous condition, or a virus in a subject, the method comprising administering to the subject the composition of claim 7.

11. The method of claim 10, wherein the subject comprises a myeloid-derived suppressor cell (MDSC).

* * * * *